US007915212B2

(12) United States Patent  
Yeung et al.

(10) Patent No.: US 7,915,212 B2
(45) Date of Patent: Mar. 29, 2011

(54) BLOCK POLYMERS, COMPOSITIONS AND METHODS OF USE FOR FOAMS, LAUNDRY DETERGENTS, SHOWER RINSES AND COAGULANTS

(75) Inventors: Dominic Wai-Kwing Yeung, Ontario (CA); Vance Bergeron, Antony (FR); Jean-Francois Bodet, Mason, OH (US); Mark R. Sivik, Ft. Mitchell, KY (US); Bernard W. Kluesener, Harrison, OH (US); William M. Scheper, Lawrenceburg, IN (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/966,675

(22) Filed: Dec. 28, 2007

(65) Prior Publication Data
US 2008/0131393 A1    Jun. 5, 2008

Related U.S. Application Data

(60) Division of application No. 11/025,967, filed on Jan. 3, 2005, now Pat. No. 7,335,700, which is a continuation of application No. 09/698,149, filed on Oct. 30, 2000, now Pat. No. 6,864,314, which is a continuation-in-part of application No. 09/318,942, filed on May 26, 1999, now abandoned.

(51) Int. Cl.
*C11D 3/20* (2006.01)
*C08F 293/00* (2006.01)
*C08F 295/00* (2006.01)

(52) U.S. Cl. ........ 510/238; 510/191; 510/362; 510/531; 510/535; 525/294; 525/299

(58) Field of Classification Search .................... 525/91, 525/89, 230, 329.9, 330.5, 191, 221, 222; 424/70.27; 524/762; 510/531, 191, 238, 510/362, 535
See application file for complete search history.

(56) References Cited

U.S. PATENT DOCUMENTS

| | | |
|---|---|---|
| 3,099,636 A | 7/1963 | Skiles |
| 3,249,455 A | 5/1966 | Williams |
| 3,454,500 A | 7/1969 | Lancashire |
| 3,671,502 A | 6/1972 | Samour et al. |
| 3,846,380 A | 11/1974 | Fujimoto et al. |
| 3,960,763 A | 6/1976 | Lambou et al. |
| 3,963,649 A | 6/1976 | Spadini et al. |
| 4,304,703 A | 12/1981 | Das |
| 4,454,060 A | 6/1984 | Lai et al. |
| 4,486,489 A | 12/1984 | George |
| 4,528,111 A | 7/1985 | Su |
| 4,536,298 A | 8/1985 | Kamei et al. |
| 4,542,175 A | 9/1985 | Fink et al. |
| 4,556,509 A | 12/1985 | Demangeon et al. |
| 4,579,681 A | 4/1986 | Ruppert et al. |
| 4,622,378 A | 11/1986 | Gosselink |
| 4,661,288 A | 4/1987 | Rubingh et al. |
| 4,713,182 A | 12/1987 | Hiltz et al. |
| 4,734,099 A | 3/1988 | Cyprien |
| 4,784,789 A | 11/1988 | Jeschke et al. |
| 4,806,591 A | 2/1989 | Probst et al. |
| 4,814,101 A | 3/1989 | Schieferstein et al. |
| 4,832,950 A | 5/1989 | Takaya et al. |
| 4,835,211 A | 5/1989 | Noda et al. |
| 4,879,051 A | 11/1989 | Lo et al. |
| 4,923,694 A | 5/1990 | Shih et al. |
| 4,964,873 A | 10/1990 | Duffin et al. |
| 5,027,898 A | 7/1991 | Naae |
| 5,042,583 A | 8/1991 | D'Souza et al. |
| 5,085,698 A | 2/1992 | Ma |
| 5,104,643 A | 4/1992 | Grollier et al. |
| 5,169,441 A | 12/1992 | Lauzon |
| 5,182,331 A | 1/1993 | Liao et al. |
| 5,218,021 A | 6/1993 | Clark et al. |
| 5,219,945 A | 6/1993 | Dicker et al. |

(Continued)

FOREIGN PATENT DOCUMENTS

AU          9915321          6/1999

(Continued)

OTHER PUBLICATIONS

P. Chaumont, D. Colombani, L. Boiteau, J.P. Lamps, M. Zink, C.P.R. Nair, and P. Charmot, *Free Radical Synthesis of Functional Polymers Involving Addition-Fragmentation Reactions*, American Chemical Society (Chapter 22, p. 362-376) (1998).
J. Chiefari, Y. K. Chong, F. Ercole, J. Krstina, J. Jeffrey, T. Le, R. Mayadunne, G. Meigs, C. Moad, G. Moak, E. Rizzardo, S. Thang *Living Free-Radical Polymerization by Reversible Addition-Fragmentation Chain Transfer: The RAFT Process*, Macromolecules, 31, p. 5559-5562 (1998).
A. Sebenik, *Living Free-Radical Block Copolymerization Using Thio-Iniferters*, Prog. Polym. Sci. vol. 23, p. 875-917 (1998).

(Continued)

*Primary Examiner* — Irina S Zemel
*Assistant Examiner* — Jeffrey Lenihan
(74) *Attorney, Agent, or Firm* — Novak Druce + Quigg LLP

(57) ABSTRACT

The present invention relates to a block polymeric material. Typically the block polymer comprises units capable of having an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12. The polymeric material is a suds enhancer and a suds volume extender for personal care products such as soaps and shampoos. The compositions have increased effectiveness for preventing redeposition of grease during hand and body washing. The polymers are also effective as a soil release agent in fabric cleaning compositions. The polymeric material is also effective in oil well treating foam, fire-fighting foam, hard surface cleaning foam, shaving cream, post-foaming shaving gel, dephiliatories and as a coagulant/retention aid for titanium dioxide in paper making.

22 Claims, No Drawings

U.S. PATENT DOCUMENTS

| | | | |
|---|---|---|---|
| 5,221,334 A | 6/1993 | Ma et al. |
| 5,232,632 A | 8/1993 | Woo et al. |
| 5,244,935 A | 9/1993 | Oshibe et al. |
| 5,277,899 A | 1/1994 | McCall |
| 5,308,532 A | 5/1994 | Adler et al. |
| 5,338,406 A | 8/1994 | Smith |
| 5,338,541 A | 8/1994 | Matz et al. |
| 5,346,699 A | 9/1994 | Tiernan et al. |
| 5,413,731 A | 5/1995 | Adler et al. |
| 5,415,860 A | 5/1995 | Beucherie et al. |
| 5,496,475 A | 3/1996 | Jho et al. |
| 5,532,023 A | 7/1996 | Vogel et al. |
| 5,536,452 A | 7/1996 | Black |
| 5,549,869 A | 8/1996 | Iwakawa |
| 5,580,819 A | 12/1996 | Li et al. |
| 5,587,022 A | 12/1996 | Black |
| 5,612,308 A | 3/1997 | Woo et al. |
| 5,614,473 A | 3/1997 | Dino et al. |
| 5,616,547 A | 4/1997 | Ponce et al. |
| 5,658,961 A | 8/1997 | Cox, Sr. |
| 5,665,466 A | 9/1997 | Guez et al. |
| 5,679,630 A | 10/1997 | Baeck et al. |
| 5,686,024 A | 11/1997 | Dahanayake et al. |
| 5,705,033 A | 1/1998 | Gerard et al. |
| 5,706,895 A | 1/1998 | Sydansk |
| 5,714,001 A | 2/1998 | Savoly et al. |
| 5,735,955 A | 4/1998 | Monaghan et al. |
| 5,783,533 A | 7/1998 | Kensicher et al. |
| 5,811,386 A | 9/1998 | Mueller et al. |
| 5,821,203 A | 10/1998 | Williamson |
| 5,853,710 A | 12/1998 | Dehan et al. |
| 5,858,343 A | 1/1999 | Szymczak |
| 5,863,880 A | 1/1999 | Shih et al. |
| 5,882,541 A | 3/1999 | Achtmann |
| 5,902,574 A | 5/1999 | Stoner et al. |
| 5,902,778 A | 5/1999 | Hartmann et al. |
| 5,997,886 A | 12/1999 | Peffly et al. |
| 6,207,631 B1 | 3/2001 | Kasturi et al. |
| 6,251,849 B1 | 6/2001 | Jeschke et al. |
| 6,277,811 B1 | 8/2001 | Kasturi et al. |
| 6,372,708 B1 | 4/2002 | Kasturi et al. |
| 6,525,012 B2 | 2/2003 | Price et al. |
| 6,528,476 B1 | 3/2003 | Bodet et al. |
| 6,528,477 B2 | 3/2003 | Kasturi et al. |
| 6,573,234 B1 | 6/2003 | Sivik et al. |
| 6,579,839 B2 | 6/2003 | Price et al. |
| 6,645,925 B2 | 11/2003 | Sivik et al. |
| 6,656,900 B2 | 12/2003 | Sivik et al. |
| 6,827,234 B2 | 12/2004 | Nicolini |
| 6,827,795 B1 | 12/2004 | Kasturi et al. |
| 6,903,064 B1 | 6/2005 | Kasturi et al. |
| 7,241,729 B2 | 7/2007 | Sivik et al. |
| 2003/0087794 A1 | 5/2003 | Price et al. |
| 2005/0124738 A1 | 6/2005 | Sivik et al. |

FOREIGN PATENT DOCUMENTS

| | | | |
|---|---|---|---|
| AU | 9915322 | | 6/1999 |
| AU | 9933519 | | 10/1999 |
| CA | 2060042 | | 8/1992 |
| DE | 4323638 | | 1/1995 |
| DE | 19545630 | | 6/1997 |
| EP | 0013585 | | 7/1980 |
| EP | 77588 | | 4/1983 |
| EP | 173259 | | 3/1986 |
| EP | 0232092 | | 8/1987 |
| EP | 357976 | | 3/1990 |
| EP | 188350 | | 10/1990 |
| EP | 0410567 | | 1/1991 |
| EP | 0467472 | A2 * | 1/1992 |
| EP | 0494554 | | 7/1992 |
| EP | 0 509 109 | A1 | 10/1992 |
| EP | 0556650 | | 8/1993 |
| EP | 0560519 | | 9/1993 |
| EP | 560567 | | 9/1993 |
| GB | 1073947 | | 6/1967 |
| GB | 1541670 | | 10/1976 |
| GB | 2027045 | | 2/1980 |
| GB | 1584127 | | 2/1981 |
| GB | 2101091 | | 3/1983 |
| GB | 2104091 | A * | 3/1983 |
| GB | 2116568 | | 9/1983 |
| JP | 52-54034 | | 5/1977 |
| JP | 05214392 | | 3/1982 |
| JP | 58013700 | | 1/1983 |
| JP | 59135293 | | 8/1984 |
| JP | 61-152627 | A | 7/1986 |
| JP | 63-90521 | | 4/1988 |
| JP | 63-090521 | | 4/1988 |
| JP | 63196796 | A | 8/1988 |
| JP | 63-251409 | | 10/1988 |
| JP | 63-254115 | | 10/1988 |
| JP | 1-180813 | A | 7/1989 |
| JP | 2251696 | A | 10/1990 |
| JP | 04-500224 | | 1/1992 |
| JP | 4-227668 | A | 8/1992 |
| JP | 4-268305 | | 9/1992 |
| JP | 05-098595 | | 4/1993 |
| JP | 57044700 | | 8/1993 |
| JP | 5311194 | | 11/1993 |
| JP | 06-9726 | | 1/1994 |
| JP | 06-128337 | | 5/1994 |
| JP | 6-136311 | A | 5/1994 |
| JP | 7-503990 | A | 4/1995 |
| JP | 7-196455 | A | 8/1995 |
| JP | 11-079946 | | 3/1999 |
| JP | 11-79946 | | 3/1999 |
| JP | 11-505867 | T | 11/2010 |
| WO | 8101007 | | 4/1981 |
| WO | 9115524 | | 10/1991 |
| WO | 93/17057 | A1 | 9/1993 |
| WO | 9416679 | | 8/1994 |
| WO | 9500611 | | 1/1995 |
| WO | 9502674 | | 1/1995 |
| WO | 9519951 | | 7/1995 |
| WO | 9522311 | | 8/1995 |
| WO | 9602622 | | 2/1996 |
| WO | 9617916 | | 6/1996 |
| WO | 9637597 | | 11/1996 |
| WO | 9702337 | | 1/1997 |
| WO | 9729736 | | 8/1997 |
| WO | 9735549 | | 10/1997 |
| WO | 9801478 | | 1/1998 |
| WO | 9828393 | | 7/1998 |
| WO | 9832831 | | 7/1998 |
| WO | 9838973 | | 9/1998 |
| WO | 9839401 | | 9/1998 |
| WO | 9903894 | | 1/1999 |
| WO | 9922702 | | 5/1999 |
| WO | 9927053 | | 6/1999 |
| WO | 9927054 | | 6/1999 |
| WO | 9927057 | | 6/1999 |
| WO | 9927058 | | 6/1999 |
| WO | 0006102 | | 2/2000 |
| WO | 9637597 | A1 | 11/2010 |
| ZA | 6805954 | | 3/1969 |

OTHER PUBLICATIONS

J. Krstina, C. Moad, E. Rizzardo, *A New Form of Controlled Growth Free Radical Polymerization* Macromol. Symp. 111, p. 13-23 (1996).

S. Sandler, W. Karo, *Poly(Vinyl Ethers)*, Organic Chemistry, Polymer Syntheses vol. II, Academic Press N.Y., Chapter 7, p. 214-231 (1974).

V. Butun, N. Billingham, S. Armes, *Synthesis and Aqueous Solution Properties of Novel Hydrophilic-Hydrophilic Block Copolymers Based on Tertiary Amine Methacrylates*, Chem. Commun. 671-672 (1997).

S. Creutz, J. van Stam, F. De Schryver, R. Jerome, *Dynamics of Poly((dimethylamino)alkyl methacrylate-block-sodium Methacrylate) Micelles. Influences of hydrophobicity and Molecular Architecture on the Exchange Rate of Copolymer Molecules*, Macromolecules, 31, 681-689 (1998).

A. Lowe, N. Billingham, S. Armes, *Synthesis and Characterization of Zwitterionic Block Polymers*, Macromolecules, 31, 5991-5998 (1998).

D. Shipp, J.L. Wang, K. Matyjaszewski, *Synthesis of Acrylate and Methacrylate Block CoPolymers Using Atom Transfer Radical Polymerization*, Macromolecules, 31, 6005-6008 (1998).

X. Zhang, K. Matyjanzewaki, *Synthesis of Well Defined Amphilphilic Block Copolymers with 2 Dimethylaminoethyl Methacrylate by Controlled Radical Polymerization*, Macromolecules 32, 1763-1766 (1999).

N. Hoogeveen, M. Sohen Stuart, G. Fleer, *Novel Water-Soluble Block CoPolymers of Dimethylaminoethyl Methacrylate and Dihydroxypropyl Methacrylate*, Macromolecules Chem. Phys., 197, p. 2553-2554 (1996).

U.S. Appl. No. 09/702,084, filed Oct. 30, 2000 in the name of Sivik et al.

U.S. Appl. No. 09/699,522, filed Oct. 30, 2000 in the name of Sivik et al.

U.S. Appl. No. 09/979,563, filed Nov. 14, 2001 in the name of Kasturi et al.

U.S. Appl. No. 09/698,479, filed Oct. 30, 2000 in the name of Vance Bergeron et al.

Office action of May 29, 2005 from U.S. Appl. No. 09/698,479.

Office action issued by the USPTO dated Sep. 3, 2008 for U.S. Appl. No. 10/995,194 (Sivik et al.).

Office action issued by the USPTO dated Sep. 30, 2005 for U.S. Appl. No. 10/921,324 (now U.S. 7,241,729 to Sivik et al.).

Office action issued by the USPTO dated Jun. 12, 2008 for U.S. Appl. No. 09/698,479 (Bergeron et al.).

S. Creutz, P. Teyssie, R. Jerome, *Living Anionic Homopolymerization and Block Copolymerization of (Dimethylamino)ethyl Methacrylate*, Macromolecules, 30, p. 6-9 (1997).

Office Action issued by the USPTO dated Dec. 31, 2002 for U.S. Appl. No. 09/702,084 (Sivik et al.).

Office action of Mar. 29, 2005 from U.S. Appl. No. 09/698,479.

Office action of Feb. 3, 2005 from European patent application serial No. 00932781.8.

Supplementary European Search Report, Aug. 1, 2005, EP Application 00 93 6268.

Notice of Allowance of Apr. 7, 2010 from U.S. Appl. No. 09/698,479 to Bergeron et al.

Office Action mailed Jul. 8, 2010, in U.S. Appl. No. 10/995,194, Sivek et al.

Notice of Allowance mailed Aug. 25, 2010 in U.S. Appl. No. 09/698,479 to Bergeron et al.

Japanese office action mailed Jun. 15, 2010 from JP pat. app. No. 2001-619981 to Yeung et al.

Japanese office action mailed May 18, 2010 from JP pat. app. No. 2000-620033 to Bergeron et al.

Translation of Amendment of Nov. 7, 2010 in response to Japanese office action mailed May 18, 2010 from JP pat. app. No. 2000-620033 to Bergeron et al.

Translation of Amendment of Dec. 15, 2010 in response to Japanese office action mailed Jun. 15, 2010 from JP pat. app. No. 2000-619981 to Yeung et al.

Notice of Allowance mailed Dec. 23, 2010 in U.S. Appl. No. 09/698,479 to Bergeron et al.

\* cited by examiner

BLOCK POLYMERS, COMPOSITIONS AND METHODS OF USE FOR FOAMS, LAUNDRY DETERGENTS, SHOWER RINSES AND COAGULANTS

CROSS REFERENCE TO RELATED APPLICATION

This is a divisional of U.S. patent application Ser. No. 11/025,967 filed Jan. 3, 2005 which is a continuation of U.S. patent application Ser. No. 09/698,149 filed Oct. 30, 2000, incorporated herein by reference, which is a continuation in part of U.S. patent application Ser. No. 09/318,942 filed May 26, 1999, now abandoned, incorporated herein by reference. The claimed invention was made as a result of activities undertaken within the scope of a joint research agreement that was in effect on or before the date the claimed invention was made. Rhodia Inc. and The Procter & Gamble Co. are the parties to the joint research agreement.

FIELD OF THE INVENTION

The present invention relates to block polymers and compositions and methods of use of polymers in beauty care and personal care products, washing fabric articles, and other uses. More particularly, the block polymers suitable for use in the compositions and methods of the present invention comprise one or more cationic homopolymer and/or monomer units and optionally, one or more additional building blocks such as hydroxyl-containing units, hydrophobic group-containing units, hydrophilic group-containing units, anionic units, other cationic units, hydrogen bonding units, hydrogen bonding units and zwitterionic units. Preferably, the polymers have an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12.

The present invention further relates to compositions and methods for using oil well foam, fire-fighting foam, agrochemical foam, hard surface detergent foam, coagulant for titanium dioxide, shower rinse, and hard surface cleaner foam.

U.S. patent application Ser. No. 09/318,942, filed May 26, 1999, and Patent Cooperation Treaty application no. PCT/US00/14314, filed May 25, 2000, are both incorporated herein by reference in their entirety.

BACKGROUND OF THE INVENTION

Compositions for foam stabilizing, titanium dioxide coagulation and shower rinses are called upon to perform under difficult conditions.

For example liquid detergent compositions suitable for hand dishwashing must satisfy several criteria to be effective. These compositions must effectively cut grease and greasy food material and once removed, must keep the greasy material from re-depositing on the dishware.

The presence of suds in a hand dishwashing operation has long been used as a signal that the detergent continues to be effective. However, depending upon the circumstances, the presence of suds or the lack thereof, has no bearing upon the efficacy of liquid detergents. Therefore, the consumer has come to rely upon a somewhat erroneous signal, the lack or absence of soap suds, to indicate the need for additional detergent. In many instances the consumer is adding an additional amount of detergent far in excess of the amount necessary to thoroughly clean the dishes. This wasteful use of detergent is especially true in hand dishwashing since the soiled cooking articles are usually cleaned in a "washing difficulty" queue, for example, glasses and cups, which usually do not contact greasy food, are washed first, followed by plates and flatware, and finally pots and pans which contain the most residual food material and are usually, therefore, the "greasiest".

The lack of suds in the dishwater when pots and pans are usually cleaned, together with the visual inspection of the amount of residual food material on the cookware surface, typically compels the consumer to add additional detergent when a sufficient amount still remains in solution to effectively remove the soil and grease from the dishware or cookware surface. However, effective grease cutting materials do not necessarily produce a substantial amount of corresponding suds.

Accordingly, there remains a need in the art for liquid dishwashing detergents useful for hand washing dishware which have an enduring suds level while maintaining effective grease cutting properties. The need exists for a composition, which can maintain a high level of suds as long as the dishwashing composition is effective. Indeed, there is a long felt need to provide a hand dishwashing composition which can be use efficiently by the consumer such that the consumer uses only the necessary amount of detergent to fully accomplish the cleaning task. There is also a need for products in the laundry field for a product having improved grease and soil removal properties. There is also a need for products in the personal care field, particularly hand soaps, body washes, shampoos, shaving creams, shaving gels and dephiliatories, which have improved foam retention. There is also a need for improved oil well treating foam, agrochemical foam, fire-fighting foam, shower rinses and coagulants for $TiO_2$. There is also a need for improved oil well treating foam, agrochemical foam, and fire fighting foam. There is also a need for improved bathroom shower rinsing compositions, coagulants for titanium dioxide used in paper making, and hard surface cleaner foam.

SUMMARY OF THE INVENTION

The present invention meets the aforementioned needs in that it has been surprisingly discovered that polymeric block materials having the capacity to accommodate a positive charge character, negative charge character, or zwitterionic character have the capacity to provide liquid hand wash detergent compositions with extended suds volume and suds duration benefits.

A first aspect of the present invention relates to a block polymer comprising:
  i) one or more cationic group-containing units; and
  ii) optionally one or more additional building block units;
provided that the block polymer has an average cationic charge density of about 15 or less.

Another aspect relates to compositions, typically liquid detergent compositions, having increased suds/foam volume and suds/foam retention suitable for use in hand dishwashing or other uses, said compositions comprising:
  a) an effective amount of a block polymer comprising:
    i) one or more cationic group-containing units; and
    ii) optionally one or more additional building block units
  provided that the block polymer has an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12;
  b) an effective amount of a surfactant for the given use; and
  c) the balance carriers and other adjunct ingredients; provided that a 10% aqueous solution of said composition has a pH of from about 4 to about 12.

Typically, these compositions are granular solids or liquid. Moreover, for many of the purposes for which these compositions are intended, the surfactant comprises a detergent surfactant.

The present invention further relates to methods for providing increased suds/foam retention and suds volume when hand washing dishware or other uses involving suds/foam.

In still another aspect, the present invention provides methods and compositions for personal care, such as shampoos, soaps (hand washes and body washes), shaving cream, post foaming shaving gel, and dephiliatories, oil field foam, fire fighting foam, agrochemical foam, hard surface (e.g., bathroom tile) foam cleaner, shower rinse, fabric washing with improved soil release properties, and coagulants/retention aids for titanium dioxide used in paper processing.

These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

All substituent groups in structural formulas in the specification and claims have the meaning defined in previous structural formulas in the specification or claims, respectively, unless indicated otherwise.

Additional background is provided by Patent Cooperation Treaty patent application serial numbers PCT/US98/24853, PCT/US98/24707, PCT/US98/24699, and PCT/US98/24852, incorporated herein by reference in their entirety. Additionally, the polymers can be present as the free base or as a salt. Typical counter ions include acetate, citrate, maleate, sulfate, chloride, etc.

DETAILED DESCRIPTION OF THE INVENTION

The present invention relates to block polymeric materials (also termed "block polymeric enhancing agents"), which provide enhanced suds duration and enhanced suds volume when formulated into liquid detergent compositions suitable in the field of personal care, particularly for hand washing and/or body washing soaps or shampooing, as well as enhancing other properties in other uses. Among their other advantages, they also provide enhanced soil release for laundry detergents. The polymeric material preferably may comprise any material provided the final polymers have an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12.

The hand washing, body washing, shampoo, laundry detergent and other compositions of the present invention comprise:
  a) an effective amount of a block polymer effective as a suds stabilizer or soil release agent, or agent for another desired purpose said polymer comprising:
    i) one or more cationic group-containing units and, optionally, one or more additional building block groups;
  provided that said polymer has have an average cationic charge density of about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12;
  b) an effective amount of a surfactant, typically a detersive surfactant when the composition is used for cleaning; and
  c) the balance carriers and other adjunct ingredients appropriate to the particular use; provided that a 10% aqueous solution of said composition has a pH of from about 4 to about 12.

It is preferred that the polymer (a) further comprises at least
  (ii) one or more hydroxyl groups, provided that said polymer has a Hydroxyl Group Density of about 0.5 or less (more preferably about 0.0001 to about 0.4), and/or
  (iii) one or more units having one or more hydrophobe groups selected from the group consisting of non-hydroxyl groups, non-cationic groups, non-anionic groups, non-carbonyl groups, and/or non-H-bonding groups.

It is also preferred that the polymer (a) further comprises at least one of:
  units capable of having an anionic charge at a pH of from about 4 to about 12;
  units capable of having an anionic charge and a cationic charge at a pH of from about 4 to about 12; and
  units having no charge at a pH of from about 4 to about 12.

Block Polymers

"Block Polymers" as used herein is meant to encompass two or more different homopolymeric and/or monomeric units which are linked to form a single polymer molecule. Typically, the block polymers are in the form of di-, tri- and multi-block polymers. Those skilled in the art will recognize the phrase "block copolymers" is synonymous with this definition of "block polymers".

"Building Blocks" herein is meant homopolymeric units and/or monomeric units that polymerize with one another to form block copolymers. Nonlimiting examples of suitable building blocks in accordance with the present invention are cationic units, hydrogen-bonding units, hydrophilic units, hydrophobic units, anionic units and zwitterionic units. For the purposes of the present invention, the block polymer of the present invention comprises one or more cationic homopolymeric and/or monomeric units.

The different homopolymeric units present in block polymers retain some of their respective individual, original properties even though they are linked to one or more different homopolymeric units. Block polymers are known to exhibit properties that are different from those of homopolymers, random copolymers, and polymer blends but the properties of block copolymers themselves differ, depending on the length and chemical composition of the blocks making up the block polymer. Accordingly, the properties of a block polymer are influenced by the arrangement of the blocks within the block polymer. For example, a block polymer such as:
  hydrophobic block-hydrophilic block-hydrophobic block-cationic block will exhibit properties that are different than a block polymer such as:
  hydrophilic block-hydrophobic block-hydrophilic block-cationic block.

Likewise, a block polymer such as:
hydrophilic-hydrophilic-hydrophilic-hydrophilic-hydrophobic-hydrophilic-cationic will exhibit properties that are different than a block polymer such as:
cationic-hydrophilic-hydrophobic-hydrophilic.

Block Polymer Structures

The block polymers of the present invention comprise at least one cationic homopolymeric and/or monomeric unit, preferably 2-(dimethylaminoethyl)methacrylate (DMAM) and one or more non-cationic homopolymeric and/or monomeric units, such as acrylic acid (AA), methacrylic acid (MA), hydroxyethylacrylate (HEA), hydroxypropylacrylate (HPA), hydroxyethyl methacrylate (HEMA), hydroxypropyl methacrylate (HPMA), vinyl pyrrolidone, styrene, styrene sulfonate, vinyl acetate, maleic anhydride, and mixtures thereof, which among other suitable "building blocks" are described in more detail hereinafter.

Cationic Units

For the purposes of the present invention the term "cationic unit" is defined as "a moiety which when incorporated into the structure of the suds stabilizers of the present invention, is capable of maintaining a cationic charge within the pH range of from about 4 to about 12. The cationic unit is not required to be protonated at every pH value within the range of about 4 to about 12." Non-limiting examples of units which comprise a cationic moiety include the cationic units having the formula:

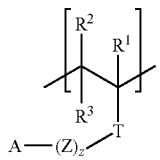
[I]

wherein each of $R^1$, $R^2$ and $R^3$ are independently selected from the group consisting of hydrogen, $C_1$ to $C_6$ alkyl, and mixtures thereof, preferably hydrogen, $C_1$ to $C_3$ alkyl, more preferably, hydrogen or methyl. T is selected from the group consisting of substituted or unsubstituted, saturated or unsaturated, linear or branched radicals selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, and carboalkoxy radicals and mixtures thereof. Z is selected from the group consisting of: $-(CH_2)-$, $(CH_2-CH=CH)-$, $-(CH_2-CHOH)-$, $(CH_2-CHNR^4)-$, $-(CH_2-CHR^5-O)-$ and mixtures thereof, preferably $-(CH_2)-$. $R^4$ and $R^5$ are selected from the group consisting of hydrogen, $C_1$ to $C_6$ alkyl and mixtures thereof, preferably hydrogen, methyl, ethyl and mixtures thereof; z is an integer selected from about 0 to about 12, preferably about 2 to about 10, more preferably about 2 to about 6. A is $NR^6R^7$ or $NR^6R^7R^8$. Wherein each of $R^6$, $R^7$ and $R^8$, when present, are independently selected from the group consisting of H, $C_1$-$C_8$ linear or branched alkyl, alkyleneoxy having the formula:

$$-(R^9O)_y R^{10}$$

wherein $R^9$ is $C_2$-$C_4$ linear or branched alkylene, and mixtures thereof; $R^{10}$ is hydrogen, $C_1$-$C_4$ alkyl, and mixtures thereof; y is from 1 to about 10. Preferably $R^6$, $R^7$ and $R^8$, when present, are independently, hydrogen, $C_1$ to $C_4$ alkyl. Alternatively, $NR^6R^7$ or $NR^6R^7R^8$ can form a heterocyclic ring containing from 4 to 7 carbon atoms, optionally containing additional hetero atoms, optionally fused to a benzene ring, and optionally substituted by $C_1$ to $C_6$ hydrocarbyl, and/or acetates. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred. Furthermore the block polymeric suds stabilizer has a molecular weight of from about 1,000 to about 2,000,000 preferably from about 5,000 to about 1,000,000, more preferably from about 10,000 to about 750,000, more preferably from about 20,000 to about 500,000, even more preferably from about 35,000 to about 300,000 daltons. The molecular weight of the block polymeric suds boosters, can be determined via conventional gel permeation chromatography or any other suitable procedure known to those of ordinary skill in the art.

Examples of the cationic unit of formula [I] include, but are not limited to, the following structures:

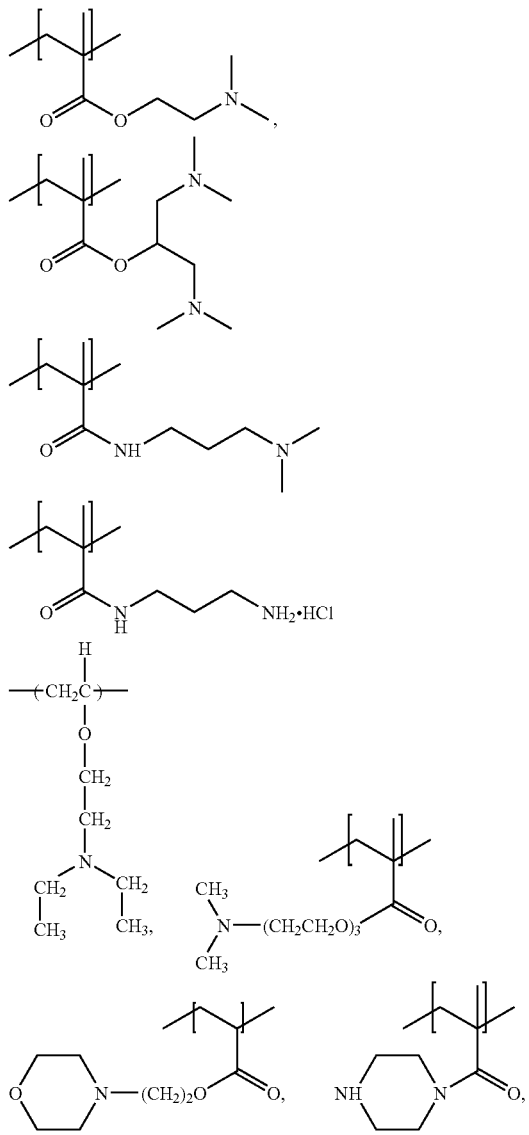

A preferred cationic unit is 2-dimethylaminoethyl methacrylate (DMAM) having the formula:

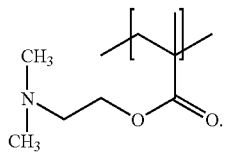

Building Blocks

Suitable building blocks for the block polymers of the present invention include, but are not limited to, amines, quaternized amines, ethoxylates, carboxylates, alkyls, aromatic rings, styrene, sulfonates, nitrates, ethylenically unsaturated monocarboxylic acids, ethylenically unsaturated dicarboxylic acids and mixtures thereof.

Examples of ethylenically unsaturated monocarboxylic acids as monomers that are useful in the present invention include, but are not limited to, acrylic acid, methacrylic acid, ethacrylic acid, crotonic acid, vinyllactic acid and mixtures thereof.

Examples of ethylenically unsaturated dicarboxylic acids as monomers that are useful in the present invention include, but are not limited to, maleic acid, fumaric acid, aconitic acid, itaconic acid, mesaconic acid, citraconic acid and methylenemalonic acid and mixtures thereof. Those skilled in the art will appreciate that the dicarboxylic acids can be replaced by their respective anhydrides where these exist.

Preferred carboxylic acid monomers for use in the present invention are substituted or unsubstituted acrylic and methacrylic acids wherein the substituent, when present, is selected from the group consisting of: hydrogen, amino groups, halogen groups, hydroxyl groups, monovalent alkyl radicals, monovalent aryl radicals, monovalent aralkyl radicals, monovalent alkaryl radicals, monovalent cycloaliphatic radicals and mixtures thereof.

Hydroxyl-Containing Units

One or more units having one or more hydroxyl groups may be incorporated into a block polymeric suds stabilizer/polymeric enhancing agent of the present invention The hydroxyl group density of a block polymeric suds stabilizer/polymeric enhancing agent of the present invention is determined by the following calculation.

$$\text{Hydroxyl Group Density} = \frac{\text{(Molecular Weight of Hydroxyl Group)}}{\text{(Total Monomer Molecular Weight)}}$$

wherein X represents the mole quantity of hydroxyl monomer in the block polymeric suds stabilizer.

For example, the Hydroxyl Group Density of a block polymeric suds stabilizer/polymeric enhancing agent containing 2-dimethylaminoethyl methacrylate having a molecular weight of approximately 157 and hydroxyethylacrylate having a molecular weight of approximately 116 grams/mole, at a 1:3 mole ratio would be calculated as follows:

$$\text{Hydroxyl Group Density} = \left(\frac{17}{(3(116) + 157)}\right) = 0.0337$$

Preferably, the polymers of the present invention have a hydroxyl group density of about 0.5 or less, more preferably from about 0.0001 to about 0.4. This is especially preferable for use of these polymers as suds/foam stabilizers.

Nonlimiting examples of such hydroxyl group-containing units include, but are not limited to the following:

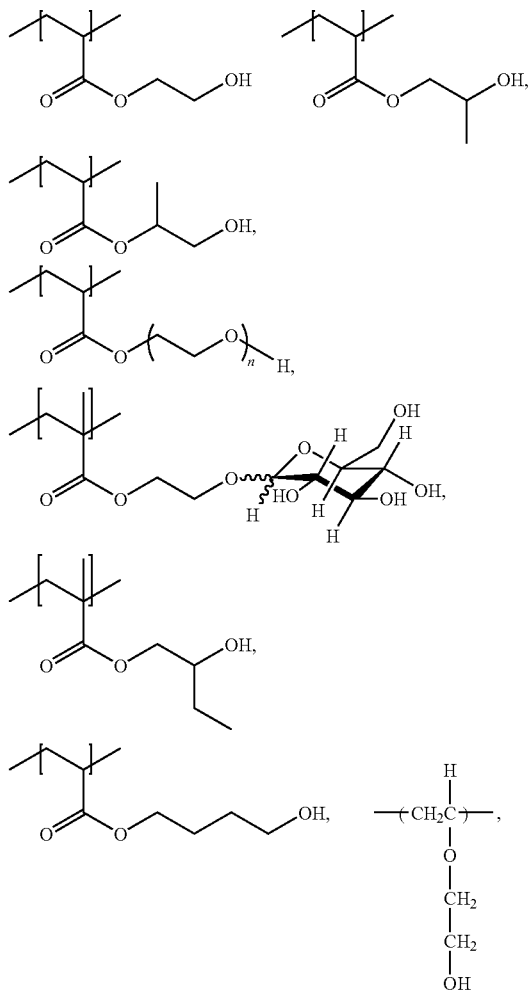

wherein n is an integer from 2 to 100, preferably 2 to 50, more preferably 2 to 30.

Hydrophobic Units

Suitable hydrophobic group-containing units for use in the present invention include, but are not limited to, hydrophobic groups preferably selected from the group consisting of non-hydroxyl groups, non-cationic groups, non-anionic groups, non-carbonyl groups, and/or non-H-bonding groups, more preferably selected from the group consisting of alkyls, cycloalkyls, aryls, alkaryls, aralkyls and mixtures thereof.

Nonlimiting examples of such hydrophobic group-containing units include, but are not limited to the following:

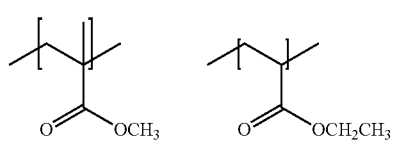

-continued

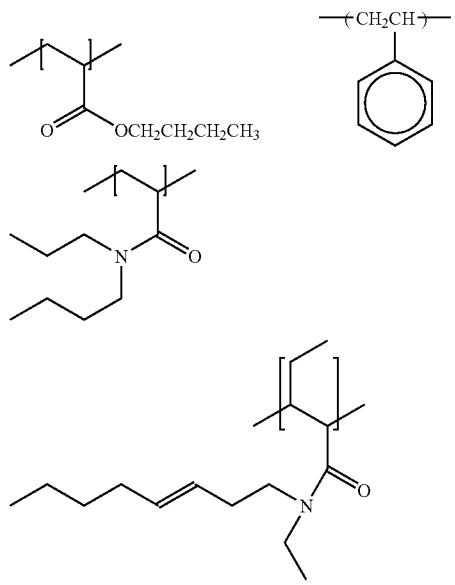

and a monomeric unit having the formula:

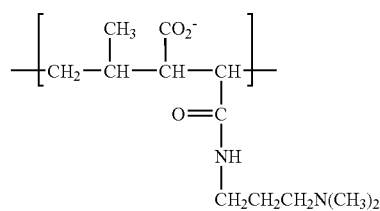

the latter of which also comprises a moiety capable of having a cationic charge at a pH of about 4 to about 12. This latter unit is defined herein as "a unit capable of having an anionic and a cationic charge at a pH of from about 4 to about 12."

Non-Charged Units

For the purposes of the present invention the term "non-charged unit" is defined as "a moiety which when incorporated into the structure of the suds stabilizers/polymeric enhancing agents of the present invention, has no charge within the pH range of from about 4 to about 12." Non-limiting examples of units which are "non-charged units" are monomers, such as styrene, ethylene, propylene, butylene, 1,2-phenylene, esters, amides, ketones, ethers, and the like.

The units which comprise the polymers of the present invention may, as single units or monomers, have any $pK_a$ value. The polymers may optionally be crosslinked.

Particular Block Polymers

Preferred block polymers comprising a homopolymer block of monomeric units A and at least one of a homopolymer block of monomeric units B and a homopolymer block of monomeric units C.

A. at least one cationic monomeric unit A having a Formula I:

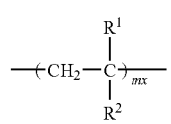

wherein
$R^1$ is H or an alkyl having 1 to 10 carbon atoms,
$R^2$ is a moiety selected from the group consisting of Hydrophilic Units Suitable hydrophilic group-containing units for use in the present invention include, but are not limited to, hydrophilic groups preferably selected from the group consisting of carboxyl groups, carboxylic acids and their salts, sulfonic acids and their salts, heteroatom-containing moieties present in a ring or linear form and mixtures thereof.

Nonlimiting examples of such hydrophilic group-containing units include, but are not limited to the following:

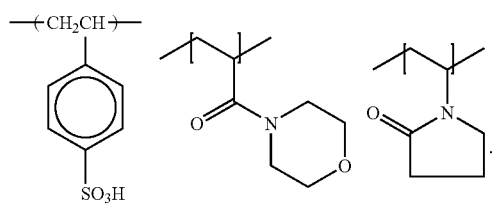

Anionic Units

For the purposes of the present invention, the term "anionic unit" is defined as "a moiety which when incorporated into the structure of the suds stabilizers/block polymeric enhancing agents of the present invention, is capable of maintaining an anionic charge within the pH range of from about 4 to about 12. The anionic unit is not required to be de-protonated at every pH value within the range of about 4 to about 12." Non-limiting examples of units which comprise an anionic moiety include, acrylic acid, methacrylic acid, glutamic acid, aspartic acid, a monomeric unit having the formula:

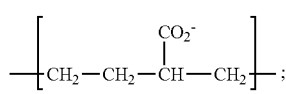

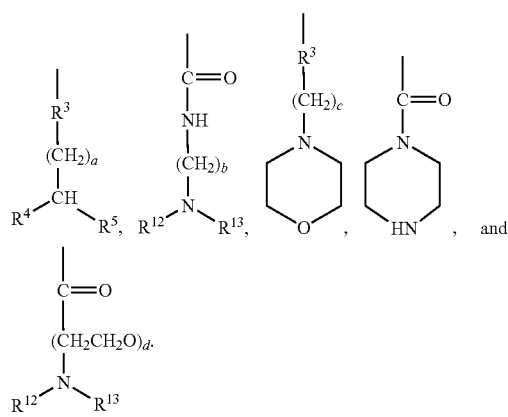

wherein $R^3$ is selected from the group consisting of $$-O-, \quad -\overset{\overset{O}{\|}}{C}-, \quad \text{and} \quad -\overset{\overset{O}{\|}}{C}-O-;$$

a is an integer from 0 to 16, preferably 0 to 10;
b is an integer from 2 to 10;
c is an integer from 2 to 10;
d is an integer from 1 to 100;

$R^4$ and $R^5$ are independently selected from the group consisting of —H, and $$-R^8-N\overset{R^9}{\underset{R^{10}}{\diagup}};$$

$R^8$ is independently selected from the group consisting of a bond and an alkylene having 1 to 18, preferably 1 to 10, carbon atoms;

$R^9$ and $R^{10}$ are independently selected from the group consisting of —H, alkyl having 1 to 10, preferably 1 to 8 carbon atoms;

$R^{12}$ and $R^{13}$ are independently selected from the group consisting of H and alkyl having from 1 to 10, preferably 1 to 8 carbon atoms;

[structure: piperazine-like with (CH2)t-morpholine]

wherein t is an integer from 2 to 10;

B. at least one monomeric unit B selected from the group consisting of:
a monomeric unit of Formula IV $$-(CH_2-\underset{\underset{R^{21}}{|}}{\overset{\overset{R^{20}}{|}}{C}})_{nx}-$$

IV wherein $R^{20}$ is selected from the group consisting of H and $CH_3$;

$R^{21}$ is selected from the group consisting of:

[morpholine-N-C=O structure], [pyrrolidinone-N-CH2CH2- structure], $-O-\overset{\overset{O}{\|}}{C}-CH_3$, —OH, $-\overset{\overset{O}{\|}}{C}-OH$, $-\overset{\overset{O}{\|}}{C}-O-(CH_2)_e-OH,$ wherein e is an integer from 3 to 25, preferably 3 to 5, $-O-(CH_2)_f-CH_3$ wherein f is an integer from 0 to 25, preferably 0 to 12;

$$-\overset{\overset{O}{\|}}{C}-O-(\overset{\overset{R^{23}}{|}}{C}HCH_2O)_g-H, \quad -\overset{\overset{O}{\|}}{C}-O-(CH_2\overset{\overset{R^{24}}{|}}{C}HO)_h-H,$$

wherein g is an integer from 1 to 100 preferably 1 to 50;
h is an integer from 1 to 100, preferably 1 to 50;
$R^{23}$ is —H, —$CH_3$ or —$C_2H_5$,
$R^{24}$ is —CH, or —$C_2H_5$;

$$-\overset{\overset{O}{\|}}{C}-NH-(CH_2)_j-OH$$

wherein j is an integer from 1 to 25, preferably 2 to 12;

$$-\overset{\overset{O}{\|}}{C}-NH-CH_2-\overset{\overset{CH_3}{|}}{C}H-OH;$$

[sugar/glycoside structure with $-(CH_2)_k-$ linker]

wherein k is an integer from 1 to 25, preferably 1 to 12;

[para-substituted benzene with $SO_3H$];

—NH—$(CH_2)_m$—$NH_2$·HCl, wherein m is an integer from 1 to 25, preferably 2 to 12; and a polyhydroxy monomeric unit of Formula VI:

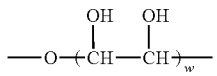

VI wherein w is an integer from 1 to 50, preferably 1 to 25; and

C. optionally at least one monomeric unit C selected from the group consisting of:

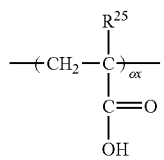

wherein $R^{25}$ is —H or —$CH_3$,

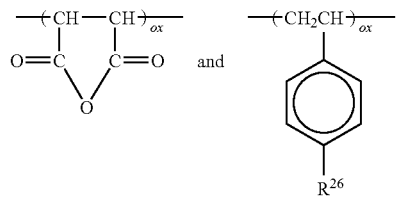

wherein $R^{26}$ is —H or $CH_3$;

x represents the total number of monomeric units within the bock polymer; m, n, o, when present, represent the mole ratio of their respective monomeric units in a given block polymer, wherein at least two different monomeric units are present in the block polymer.

Preferably m, n and o are each greater than 1.

A preferred block polymer, comprising three or more homopolymeric and/or monomeric units, comprises at least one said monomeric unit A, at least one said monomeric unit B and at least one said monomeric unit C.

Preferably, at least one monomeric unit A is selected from the group consisting of:

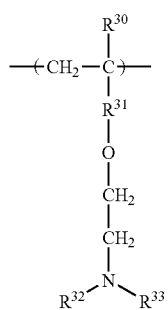

wherein $R^{30}$ is H or —$CH_3$, wherein $R^{31}$ is a bond or

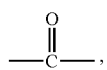

and $R^{32}$ and $R^{33}$ are —$CH_3$ or —$C_2H_5$.

Preferably, the block polymer is a terpolymer in which:

said at least one monomeric unit B is selected from the group consisting of:

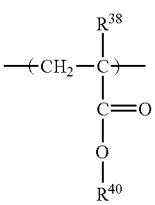

wherein $R^{38}$ is selected from the group consisting of H and $CH_3$ and $R^{40}$ is selected from the group consisting of —$CH_2CH_2$—OH and

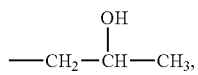

and isomers thereof.

More preferably, said terpolymer comprises said at least one monomeric unit C, wherein the molar ratio of said monomeric unit A:monomeric unit B:monomeric unit C is 1 to 9:1 to 9:1 to 6 respectively.

Preferably, the block polymer has at least one monomeric unit B has the formula:

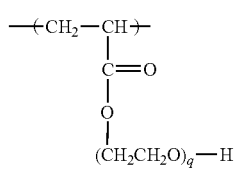

wherein q ranges from 1 to 12, preferably 1 to 10, more preferably 1 to 9.

Preferably, the block polymer is a terpolymer, in which at least one monomeric unit A is selected from the group consisting of:

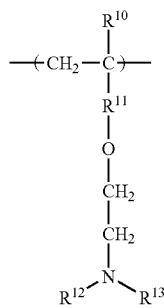

wherein $R^{10}$ is H or $CH_3$,
$R^{11}$ is a bond or

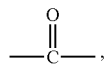

and $R^{12}$ and $R^{13}$ are —$CH_3$ or —$C_2H_5$, and said polymer comprises said at least one monomeric unit C.

Preferably, the molar ratio of cationic monomeric unit A:monomeric unit B:monomeric unit C ranges from 1 to 9:1 to 9:1 to 3 respectively.

Typically, monomeric unit A has a formula selected from the group consisting of:

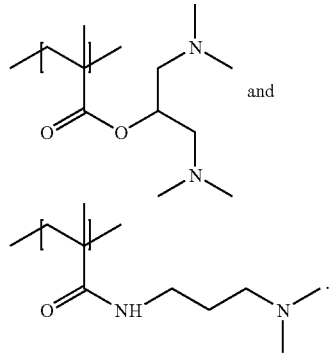

Preferably, at least one cationic monomeric unit A has a formula selected from the group consisting of:

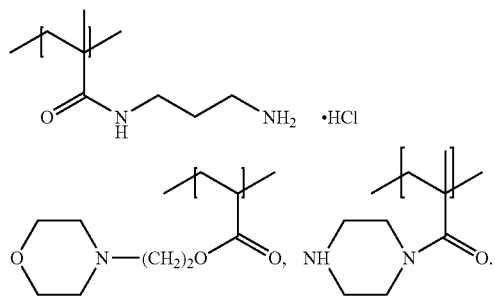

Preferably, at least one monomeric unit B is selected from the group consisting of:

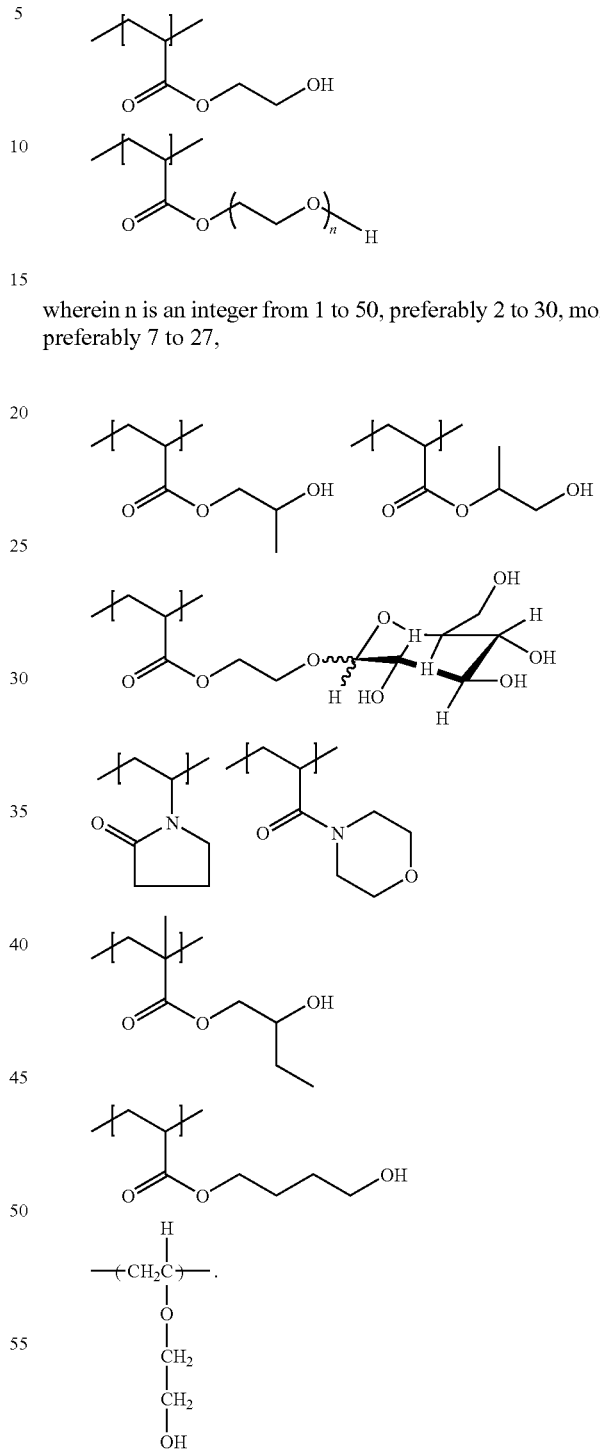

wherein n is an integer from 1 to 50, preferably 2 to 30, more preferably 7 to 27, Proteinaceous Suds Stabilizers The proteinaceous suds stabilizers of the present invention can be peptides, polypeptides, amino acid containing copolymers, terpolymers etc., and mixtures thereof. Any suitable amino acid can be used to form the backbone of the peptides, polypeptides, or amino acid.

In general, the amino acids suitable for use in forming the proteinaceous suds stabilizers of the present invention have the formula:

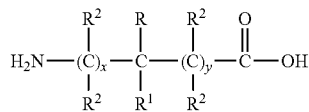

wherein R and $R^1$ are each independently hydrogen, $C_1$-$C_6$ linear or branched alkyl, $C_1$-$C_6$ substituted alkyl, and mixtures thereof. Non-limiting examples of suitable moieties for substitution on the $C_1$-$C_6$ alkyl units include amino, hydroxy, carboxy, amido, thio, thioalkyl, phenyl, substituted phenyl, wherein said phenyl substitution is hydroxy, halogen, amino, carboxy, amido, and mixtures thereof. Further non-limiting examples of suitable moieties for substitution on the R and $R^1$ $C_1$-$C_6$ alkyl units include 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, and mixtures thereof. Preferably $R^1$ is hydrogen and at least 10% of R units are moieties which are capable of having a positive or negative charge at a pH of from about 4 to about 12. Each $R^2$ is independently hydrogen, hydroxy, amino, guanidino, $C_1$-$C_4$ alkyl, or comprises a carbon chain which can be taken together with R, $R^1$ any $R^2$ units to form an aromatic or non-aromatic ring having from 5 to 10 carbon atoms wherein said ring may be a single ring or two fused rings, each ring being aromatic, non-aromatic, or mixtures thereof. When the amino acids according to the present invention comprise one or more rings incorporated into the amino acid backbone, then R, $R^1$, and one or more $R^2$ units will provide the necessary carbon-carbon bonds to accommodate the formation of said ring. Preferably when R is hydrogen, $R^1$ is not hydrogen, and vice versa; preferably at least one $R^2$ is hydrogen. The indices x and y are each independently from 0 to 2.

An example of an amino acid according to the present invention which contains a ring as part of the amino acid backbone is 2-aminobenzoic acid (anthranilic acid) having the formula:

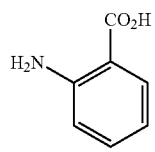

wherein x is equal to 1, y is equal to 0 and R, $R^1$, and 2 $R^2$ units from the same carbon atom are taken together to form a benzene ring.

A further example of an amino acid according to the present invention which contains a ring as part of the amino acid backbone is 3-aminobenzoic acid having the formula:

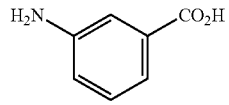

wherein x and y are each equal to 1, R is hydrogen and $R^1$ and four $R^2$ units are taken together to form a benzene ring.

Non-limiting examples of amino acids suitable for use in the proteinaceous suds stabilizers of the present invention wherein at least one x or y is not equal to 0 include 2-aminobenzoic acid, 3-aminobenzoic acid, 4-aminobenzoic acid, -alanine, and -hydroxyaminobutyric acid.

The preferred amino acids suitable for use in the proteinaceous suds stabilizers of the present invention have the formula:

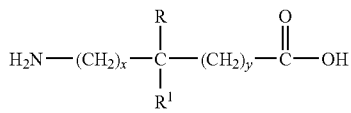

wherein R and $R^1$ are independently hydrogen or a moiety as describe herein above preferably $R^1$ is hydrogen and R comprise a moiety having a positive charge at a pH of from about 4 to about 12 wherein the polymers have an average cationic charge density from about 0.1 to about 2.75 units per 100 daltons molecular weight at a pH of from about 4 to about 12.

More preferred amino acids which comprise the proteinaceous suds stabilizers of the present invention have the formula:

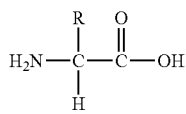

wherein R hydrogen, $C_1$-$C_6$ linear or branched alkyl, $C_1$-$C_6$ substituted alkyl, and mixtures thereof. R is preferably $C_1$-$C_6$ substituted alkyl wherein preferred moieties which are substituted on said $C_1$-$C_6$ alkyl units include amino, hydroxy, carboxy, amido, thio, $C_1$-$C_4$ thioalkyl, 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, phenyl, substituted phenyl, wherein said phenyl substitution is hydroxy, halogen, amino, carboxy, and amido.

An example of a more preferred amino acid according to the present invention is the amino acid lysine having the formula:

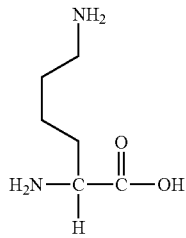

wherein R is a substituted $C_1$ alkyl moiety, said substituent is 4-imidazolyl.

Non-limiting examples of preferred amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and mixtures thereof. The aforementioned amino acids are typically referred to as the "primary-amino acids". However, the proteinaceous suds stabilizers of the present invention may typically comprise any amino acid having an R unit which together with the aforementioned amino acids serves to adjust the cationic charge density of the proteinaceous suds stabilizers to a range of from about 15 or less, preferably 5 or less, more preferably from about 0.05 to about 5, even more preferably from about 0.05 to about 2.77, even more preferably from about 0.1 to about 2.75, most preferably from about 0.75 to about 2.25 units per 100 daltons molecular weight at a pH of from about 4 to about 12.

For example, further non-limiting examples of amino acids include homoserine, hydroxyproline, norleucine, norvaline, ornithine, penicillamine, and phenylglycine, preferably ornithine. R units preferably comprise moieties which are capable of a cationic or anionic charges within the range of pH from about 4 to about 12. Non-limiting examples of preferred amino acids having anionic R units include glutamic acid, aspartic acid, and -carboxyglutamic acid.

For the purposes of the present invention, both optical isomers of any amino acid having a chiral center serve equally well for inclusion into the backbone of the peptide, polypeptide, or amino acid copolymers. Racemic mixtures of one amino acid may be suitably combined with a single optical isomer of one or more other amino acids depending upon the desired properties of the final proteinaceous suds stabilizer. The same applies to amino acids capable of forming diasteriomeric pairs, for example, threonine.

Non-limiting examples of suitable proteinaceous suds stabilizers are described by PCT International Application Serial No. PCT/US98/24707, incorporated herein by reference in its entirety.

Polyamino Acid Proteinaceous Suds Stabilizer

One type of suitable proteinaceous suds stabilizer according to the present invention is comprised entirely of the amino acids described herein above. Said polyamino acid compounds may be naturally occurring peptides, polypeptides, enzymes, and the like. An example of a polyamino acid which is suitable as a proteinaceous suds stabilizer according to the present invention is the enzyme lysozyme.

An exception may, from time to time, occur in the case where naturally occurring enzymes, proteins, and peptides are chosen as proteinaceous suds stabilizers.

Another class of suitable polyamino acid compound is the synthetic peptide having a molecular weight of at least about 1500 daltons. An example of a polyamino acid synthetic peptide suitable for use as a proteinaceous suds stabilizer according to the present invention is the copolymer of the amino acids lysine, alanine, glutamic acid, and tyrosine having an average molecular weight of 52,000 daltons and a ratio of lys:ala:glu:tyr of approximately 5:6:2:1.

Without wishing to be limited by theory, the presence of one or more cationic amino acids, for example, histidine, ornithine, lysine and the like, is required to insure increased suds stabilization and suds volume. However, the relative amount of cationic amino acid present, as well as the average cationic charge density of the polyamino acid, are key to the effectiveness of the resulting material. For example, poly L-lysine having a molecular weight of approximately 18,000 daltons comprises 1.00% amino acids which have the capacity to possess a positive charge in the pH range of from about 4 to about 12, with the result that this material is ineffective as a suds extender and as a greasy soil removing agent.

Peptide Copolymers

Another class of materials suitable for use as proteinaceous suds stabilizers according to the present invention are peptide copolymers. For the purposes of the present invention "peptide copolymers" are defined as "polymeric materials with a molecular weight greater than or equal to about 1500 daltons wherein at least about 100% by weight of said polymeric material comprises one or more amino acids".

Peptide copolymers suitable for use as proteinaceous suds stabilizers may include segments of polyethylene oxide which are linked to segments of peptide or polypeptide to form a material which has increased suds retention as well as formulatability.

Nonlimiting examples of amino acid copolymer classes include the following.

Polyalkyleneimine copolymers comprise random segments of polyalkyleneimine, preferably polyethyleneimine, together with segments of amino acid residues. For example, tetraethylenepentamine is reacted together with polyglutamic acid and polyalanine to form a copolymer having the formula:

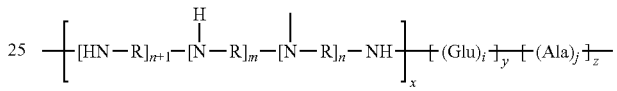

wherein m is equal to 3, n is equal to 0, i is equal to 3, j is equal to 5, x is equal to 3, y is equal to 4, and z is equal to 7.

However, the formulator may substitute other polyamines for polyalkyleneimines, for example, polyvinyl amines, or other suitable polyamine which provides for a source of cationic charge at a pH of from 4 to about 12.

The formulator may combine non-amine polymers with protonatable as well as non-protonatable amino acids. For example, a carboxylate-containing homo-polymer may be reacted with one or more amino acids, for example, histidine and glycine, to form an amino acid containing amido copolymer having the formula:

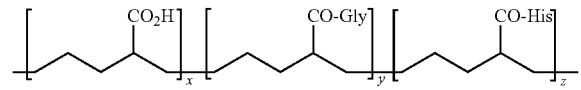

wherein said copolymer has a molecular weight of at least 1500 daltons and a ratio of x:y:z of approximately 2:3:6.

Zwitterionic Polymers

The polymeric suds stabilizer/soil release agents of the present invention are homopolymers or copolymers wherein the monomers which comprise said homopolymers or copolymers contain a moiety capable of being protonated at a pH of from about 4 to about 12, or a moiety capable of being de-protonated at a pH of from about 4 to about 12, of a mixture of both types of moieties.

A Preferred class of zwitterionic polymer suitable for use as a suds volume and suds duration enhancer has the formula:

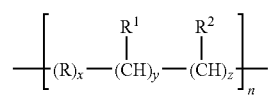

wherein R is $C_1$-$C_{12}$ linear alkylene, $C_1$-$C_{12}$ branched alkylene, and mixtures thereof; preferably $C_1$-$C_4$ linear alkylene, $C_3$-$C_4$ branched alkylene; more preferably methylene and 1,2-propylene. The index x is from 0 to 6; y is 0 or 1; z is 0 or 1.

The index n has the value such that the zwitterionic polymers of the present invention have an average molecular weight of from about 1,000 to about 2,000,000 preferably from about 5,000 to about 1,000,000, more preferably from about 10,000 to about 750,000, more preferably from about 20,000 to about 500,000, even more preferably from about 35,000 to about 300,000 daltons. The molecular weight of the polymeric suds boosters, can be determined via conventional gel permeation chromatography.

Non-limiting examples of suitable zwitterionic polymer are described in PCT International Application Serial No. PCT/US98/24699, incorporated herein by reference in its entirety.

Anionic Units $R^1$ is a unit capable of having a negative charge at a pH of from about 4 to about 12. Preferred $R^1$ has the formula:

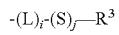

wherein L is a linking unit independently selected from the following:

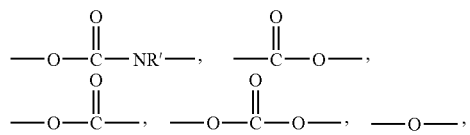

and mixtures thereof, wherein R' is independently hydrogen, $C_1$-$C_4$ alkyl, and mixtures thereof; preferably hydrogen or alternatively R' and S can form a heterocycle of 4 to 7 carbon atoms, optionally containing other hetero atoms and optionally substituted. Preferably the linking group L can be introduced into the molecule as part of the original monomer backbone, for example, a polymer having L units of the formula:

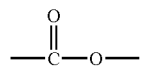

can suitably have this moiety introduced into the polymer via a carboxylate containing monomer, for example, a monomer having the general formula:

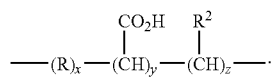

When the index i is 0, L is absent.

For anionic units S is a "spacing unit" wherein each S unit is independently selected from $C_1$-$C_{12}$ linear alkylene, $C_1$-$C_{12}$ branched alkylene, $C_3$-$C_{12}$ linear alkenylene, $C_3$-$C_{12}$ branched alkenylene, $C_3$-$C_{12}$ hydroxyalkylene, $C_4$-$C_{12}$ dihydroxyalkylene, $C_6$-$C_{10}$ arylene, $C_8$-$C_{12}$ diallylarylene, —$(R^5O)_kR^5$—, —$(R^5O)_kR^6(OR^5)_k$—, —$CH_2CH(OR^7)CH_2$—, and mixtures thereof; wherein $R^5$ is $C_2$-$C_4$ linear alkylene, $C_3$-$C_4$ branched alkylene, and mixtures thereof, preferably ethylene, 1,2-propylene, and mixtures thereof more preferably ethylene; $R^6$ is $C_2$-$C_{12}$ linear alkylene, and mixtures thereof preferably ethylene; $R^7$ is hydrogen, $C_1$-$C_4$ alkyl, and mixtures thereof, preferably hydrogen. The index k is from 1 to about 20.

Preferably S is $C_1$-$C_{12}$ linear alkylene, —$(R^5O)_kR^5$—, and mixtures thereof. When S is a —$(R^5O)_kR^5$— unit, said units may be suitably formed by the addition an alkyleneoxy producing reactant (e.g. ethylene oxide, epichlorohydrin) or by addition of a suitable polyethyleneglycol. More preferably S is $C_2$-$C_4$ linear alkylene. When the index j is 0 the S unit is absent.

$R^3$ is independently selected from hydrogen, —$CO_2M$, —$SO_3M$, —$OSO_3M$, —$CH_2P(O)(OM)_2$, —$OP(O)(OM)_2$, units having the formula:

wherein each $R^8$, $R^9$, and $R^{10}$ is independently selected from the group consisting of hydrogen, —$(CH_2)_mR^{11}$, and mixtures thereof, wherein $R^{11}$ is —$CO_2H$, —$SO_3M$, —$OSO_3M$, —$CH(CO_2H)CH_2CO_2H$, —$CH_2P(O)(OH)_2$, —$OP(O)(OH)_2$, and mixtures thereof, preferably —$CO_2H$, —$CH(CO_2)CH_2CO_2H$, and mixtures thereof more preferably —$CO_2H$; provided that one $R^8$, $R^9$, or $R^{10}$ is not a hydrogen atom, preferably two $R^8$, $R^9$, or $R^{10}$ units are hydrogen. M is hydrogen or a salt forming cation, preferably hydrogen. The index m has the value from 0 to 10.

Cationic Units $R^2$ is a unit capable of having a positive charge at a pH of from about 4 to about 12. Preferred $R^2$ has the formula:

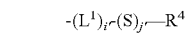

wherein $L^1$ is a linking unit independently selected from the following:

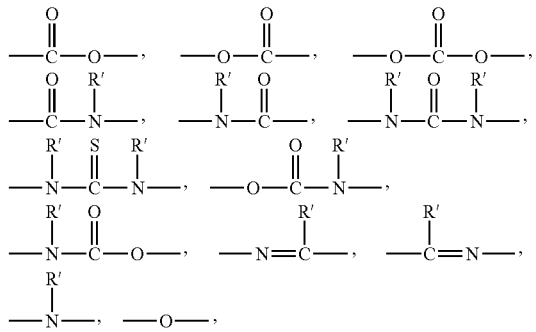

and mixtures thereof; wherein R' is independently hydrogen, $C_1$-$C_4$ alkyl, and mixtures thereof; preferably hydrogen or alternatively R' and S can form a heterocycle of 4 to 7 carbon atoms, optionally containing other hetero atoms and optionally substituted. Preferably $L^1$ has the formula:

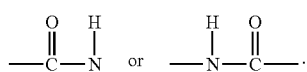

When the index i' is equal to 0, $L^1$ is absent.

For cationic units S is a "spacing unit" wherein each S unit is independently selected from $C_1$-$C_{12}$ linear alkylene, $C_1$-$C_{12}$ branched alkylene, $C_3$-$C_{12}$ linear alkenylene, $C_3$-$C_{12}$ branched alkenylene, $C_3$-$C_{12}$ hydroxyalkylene, $C_4$-$C_{12}$ dihydroxyalkylene, $C_6$-$C_{10}$ arylene, $C_8$-$C_{12}$ dialkylarylene, —$(R^5O)_kR^5$—, —$(R^5O)_kR^6(OR^5)_k$—, —$CH_2CH(OR^7)CH_2$—, and mixtures thereof; wherein $R^5$ is $C_2$-$C_4$ linear alkylene, $C_3$-$C_4$ branched alkylene, and mixtures thereof, preferably ethylene, 1,2-propylene, and mixtures thereof, more preferably ethylene; $R^6$ is $C_2$-$C_{12}$ linear alkylene, and mixtures thereof, preferably ethylene; $R^7$ is hydrogen, $C_1$-$C_4$ alkyl, and mixtures thereof, preferably hydrogen. The index k is from 1 to about 20.

Preferably S is $C_1$-$C_{12}$ linear alkylene, and mixtures thereof. Preferably S is $C_2$-$C_4$ linear alkylene. When the index j' is 0 the S unit is absent.

$R^4$ is independently selected from amino, alkylamino carboxamide, 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, and mixtures thereof, preferably dialkylamino having the formula:

wherein each $R^{11}$ is independently hydrogen, $C_1$-$C_4$ alkyl, and mixtures thereof, preferably hydrogen or methyl or alternatively the two $R^{11}$ can form a heterocycle of 4 to 8 carbon atoms, optionally containing other hetero atoms and optionally substituted.

An example of a preferred zwitterionic polymer according to the present invention has the formula:

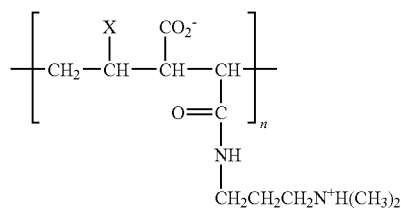

wherein X is $C_6$, n has a value such that the average molecular weight is from about 1,000 to about 2,000,000.

Further preferred zwitterionic polymers according to the present invention are polymers comprising monomers wherein each monomer has only cationic units or anionic units, said polymers have the formula:

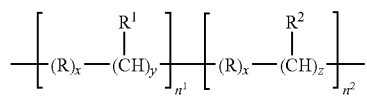

wherein R, $R^1$, x, y, and z are the same as defined herein above; $n^1+n^2=n$ such that n has a value wherein the resulting zwitterionic polymer has a molecular weight of form about 1,000 to about 2,000,000 daltons.

An example of a polymer having monomers with only an anionic unit or a cationic unit has the formula:

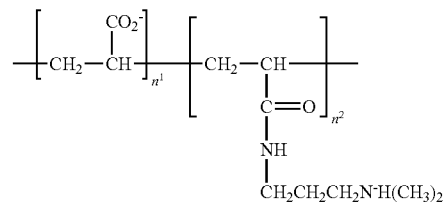

wherein the sum of $n^1$ and $n^2$ provide a polymer with an average molecular weight of from about 1,000 to about 2,000,000 daltons.

Another preferred zwitterionic polymer according to the present invention are polymers which have limited crosslinking, said polymers having the formula:

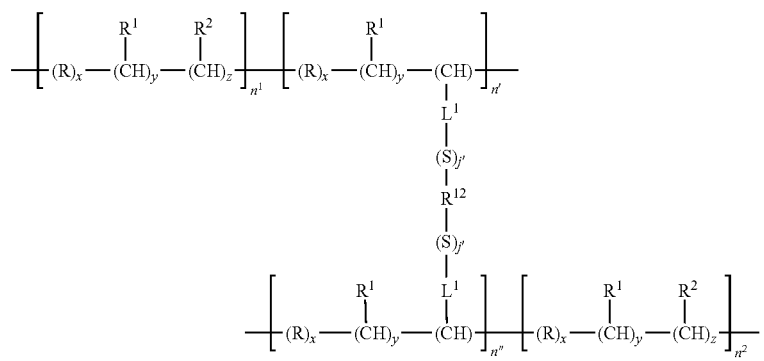

wherein R, $R^1$, $L^1$, S, j', x, y, and z are the same as defined herein above; n' is equal to n", and the value n'+n" is less than or equal to 5% of the value of $n^1+n^2=n$; n provides a polymer with an average molecular weight of from about 1,000 to about 2,000,000 daltons. $R^{12}$ is nitrogen $C_1$-$C_{12}$ linear alkylene amino alkylene having the formula:

$$-R^{13}-N-R^{13}-$$

$L^1$, and mixtures thereof, wherein each $R^{13}$ is independently $L^1$ or ethylene.

The zwitterionic polymers of the present invention may comprise any combination of monomer units, for example, several different monomers having various $R^1$ and $R^2$ groups can be combined to form a suitable suds stabilizer. Alternatively the same $R^1$ unit may be used with a selection of different $R^2$ units and vice versa.

Specific Block Polymers

Suitable examples of the block polymers of the present invention include, but are not limited to, the following:

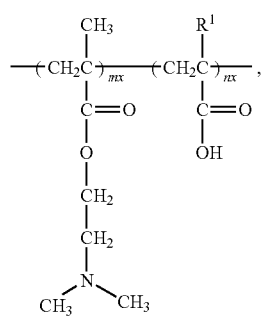

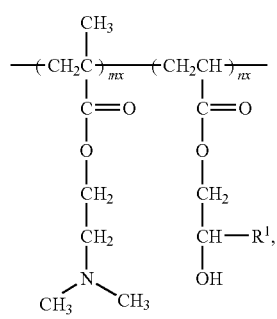

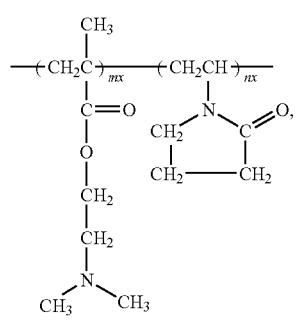

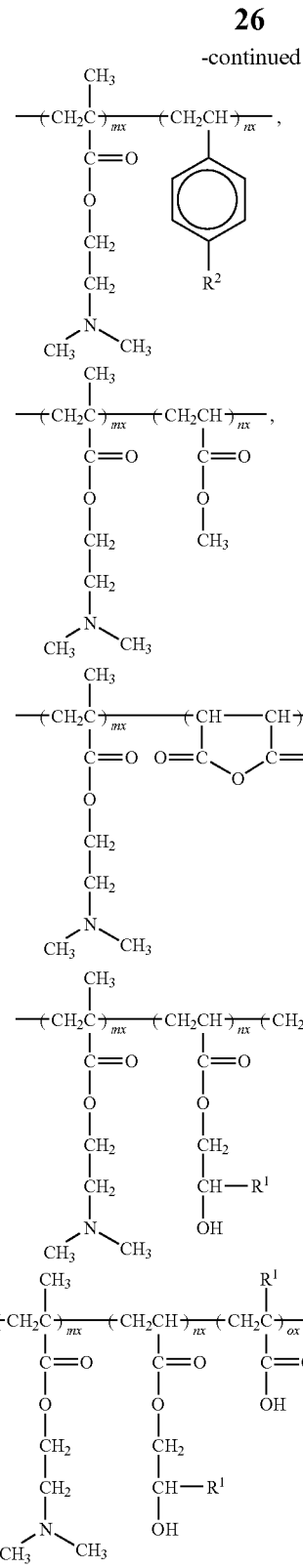

wherein $R^1$ is selected from H and $CH_3$; $R^2$ is selected from H and $SO_3H$; x represents the total number of monomer units within the block polymer; m, n, o, p, q, . . . , when present, represent the mole ratio of their respective monomeric units in a given block polymer where at least two different monomeric units are present in the block polymer. The block polymers of the present invention can comprise the each individual monomeric unit at a mole percent from about 0.01% to about 99.99% such that the mole percent of the monomeric units totals 100%. Preferably, the block polymers of the present invention preferably comprise about 30%, more preferably about 25% by mole of the dimethylaminoethyl methacrylate monomeric unit.

In a preferred embodiment wherein the block polymer is a di-block polymer comprising DMAM and a non-DMAM monomeric unit, preferably HEA or HPA, the preferred mole ratio of DMAM to non-DMAM monomeric unit is 1:3.

In another preferred embodiment wherein the block polymer is a tri-block polymer comprising DMAM, one non-DMAM monomeric unit, such as HEA, and a different non-DMAM monomeric unit, such as MA, the preferred mole ratio of DMAM to HEA to MA is 3:9:1.

Polymerization Methods

The block polymers of the present invention are formed by any suitable block polymer polymerization process. Examples of such polymerization techniques include, but are not limited to, living free-radical polymerization, cationic polymerization, anionic polymerization, group transfer polymerization, atom transfer polymerization, and coordination-catalyzed polymerization. These and other polymerization processes suitable for making the block polymers of the present invention are described in D. A. Shipp, J. L. Wang, K. Matyjaszewski, *Macromolecules* 31, 8005-8008 (1998) (living free-radical polymerization, atom transfer radical polymerization); A. B. Lowe, N. C. Billingham, S. P. Armes, *Macromolecules* 31, 5991-5998 (1998) (living free-radical polymerization, group transfer polymerization); V. Bütün, N. C. Billingham, S. P. Armes, *Chem. Commun.*, 1997, 671-672 (group transfer polymerization); X. Zhang, K. Matyjaszewski, *Macromolecules*, 32, 1763-1766 (1999) (living free-radical polymerization, atom transfer radical polymerization); N. G. Hoogeveen, M. A. C. Stuart, G. J. Fleer, W. Frank, M. Arnold, *Macromol. Chem. Phys.*, 197, 2553-2564 (1996) (anionic polymerization); S. Creutz, P. Teyssié, R. Jérome, *Macromolecules*, 30, 6-9 (1997) (anionic polymerization); P. Chaumont, D. Colombani, L. Boiteaut, J. P. Lamps, M. O. Zink, C. P. R. Nair, D. Charmot, ACS Symposium Series 685, Controlled Radical Polymerization, ed. K. Matyjaszewski, Ch. 22 (1998); J. Chiefari, Y. K. Chong, F. Ercole, J. Krstina, J. Jeffery, T. P. T. Lee, R. T. A. Mayadunne, G. F. Meijs, C. L. Moad, G. Moad, E. Rizzardo, S. R. Thang, *Macromolecules* 31, 5559-5562 (1998) (living free-radical polymerization, reversible addition-fragmentation chain transfer); A. Sebenik, *Prog. Polym. Sci.*, 23, 875-917 (1998) (living free-radical polymerization); J. Krstina, C. L. Moad, G. Moad, E. Rizzardo, *Macromol. Symp.*, 111, 13-23 (1996) (living free-radical polymerization, addition-fragmentation chain transfer); D. C. Allport, W. H. Janes, "Block Copolymers", Wiley, New York 1973; S. R. Sandler, W. Karo, "Polymer Syntheses", Academic Press, San Diego 1977.

In addition to the various polymerization methods identified in the above-referenced literature sources, those sources also describe suitable catalysts used in the polymerization methods. Accordingly, the block polymers of the present invention can be made by a polymerization process described herein using any suitable catalyst known in the art, examples of which are described in the above-referenced literature sources.

Cationic Charge Density

For the purposes of the present invention the term "cationic charge density" is defined as "the total number of units that are protonated at a specific pH per 100 daltons mass of polymer, or otherwise stated, the total number of charges divided by the dalton molecular weight of the monomer unit or polymer."

For illustrative purposes only, a polypeptide comprising 10 units of the amino acid lysine has a molecular weight of approximately 1028 daltons, wherein there are 11 —$NH_2$ units. If at a specific pH within the range of from about 4 to about 12, 2 of the —$NH_2$, units are protonated in the form of —$NH_3^+$, then the cationic charge density is 2 cationic charge units÷by 1028 daltons molecular weight=approximately 0.2 units of cationic charge per 100 daltons molecular weight. This would, therefore, have sufficient cationic charge to suffice the cationic charge density of the present invention, but insufficient molecular weight to be a suitable suds enhancer.

Polymers have been shown to be effective for delivering sudsing benefits in a hand dishwashing context, provided the polymer contains a cationic moiety, either permanent via a quaternary nitrogen or temporary via protonation. Without being limited by theory, it is believed that the cationic charge must be sufficient to attract the polymer to negatively charged soils but not so large as to cause negative interactions with available anionic surfactants.

The cationic charge density may be determined as follows, where the cationic charge density is defined as the amount of cationic charge on a given polymer, either by permanent cationic groups or via protonated groups, as a weight percent of the total polymer at the desired wash pH. For example, with the terpolymer, DMAM/hydroxyethylacrylate (HEA)/acrylic acid (AA) where the ratio of monomers is 1 mole of DMAM for 3 moles of HEA for 0.33 moles of AA, we have experimentally determined the pKa, see hereinafter as to how pKa is measured, of this polymer to be 8.2. Thus, if the wash pH is 8.2, then half of the available nitrogens will be protonated (and count as cationic) and the other half will not be protonated (and not be counted in the "cationic charge density"). Thus, since the Nitrogen has a molecular weight of approximately 14 grams/mole, the DMAM monomer has a molecular weight of approximately 157 grams/mole, the HEA monomer has a molecular weight of approximately 116 grams/mole, and the AA monomer has a molecular weight of approximately 72 grams/mole, the cationic charge density can be calculated as follows:

$$\text{Cationic Charge Density}=(14/157+116+116+116+72)\\ *50\%=0.0132 \text{ or } 1.32\%.$$

Thus, 1.32% of the polymer contains cationic charges. Otherwise stated, the cationic charge density is 1.32 per 100 daltons molecular weight.

As another example, one could make a copolymer of DMAM with hydroxyethylacrylate (HEA), where the ratio of monomers is 1 mole of DMAM for 3 moles of HEA. The DMAM monomer has a molecular weight of approximately 157 and the HEA monomer has a molecular weight of 116 grams/mole. In this case the pKa has been measured to be 7.6. Thus, if the wash pH is 5.0, all of the available nitrogens will be protonated. The cationic charge density is then calculated:

$$\text{Cationic Charge Density}=14/(157+116+116+116)\\ *100\%=0.0277, \text{ or } 2.77\%.$$

Thus, the cationic charge density is 2.77 per 100 daltons molecular weight. Notice that in this example, the minimum repeating unit is considered 1 DMAM monomer plus 3 HEA monomers.

Alternatively, the cationic charge density can be determined as follows: where the cationic charge density is defined as the total number of charges divided by the dalton molecular weight of the polymer at the desired wash pH. It can be calculated from the following equation $$\text{Catitionic Charge Density} = \frac{\sum_i n_i f_i C_i}{\sum_j m_j}$$

where $n_i$ is the number of charged unit, and $f_i$ is the fraction of unit being charged. In the case of protonated species (AH$^+$), $f_i$ can be calculated from the measured pH and pKa.

$$f_{(AH+)} = \frac{10^{pKa-pH}}{1+10^{pKa-pH}}$$

In the case of deprotonated anionic species (A)

$$f_{(A-)} = \frac{10^{pH-pKa}}{1+10^{pH-pKa}}$$

$C_i$ is the charge of the unit, $m_j$ is the dalton molecular weight of the individual monomer units.

For example, with poly DMAM, we have experimentally determined the pKa, see hereinafter as to how pKa is measured, of this polymer to be 7.7. Thus, if the wash pH is 7.7, then half of the available nitrogens will be protonated (and count as cationic) $f_{(AH+)}=0.5$ and the other half will not be protonated (and not be counted in the "cationic charge density"). Thus, since the DMAM monomer has a molecular weight of approximately 157 grams/mole, the cationic charge density can be calculated:

Cationic Charge Density=(1*0.5/157)=0.00318 or 0.318%.

Thus, at the wash pH of 7.7, polyDMAM has a cationic charge density of 0.318 charge per 100 dalton molecular weight. As another example, one could make a copolymer of DMAM with DMA, where the ratio of monomers is 1 mole of DMAM for 3 moles of DMA. The DMA monomer has a molecular weight of 99 grams/mole. In this case the pKa has been measured to be 7.6. Thus, if the wash pH is 5.0, all of the available nitrogens will be protonated. The cationic charge density is then calculated:

Cationic Charge Density=1/(157+99+99+99)=0.0022, or 0.22%.

At the wash pH of 5.0, a copolymer of DMAM with DMA has a charge density of 0.22 charge per 100 dalton molecular weight. Notice that in this example, the minimum repeating unit is considered 1 DMAM monomer plus 3 DMA monomers.

A key aspect of this calculation is the pKa measurement for any protonatable species which will result in a cationic charge on the heteroatom. Since the pKa is dependent on the polymer structure and various monomers present, this must be measured to determine the percentage of protonatable sites to count as a function of the desired wash pH. This is an easy exercise for one skilled in the art. Based on this calculation, the percent of cationic charge is independent of polymer molecular weight.

The pKa of a polymeric suds booster is determined in the following manner. Make at least 50 mls of a 5% polymer solution, such as a polymer prepared according to any of Examples 1 to 5 as described hereinafter, in ultra pure water (i.e. no added salt). At 25° C., take initial pH of the 5% polymer solution with a pH meter and record when a steady reading is achieved. Maintain temperature throughout the test at 25° C. with a water bath and stir continuously. Raise pH of 50 mls of the aqueous polymer solution to 12 using NaOH (1N, 12.5M). Titrate 5 mls of 0.1N HCl into the polymer solution. Record pH when steady reading is achieved. Repeat steps 4 and 5 until pH is below 3. The pKa was determined from a plot of pH vs. volume of titrant using the standard procedure as disclosed in Quantitative Chemical Analysis, Daniel C. Harris, W.H. Freeman & Chapman, San Francisco, USA 1982.

Effective Amounts

The liquid detergent compositions according to the present invention comprise at least an effective amount of one or more block polymeric materials described herein, preferably from about 0.01% to about 10%, more preferably from about 0.001% to about 5%, most preferably from about 0.1% to about 2% by weight, of said composition. What is meant herein by "an effective amount of polymeric suds stabilizer" is that the suds produced by the presently described compositions are sustained for an increased amount of time relative to a composition which does not comprise a polymeric suds stabilizer described herein.

What is meant by "an effective amount of block polymeric soil release agents" is that the soil is released from fabric being washed to a greater extent relative to a composition which does not comprise one or more of the soil release agents described herein.

For the other uses of these block polymers, such as personal care (e.g., hand wash, body wash, shampoo, shaving cream, post-foaming shaving gel, dephiliatories), oil field foam, fire fighting foam, agrochemical foam, hard surface (e.g., bathroom tile) cleaner foam, shower rinse, and coagulants for titanium dioxide used in paper production, the effective amounts are the amounts for each use which results in an improvement in the desired property in comparison with a composition lacking the block polymer.

Additionally, the block polymeric agent can be present as the free base or as a salt. Typical counter ions include acetate, citrate, maleate, sulfate, chloride, etc.

Hand Dishwashing Compositions and Methods of Use

Detersive Surfactants for Hand Dishwashing

Anionic Surfactants—The anionic surfactants useful in the present invention are preferably selected from the group consisting of, linear alkylbenzene sulfonate, alpha olefin sulfonate, paraffin sulfonates, alkyl ester sulfonates, alkyl sulfates, alkyl alkoxy sulfate, alkyl sulfonates, alkyl alkoxy carboxylate, alkyl alkoxylated sulfates, sarcosinates, taurinates, and mixtures thereof. An effective amount, typically from about 0.5% to about 90%, preferably about 5% to about 60%, more preferably from about 10 to about 30%, by weight of anionic detersive surfactant can be used in the present invention.

Alkyl sulfate surfactants are another type of anionic surfactant of importance for use herein. In addition to providing excellent overall cleaning ability when used in combination with polyhydroxy fatty acid amides (see below), including good grease/oil cleaning over a wide range of temperatures, wash concentrations, and wash times, dissolution of alkyl sulfates can be obtained, as well as improved formulability in liquid detergent formulations are water soluble salts or acids of the formula ROSO$_3$M wherein R preferably is a $C_{10}$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a cation, e.g., an alkali (Group IA) metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperidinium, and cations derived from alkanolamines such as ethanolamine, diethanolamine, triethanolamine, and mixtures thereof and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$-$C_{24}$ alkyl or hydroxyalkyl group having a $C_{10}$-$C_{24}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, etc.), ammonium or substituted-ammonium cation. Alkyl ethoxylated sulfates as well as alkyl propoxylated sulfates are contemplated herein. Specific examples of substituted ammonium cations include methyl-, dimethyl -, trimethyl-ammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$-$C_{18}$ alkylpolyethoxylate (1.0) sulfate, $C_{12}$-$C_{18}$ alkylpolyethoxylate (2.25) sulfate, $C_{12}$-$C_{18}$ alkyl polyethoxylate (3.0) sulfate, and $C_{12}$-$C_{18}$ alkyl polyethoxylate (4.0) sulfate wherein M is conveniently selected from sodium and potassium. Surfactants for use herein can be made from natural or synthetic alcohol feedstocks. Chain lengths represent average hydrocarbon distributions, including branching.

Examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Secondary Surfactants—Secondary detersive surfactant can be selected from the group consisting of nonionics, cationics, ampholytics, zwitterionics, and mixtures thereof. By selecting the type and amount of detersive surfactant, along with other adjunct ingredients disclosed herein, the present detergent compositions can be formulated to be used in the context of laundry cleaning or in other different cleaning applications, particularly including dishwashing. The particular surfactants used can therefore vary widely depending upon the particular end-use envisioned. Suitable secondary surfactants are described below. Examples of suitable nonionic, cationic amphoteric and zwitterionic surfactants are given in "Surface Active Agents and Detergents" (Vol. I and II by Schwartz, Perry and Berch).

Nonionic Detergent Surfactants—Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants include: amine oxides, alkyl ethoxylate, alkanoyl glucose amide, alkyl betaines, sulfobetaine and mixtures thereof.

Amine oxides are semi-polar nonionic surfactants and include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

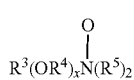

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$-$C_{18}$ alkyl dimethyl amine oxides and $C_8$-$C_{12}$ alkoxy ethyl dihydroxy ethyl amine oxides. Preferably the amine oxide is present in the composition in an effective amount, more preferably from about 0.1% to about 20%, even more preferably about 0.1% to about 15%, even more preferably still from about 0.5% to about 10%, by weight.

The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal® CO-630, marketed by the GAF Corporation; and Triton® X-45, X-114, X-100, and X-102, all marketed by the Rohm & Haas Company. These compounds are commonly referred to as alkyl phenol alkoxylates, (e.g., alkyl phenol ethoxylates).

The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol® 15-S-9 (the condensation product of $C_{11}$-$C_{15}$ linear secondary alcohol with 9 moles ethylene oxide), Tergitol® 24-L-6 NMW (the condensation product of $C_{12}$-$C_{14}$ primary alcohol with 6 moles ethylene oxide with a narrow molecular weight distribution), both marketed by Union Carbide Corporation; Neodol® 45-9 (the condensation product of $C_{14}$-$C_{15}$ linear alcohol with 9 moles of ethylene oxide), Neodol® 23-6.5 (the condensation product of $C_{12}$-$C_{13}$ linear alcohol with 6.5 moles of ethylene oxide), Neodol® 45-7 (the condensation product of $C_{14}$-$C_{15}$ linear alcohol with 7 moles of ethylene oxide), Neodol® 45-4 (the condensation product of $C_{14}$-$C_{15}$ linear alcohol with 4 moles of ethylene oxide), marketed by Shell Chemical Company, and Kyro® EOB (the condensation product of $C_{13}$-$C_{15}$ alcohol with 9 moles ethylene oxide), marketed by The Procter & Gamble Company. Other commercially available nonionic surfactants include Dobanol 91-8® marketed by Shell Chemical Co. and Genapol UD-080® marketed by Hoechst. This category of nonionic surfactant is referred to generally as "alkyl ethoxylates."

The preferred alkylpolyglycosides have the formula

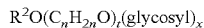

$$R^2O(C_nH_{2n}O)_t(\text{glycosyl})_x$$

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Fatty acid amide surfactants having the formula:

wherein $R^6$ is an alkyl group containing from about 7 to about 21 (preferably from about 9 to about 17) carbon atoms and each $R^7$ is selected from the group consisting of hydrogen, $C_1$-$C_4$ alkyl, $C_1$-$C_4$ hydroxyalkyl, and —$(C^2H_4O)_xH$ where x varies from about 1 to about 3.

Preferred amides are $C_8$-$C_{20}$ ammonia amides, monoethanolamides, diethanolamides, and isopropanolamides.

Preferably the nonionic surfactant, when present in the composition, is present in an effective amount, more preferably from about 0.1% to about 20%, even more preferably about 0.1% to about 15%, even more preferably still from about 0.5% to about 10%, by weight.

polyhydroxy Fatty Acid Amide Surfactant—The detergent compositions hereof may also contain an effective amount of polyhydroxy fatty acid amide surfactant. By "effective amount" is meant that the formulator of the composition can select an amount of polyhydroxy fatty acid amide to be incorporated into the compositions that will improve the cleaning performance of the detergent composition. In general, for conventional levels, the incorporation of about 1%, by weight, polyhydroxy fatty acid amide will enhance cleaning performance.

The detergent compositions herein will typically comprise about 1% weight basis, polyhydroxy fatty acid amide surfactant, preferably from about 3% to about 30%, of the polyhydroxy fatty acid amide. The polyhydroxy fatty acid amide surfactant component comprises compounds of the structural formula:

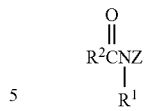

wherein: $R^1$ is H, $C_1$-$C_4$ hydrocarbyl, 2-hydroxy ethyl, 2-hydroxy propyl, or a mixture thereof, preferably $C_1$-$C_4$ alkyl, more preferably $C_1$ or $C_2$ alkyl, most preferably $C_1$ alkyl (i.e., methyl); and $R^2$ is a $C_5$-$C_{31}$ hydrocarbyl, preferably straight chain $C_7$-$C_{19}$ alkyl or alkenyl, more preferably straight chain $C_9$-$C_{17}$ alkyl or alkenyl, most preferably straight chain $C_{11}$-$C_{15}$ alkyl or alkenyl, or mixtures thereof, and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

R' can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

Diamines

The preferred liquid detergent compositions of the present invention further comprise one or more diamines, preferably an amount of diamine such that the ratio of anionic surfactant present to the diamine is from about 40:1 to about 2:1. Said diamines provide for increased removal of grease and greasy food material while maintaining suitable levels of suds.

The diamines suitable for use in the compositions of the present invention have the formula:

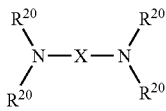

wherein each $R^{20}$ is independently selected from the group consisting of hydrogen, $C_1$-$C_4$ linear or branched alkyl, alkyleneoxy having the formula:

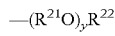

wherein $R^{21}$ is $C_2$-$C_4$ linear or branched alkylene, and mixtures thereof, $R^{22}$ is hydrogen, $C_1$-$C_4$ alkyl, and mixtures thereof; y is from 1 to about 10; X is a unit selected from:
i) $C_3$-$C_{10}$ linear alkylene, $C_3$-$C_{10}$ branched alkylene, $C_3$-$C_{10}$ cyclic alkylene, $C_3$-$C_{10}$ branched cyclic alkylene, an alkyleneoxyalkylene having the formula:

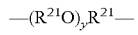

wherein $R^{21}$ and y are the same as defined herein above;
ii) $C_3$-$C_{10}$ linear, $C_3$-$C_{10}$ branched linear, $C_3$-$C_{10}$ cyclic, $C_3$-$C_{10}$ branched cyclic alkylene, $C_6$-$C_{10}$ arylene, wherein said unit comprises one or more electron donating or electron withdrawing moieties which provide said diamine with a $pK_a$ greater than about S; and
iii) mixtures of (i) and (ii)
provided said diamine has a $pK_a$ of at least about 8.

The preferred diamines of the present invention have a $pK_1$ and $pK_2$ which are each in the range of from about 8 to about 11.5, preferably in the range of from about 8.4 to about 11, more preferably from about 8.6 to about 10.75. For the purposes of the present invention the term "$pK_a$" stands equally well for the terms "$pK_1$" and "$pK_2$" either separately or collectively. The term $pK_a$ as used herein throughout the present specification in the same manner as used by those of ordinary skill in the art. $pK_a$ values are readily obtained from standard literature sources, for example, "Critical Stability Constants: Volume 2, mines" by Smith and Martel, Plenum Press, N.Y. and London, (1975).

As an applied definition herein, the $pK_a$ values of the diamines are specified as being measured in an aqueous solution at 25° C. having an ionic strength of from about 0.1 to about 0.5 M. As used herein, the $pK_a$ is an equilibrium constant dependent upon temperature and ionic strength, therefore, value reported by literature references, not measured in the above described manner, may not be within full agreement with the values and ranges which comprise the present invention. To eliminate ambiguity, the relevant conditions and/or references used for $pK_a$'s of this invention are as defined herein or in "Critical Stability Constants: Volume 2, Amines". One typical method of measurement is the potentiometric titration of the acid with sodium hydroxide and determination of the $pK_a$ by suitable methods as described and referenced in "The Chemist's Ready Reference Handbook" by Shugar and Dean, McGraw Hill, NY, 1990.

Preferred diamines for performance and supply considerations are 1,3-bis(methylamino)cyclohexane, 1,3-diaminopropane ($pK_1$=10.5; $pK_2$=8.9), 1,6-diaminohexane ($pK_1$=11; $pK_2$=10), 1,3-diaminopentane (Dytek EP) ($pK_1$0.5; $pK_2$=8.9), 2-methyl 1,5-diaminopentane (Dytek A) ($pK_1$=11.2; $pK_2$=10.0). Other preferred materials are the primary/primary diamines having alkylene spacers ranging from $C_4$-$C_8$. In general, primary diamines are preferred over secondary and tertiary diamines.

The following are non-limiting examples of diamines suitable for use in the present invention.

1-N,N-dimethylamino-3-aminopropane having the formula:

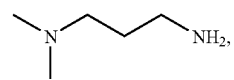

1,6-diaminohexane having the formula:

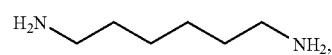

1,3-diaminopropane having the formula:

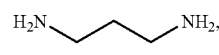

2-methyl-1,5-diaminopentane having the formula:

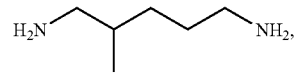

1,3-diaminopentane, available under the tradename Dytek EP, having the formula:

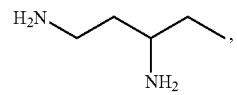

1,3-diaminobutane having the formula:

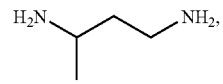

Jeffamine EDR 148, a diamine having an alkyleneoxy backbone, having the formula:

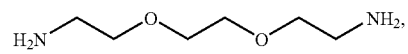

3-methyl-3-aminoethyl-5-dimethyl-1-aminocyclohexane (isophorone diamine) having the formula:

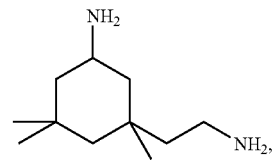

and
1,3-bis(methylamino)cyclohexane having the formula:

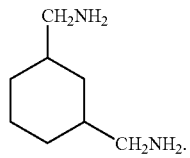

Adjunct Ingredients for Hand Dishwashing

Builder—The compositions according to the present invention may further comprise a builder system. Any conventional builder system is suitable for use herein including aluminosilicate materials, silicates, polycarboxylates and fatty acids, materials such as ethylene-diamine tetraacetate, metal ion sequestrants such as aminopolyphosphonates, particularly ethylenediamine tetramethylene phosphonic acid and diethylene triamine pentamethylene-phosphonic acid. Though less preferred for obvious environmental reasons, phosphate builders can also be used herein.

Suitable polycarboxylates builders for use herein include citric acid, preferably in the form of a water-soluble salt, derivatives of succinic acid of the formula R—CH(COOH)CH$_2$(COOH) wherein R is C10-20 alkyl or alkenyl, preferably C12-16, or wherein R can be substituted with hydroxyl, sulfo sulfoxyl or sulfone substituents. Specific examples include lauryl succinate, myristyl succinate, palmityl succinate 2-dodecenylsuccinate, 2-tetradecenyl succinate. Succinate builders are preferably used in the form of their water-soluble salts, including sodium, potassium, ammonium and alkanolammonium salts.

Other suitable polycarboxylates are oxodisuccinates and mixtures of tartrate monosuccinic and tartrate disuccinic acid such as described in U.S. Pat. No. 4,663,071.

Especially for the liquid execution herein, suitable fatty acid builders for use herein are saturated or unsaturated C10-18 fatty acids, as well as the corresponding soaps. Preferred saturated species have from 12 to 16 carbon atoms in the alkyl chain. The preferred unsaturated fatty acid is oleic acid. Other preferred builder system for liquid compositions is based on dodecenyl succinic acid and citric acid.

Detergency builder salts are normally included in amounts of from 3% to 50% by weight of the composition preferably from 5% to 30% and most usually from 5% to 25% by weight.

Optional Detergent Ingredients for Hand Dishwashing

Enzymes—Detergent compositions of the present invention may further comprise one or more enzymes which provide cleaning performance benefits. Said enzymes include enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, β-glucanases, arabinosidases or mixtures thereof. A preferred combination is a detergent composition having a cocktail of conventional applicable enzymes like protease, amylase, lipase, cutinase and/or cellulase. Enzymes when present in the compositions, at from about 0.0001% to about 5% of active enzyme by weight of the detergent composition.

Proteolytic Enzyme—The proteolytic enzyme can be of animal, vegetable or microorganism (preferred) origin. The proteases for use in the detergent compositions herein include (but are not limited to) trypsin, subtilisin, chymotrypsin and elastase-type proteases. Preferred for use herein are subtilisin-type proteolytic enzymes. Particularly preferred is bacterial serine proteolytic enzyme obtained from *Bacillus subtilis* and/or *Bacillus licheniformis*.

Suitable proteolytic enzymes include Novo Industri A/S Alcalase® (preferred), Esperase®, Savinase® (Copenhagen, Denmark), Gist-brocades' Maxatase®, Maxacal® and Maxapem 15® (protein engineered Maxacal®) (Delft, Netherlands), and subtilisin BPN and BPN' (preferred)$_3$, which are commercially available. Preferred proteolytic enzymes are also modified bacterial serine proteases, such as those made by Genencor International, Inc. (San Francisco, Calif.) which are described in European Patent 251,446B, granted Dec. 28, 1994 (particularly pages 17, 24 and 98) and which are also called herein "Protease B". U.S. Pat. No. 5,030,378, Venegas, issued Jul. 9, 1991, refers to a modified bacterial serine proteolytic enzyme (Genencor International) which is called "Protease A" herein (same as BPN'). In particular see columns 2 and 3 of U.S. Pat. No. 5,030,378 for a complete description, including amino sequence, of Protease A and its variants. Other proteases are sold under the tradenames: Primase, Durazym, Opticlean and Optimase. Preferred proteolytic enzymes, then, are selected from the group consisting of Alcalase® (Novo Industri A/S), BPN', Protease A and Protease B (Genencor), and mixtures thereof. Protease B is most preferred.

Of particular interest for use herein are the proteases described in U.S. Pat. No. 5,470,733.

Also proteases described in our co-pending application U.S. Ser. No. 08/136,797 can be included in the detergent composition of the invention.

Another preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in WO 95/10615 published Apr. 20, 1995 by Genencor International (A. Baeck et al. entitled "Protease-Containing Cleaning Compositions" having U.S. Ser. No. 08/322,676, filed Oct. 13, 1994).

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Protease enzyme may be incorporated into the compositions in accordance with the invention at a level of from 0.0001% to 2% active enzyme by weight of the composition.

Amylase—Amylases (α and/or β) can be included for removal of carbohydrate-based stains. Suitable amylases are Termamyl® (Novo Nordisk), Fungamyl® and BAN® (Novo Nordisk). The enzymes may be of any suitable origin, such as vegetable, animal, bacterial, fungal and yeast origin. Amylase enzymes are normally incorporated in the detergent composition at levels from 0.0001% to 2%, preferably from about 0.0001% to about 0.5%, more preferably from about 0.001% to about 0.11%, even more preferably from about 0.001% to about 0.001% of active enzyme by weight of the detergent composition.

Amylase enzymes also include those described in WO95/26397 and in co-pending application by Novo Nordisk PCT/

DK96/00056. Other specific amylase enzymes for use in the detergent compositions of the present invention therefore include:

(a) α-amylases characterised by having a specific activity at least 25% higher than the specific activity of Termamyl® at a temperature range of 25° C. to 55° C. and at a pH value in the range of 8 to 10, measured by the Phadebas® α-amylase activity assay. Such Phadebas® α-amylase activity assay is described at pages 9-10, WO95/26397.

(b) α-amylases according (a) comprising the amino sequence shown in the SEQ ID listings in the above cited reference. or an α-amylase being at least 80% homologous with the amino acid sequence shown in the SEQ ID listing.

(c) α-amylases according (a) obtained from an alkalophilic Bacillus species, comprising the following amino sequence in the N-terminal: His-His-Asn-Gly-Thr-Asn-Gly-Thr-Met-Met-Gln-Tyr-Phe-Glu-Trp-Tyr-Leu-Pro-Asn-Asp.

A polypeptide is considered to be X % homologous to the parent amylase if a comparison of the respective amino acid sequences, performed via algorithms, such as the one described by Lipman and Pearson in Science 227, 1985, p. 1435, reveals an identity of X %

(d) α-amylases according (a-c) wherein the α-amylase is obtainable from an alkalophilic Bacillus species; and in particular, from any of the strains NCIB 12289, NCIB 12512, NCIB 12513 and DSM 935.

In the context of the present invention, the term "obtainable from" is intended not only to indicate an amylase produced by a Bacillus strain but also an amylase encoded by a DNA sequence isolated from such a Bacillus strain and produced in an host organism transformed with said DNA sequence.

(e) α-amylase showing positive immunological cross-reactivity with antibodies raised against an α-amylase having an amino acid sequence corresponding respectively to those α-amylases in (a-d).

(f) Variants of the following parent α-amylases which (i) have one of the amino acid sequences shown in corresponding respectively to those α-amylases in (a-e), or (ii) displays at least 80% homology with one or more of said amino acid sequences, and/or displays immunological cross-reactivity with an antibody raised against an α-amylase having one of said amino acid sequences, and/or is encoded by a DNA sequence which hybridizes with the same probe as a DNA sequence encoding an α-amylase having one of said amino acid sequence; in which variants:

1. at least one amino acid residue of said parent α-amylase has been deleted; and/or
2. at least one amino acid residue of said parent α-amylase has been replaced by a different amino acid residue; and/or
3. at least one amino acid residue has been inserted relative to said parent α-amylase; said variant having an α-amylase activity and exhibiting at least one of the following properties relative to said parent α-amylase:increased thermostability, increased stability towards oxidation, reduced Ca ion dependency, increased stability and/or α-amylolytic activity at neutral to relatively high pH values, increased α-amylolytic activity at relatively high temperature and increase or decrease of the isoelectric point (pI) so as to better match the pI value for α-amylase variant to the pH of the medium.

Said variants are described in the patent application PCT/DK96/00056.

Other amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, Jun. 1985, pp. 6518-6521. Certain preferred embodiments of the present compositions can make use of amylases having improved stability in detergents such as automatic dishwashing types, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9-10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Bacillus amylases, especially the Bacillus α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the B. licheniformis alpha-amylase, known as TERMAMYL®, or the homologous position variation of a similar parent amylase, such as B. amyloliquefaciens, B. subtilis, or B. stearothermophilus; (b) stability-enhanced amylases as described by Genencor International in a paper entitled "Oxidatively Resistant alpha-Amylases" presented at the 207th American Chemical Society National Meeting, Mar. 13-17, 1994, by C. Mitchinson. Therein it was noted that bleaches in automatic dishwashing detergents inactivate alpha-amylases but that improved oxidative stability amylases have been made by Genencor from B. licheniformis NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Various carbohydrase enzymes which impart antimicrobial activity may also be included in the present invention. Such enzymes include endoglycosidase, Type II endoglycosidase and glucosidase as disclosed in U.S. Pat. Nos. 5,041,236, 5,395,541, 5,238,843 and 5,356,803 the disclosures of which are herein incorporated by reference. Of course, other enzymes having antimicrobial activity may be employed as well including peroxidases, oxidases and various other enzymes.

It is also possible to include an enzyme stabilization system into the compositions of the present invention when any enzyme is present in the composition.

Perfumes—Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Non-limiting examples of perfume ingredients useful herein include: 7-acetyl-1,2,3,4,5,6,7,8-octahydro-1,1,6,7-tetramethyl naphthalene; ionone methyl; ionone gamma methyl; methyl cedrylone; methyl dihydrojasmonate; methyl 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; para-hydroxy-phenyl-butanone; benzophenone; methyl beta-naphthyl ketone; 6-acetyl-1,1,2,3,3,5-hexamethyl indane; 5-acetyl-3-isopropyl-1,1,2,6-tetramethyl indane; 1-dodecanal, 4-(4-hydroxy-4-methylpentyl)-3-cyclohexene-1-carboxaldehyde; 7-hydroxy-3,7-dimethyl ocatanal; 10-undecen-1-al; iso-hexenyl cyclohexyl carboxaldehyde; formyl tricyclodecane; condensation products of hydroxycitronellal and methyl anthranilate, condensation products of hydroxycitronellal and indol, condensation products of phenyl acetaldehyde and indol; 2-methyl-3-(para-tert-butylphenyl)-propionaldehyde; ethyl vanillin; heliotropin; hexyl cinnamic aldehyde; amyl cinnamic aldehyde, 2-methyl-2-(para-iso-propylphenyl)-propionaldehyde; coumarin; decalactone gamma; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; beta-naphthol methyl ether; ambroxane; dodecahydro-3a,6,6,9a-tetra-methylnaphtho[2,1b]furan; cedrol, 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; tricyclodecenyl propionate; tricyclodecenyl acetate; benzyl salicylate; cedryl acetate; and para-(tert-butyl)cyclohexyl acetate.

Particularly preferred perfume materials are those that provide the largest odor improvements in finished product compositions containing cellulases. These perfumes include but are not limited to: hexyl cinnamic aldehyde; 2-methyl-3-(para-tert-butylphenyl)-propionaldehyde; 7-acetyl-1,2,3,4,5,6,7,8-octahydro-1,1,6,7-tetramethyl naphthalene; benzyl salicylate; 7-acetyl-1,1,3,4,4,6-hexamethyl tetralin; para-tert-butyl cyclohexyl acetate; methyl dihydro jasmonate; beta-napthol methyl ether; methyl beta-naphthyl ketone; 2-methyl-2-(para-iso-propylphenyl)-propionaldehyde; 1,3,4,6,7,8-hexahydro-4,6,6,7,8,8-hexamethyl-cyclopenta-gamma-2-benzopyrane; dodecahydro-3a,6,6,9a-tetramethyl-naphtho[2,1b]furan; anisaldehyde; coumarin; cedrol; vanillin; cyclopentadecanolide; tricyclodecenyl acetate; and tricyclodecenyl propionate.

Other perfume materials include essential oils, resinoids, and resins from a variety of sources including, but not limited to: Peru balsam, Olibanum resinoid, styrax, labdanum resin, nutmeg, *cassia* oil, benzoin resin, coriander and lavandin. Still other perfume chemicals include phenyl ethyl alcohol, terpineol, linalool, linalyl acetate, geraniol, nerol, 2-(1,1-dimethylethyl)-cyclohexanol acetate, benzyl acetate, and eugenol. Carriers such as diethylphthalate can be used in the finished perfume compositions.

Chelating Agent—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilo-tri-acetates, ethylenediamine tetrapro-prionates, triethylenetetraaminebexacetates, diethylenetriaminepentaacetates, and ethanoldi-glycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis(methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder. Similarly, the so called "weak" builders such as citrate can also be used as chelating agents.

If utilized, these chelating agents will generally comprise from about 0.10 to about 15% by weight of the detergent compositions herein. More preferably, if utilized, the chelating agents will comprise from about 0.1% to about 3.0% by weight of such compositions.

Composition pH

Dishwashing compositions of the invention will be subjected to acidic stresses created by food soils when put to use, i.e., diluted and applied to soiled dishes. If a composition with a pH greater than 7 is to be more effective, it preferably should contain a buffering agent capable of providing a generally more alkaline pH in the composition and in dilute solutions, i.e., about 0.1% to 0.4% by weight aqueous solution, of the composition. The pKa value of this buffering agent should be about 0.5 to 1.0 pH units below the desired pH value of the composition (determined as described above). Preferably, the pKa of the buffering agent should be from about 7 to about 10. Under these conditions the buffering agent most effectively controls the pH while using the least amount thereof.

The buffering agent may be an active detergent in its own right, or it may be a low molecular weight, organic or inorganic material that is used in this composition solely for maintaining an alkaline pH. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are Tri(hydroxymethyl)amino methane $(HOCH_2)_3CNH_3$ (TRIS), 2-amino-2-ethyl-1,3-propanediol, 2-amino-2-methyl-propanol, 2-amino-2-methyl-1,3-propanol, disodium glutamate, N-methyl diethanolamide, 1,3-diamino-propanol N,N'-tetramethyl-1,3-diamino-2-propanol, N,N-bis(2-hydroxyethyl) glycine (bicine) and N-tris(hydroxymethyl)methyl glycine (tricine). Mixtures of any of the above are also acceptable. Useful inorganic buffers/alkalinity sources include the alkali metal carbonates and alkali metal phosphates, e.g., sodium carbonate, sodium polyphosphate. For additional buffers see McCutcheon's EMULSIFIERS AND DETERGENTS, North American Edition, 1997, McCutcheon Division, MC Publishing Company Kirk and WO 95/07971 both of which are incorporated herein by reference.

The buffering agent, if used, is present in the compositions of the invention herein at a level of from about 0.1% to 15%, preferably from about 1% to 10%, most preferably from about 2% to 8%, by weight of the composition.

Calcium and/or Magnesium Ions

The presence of calcium and/or magnesium (divalent) ions improves the cleaning of greasy soils for various compositions, i.e., compositions containing alkyl ethoxy sulfates and/or polyhydroxy fatty acid amides. This is especially true when the compositions are used in softened water that contains few divalent ions. It is believed that calcium and/or magnesium ions increase the packing of the surfactants at the oil/water interface, thereby reducing interfacial tension and improving grease cleaning.

Compositions of the invention herein containing magnesium and/or calcium ions exhibit good grease removal, manifest mildness to the skin, and provide good storage stability. These ions can be present in the compositions herein at an active level of from about 0.1% to 4%, preferably from about 0.3% to 3.5%, more preferably from about 0.5% to 1%, by weight.

Preferably, the magnesium or calcium ions are added as a hydroxide, chloride, acetate, formate, oxide or nitrate salt to the compositions of the present invention. Calcium ions may also be added as salts of the hydrotrope.

The amount of calcium or magnesium ions present in compositions of the invention will be dependent upon the amount of total surfactant present therein. When calcium ions are present in the compositions of this invention, the molar ratio of calcium ions to total anionic surfactant should be from about 0.25:1 to about 2:1.

Formulating such divalent ion-containing compositions in alkaline pH matrices may be difficult due to the incompatibility of the divalent ions, particularly magnesium, with hydroxide ions. When both divalent ions and alkaline pH are combined with the surfactant mixture of this invention, grease cleaning is achieved that is superior to that obtained by either alkaline pH or divalent ions alone. Yet, during storage, the stability of these compositions becomes poor due to the formation of hydroxide precipitates. Therefore, chelating agents discussed hereinbefore may also be necessary.

Other Ingredients—The detergent compositions will further preferably comprise one or more detersive adjuncts selected from the following: soil release polymers, polymeric dispersants, polysaccharides, abrasives, bactericides, tarnish inhibitors, builders, enzymes, opacifiers, dyes, buffers, antifungal or mildew control agents, insect repellents, perfumes, hydrotropes, thickeners, processing aids, suds boosters, brighteners, anti-corrosive aids, stabilizers antioxidants and chelants. A wide variety of other ingredients useful in detergent compositions can be included in the compositions herein, including other active ingredients, carriers, hydrotropes, antioxidants, processing aids, dyes or pigments, solvents for liquid formulations, solid fillers for bar compositions, etc. If high sudsing is desired, suds boosters such as the $C_{10}$-$C_{16}$ alkanolamides can be incorporated into the compositions, typically at 1%-10% levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous.

An antioxidant can be optionally added to the detergent compositions of the present invention. They can be any conventional antioxidant used in detergent compositions, such as 2,6-di-tert-butyl-4-methylphenol (BHT), carbamate, ascorbate, thiosulfate, monoethanolamine(MEA), diethanolamine, triethanolamine, etc. It is preferred that the antioxidant, when present, be present in the composition from about 0.001% to about 5% by weight.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%-5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500-12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Further, these hand dishwashing detergent embodiments preferably further comprises a hydrotrope. Suitable hydrotropes include sodium, potassium, ammonium or water-soluble substituted ammonium salts of toluene sulfonic acid, naphthalene sulfonic acid, cumene sulfonic acid, xylene sulfonic acid.

The detergent compositions of this invention can be in any form, including granular, paste, gel or liquid. Highly preferred embodiments are in liquid or gel form. Liquid detergent compositions can contain water and other solvents as carriers. Low molecular weight primary or secondary alcohols exemplified by methanol ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

An example of the procedure for making granules of the detergent compositions herein is as follows:—Linear alkylbenzenesulfonate, citric acid, sodium silicate, sodium sulfate perfume, diamine and water are added to, heated and mixed via a crutcher. The resulting slurry is spray dried into a granular form.

An example of the procedure for making liquid detergent compositions herein is as follows:—To the free water and citrate are added and dissolved. To this solution amine oxide, betaine, ethanol, hydrotrope and nonionic surfactant are added. If free water isn't available, the citrate are added to the above mix then stirred until dissolved. At this point, an acid is added to neutralize the formulation. It is preferred that the acid be chosen from organic acids such as maleic and citric, however, inorganic mineral acids may be employed as well. In preferred embodiments these acids are added to the formulation followed by diamine addition. AExS is added last.

Non-Aqueous Liquid Detergents

The manufacture of liquid detergent compositions which comprise a non-aqueous carrier medium can be prepared according to the disclosures of U.S. Pat. Nos. 4,753,570; 4,767,558; 4,772,413; 4,889,652; 4,892,673; GB-A-2,158, 838; GB-A-2,195,125; GB-A-2,195,649; U.S. Pat. No. 4,988,462; U.S. Pat. No. 5,266,233; EP-A-225,654 (Jun. 16, 1987); EP-A-510,762 (Oct. 28, 1992); EP-A-540,089 (May 5, 1993); EP-A-540,090 (May 5, 1993); U.S. Pat. No. 4,615, 820; EP-A-565,017 (Oct. 13, 1993); EP-A-030,096 (Jun. 10, 1981), incorporated herein by reference. Such compositions can contain various particulate detersive ingredients stably suspended therein. Such non-aqueous compositions thus comprise a LIQUID PHASE and, optionally but preferably, a SOLID PHASE, all as described in more detail hereinafter and in the cited references.

The compositions of this invention can be used to form aqueous washing solutions for use hand dishwashing. Generally, an effective amount of such compositions is added to water to form such aqueous cleaning or soaking solutions. The aqueous solution so formed is then contacted with the dishware, tableware, and cooking utensils.

An effective amount of the detergent compositions herein added to water to form aqueous cleaning solutions can comprise amounts sufficient to form from about 500 to 20,000 ppm of composition in aqueous solution. More preferably, from about 800 to 5,000 ppm of the detergent compositions herein will be provided in aqueous cleaning liquor.

Method of Use for Hand Dishwashing

The present invention also relates to a method for providing increased suds volume and increased suds retention while hand washing dishware or cookware articles in need of cleaning, comprising the step of contacting said articles with an aqueous solution of a detergent composition suitable for use in hand dishwashing, said composition comprising:
 a) an effective amount of a polymeric suds stabilizer as hereinbefore defined;
 b) an effective amount of a detersive surfactant; and
 c) the balance carriers and other adjunct ingredients;
 provided the pH of a 10% aqueous solution of said composition is from about 4 to about 12.

The present invention also relates to a means for preventing the redeposition of grease, oils, and dirt, especially grease, from the hand washing solution onto dishware. This method comprises contacting an aqueous solution of the compositions of the present invention with soiled dishware and washing said dishware with said aqueous solution.

An effective amount of the detergent compositions herein added to water to form aqueous cleaning solutions according to the method of the present invention comprises amounts sufficient to form from about 500 to 20,000 ppm of composition in aqueous solution. More preferably, from about 800 to 2,500 ppm of the detergent compositions herein will be provided in aqueous cleaning liquor.

The liquid detergent compositions of the present invention are effective for preventing the redeposition of grease from the wash solution back onto the dishware during washing. One measure of effectiveness of the compositions of the present invention involves redeposition tests. The following test and others of similar nature are used to evaluate the suitability of the formulas described herein.

A polyethylene 2 L graduated cylinder is filled to the 1 L graduation mark with an aqueous (water=7 grain) solution comprising from about 500 to about 20,000 ppm of a liquid detergent composition according to the present invention. A synthetic greasy soil composition is then added to the cylinder and the solution is agitated. After a period of time the solution is decanted from the graduated cylinder and the interior walls of the graduated cylinder are rinsed with a suitable solvent or combination of solvents to recover any re-deposited greasy soil. The solvent is removed and the weight of greasy soil which remains in solution is determined by subtracting the amount of soil recovered from the amount initially added to the aqueous solution.

Other re-deposition test include immersion of tableware, flatware, and the like and recovering any re-deposited soil.

The above test can be further modified to determine the increased amount of suds volume and suds duration. The solution is first agitated then subsequently challenged with portions of greasy soil with agitation between each subsequent soil addition. The suds volume can be easily determined by using the vacant volume of the 2 L cylinder as a guide.

Compositions for Personal Care Products

In addition to the polymers of the present invention, beauty care and personal care products, such as shampoos and soaps for hand and/or body wash, of the present invention contain adjunct ingredients. Additional background on such products is provided by PCT application serial number PCT/US98/ 04474, filed Mar. 6, 1998 and published as WO 98/38973, incorporated herein by reference in its entirety.

Pearlescent additives, also known as pearlizing agents, are added to beauty and personal care products such as hair and skin care products to provide a pearly appearance to the products. Chemicals which are tiny (micron size) needles or platelets often exhibit this pearly appearance. Materials which exhibit this effect are ethylene glycol mono- and distearate, $TiO_2$ coated mica, bismuth oxychloride, and natural mother of pearl. Many organic materials exhibit this pearlescence provided they can be produced in an appropriate needle or platelet shape. Ethylene glycol distearate (EGDS) or ethylene glycol monostearate (EGMS) are the most commonly utilized pearlizing agents.

A stable, mild free flowing cold pearlizing concentrate is typically prepared using i) a pearlizing agent of this invention, preferably a glycol stearate; ii) a nonionic surfactant; iii) an amphoteric surfactant emulsifier and stabilizer, iv) a glycol emulsifier and v) water; to obviate the use of cocodiethanolamide and provide excellent compatibility with any ionic surfactant. The concentrate will typically be essentially free of anionic surfactants such that the concentrate is compatible with essentially any ionic surfactants that may be used in the personal care product to which this concentrate is added.

The pearlizing agent comprises from about 5% to about 40%, preferably from about 10% to about 30% and most preferably from about 15% to about 25%, by weight based on the total weight of the concentrate.

The pearlizing agent can be selected from the group consisting of hydroxyl stearate, polyethylene glycol mono- and di-stearates, ethylene glycol mono- and distearates, stearic monoethanolamide, and mixtures thereof. The preferred agents are polyethylene glycol mono- and distearates, and ethylene glycol mono- and di-stearates. The most preferred pearlizing agents for use are: ethylene glycol mono- and di-stearates.

The fatty acid based member must be derived from a fatty acid feedstock (which includes free fatty acids, carboxylate salts, fatty mono-, di- and/or tri-glycerides) which consists of at least about 90% by weight of octadecanoic acid, i.e. the saturated fatty acid having one carboxyl group (or derivative thereof and a seventeen carbon alkyl tail covalently bonded thereto. Stearic acid is available commercially in different grades, typically containing at least some portion of palmitic acid, i.e. the saturated fatty acid having one carboxyl group, and a fifteen carbon alkyl tail covalently bonded thereto. For example, stearic acid is available in grades of 37.5% (nominal) and 42.5% (nominal) purity. Thus, those grades of stearic acid wherein less than about 90% of the fatty acid chains are octadecanoic acid will not be useful in making the fatty acid based member used herein, unless the stearic acid is first purified to remove a sufficient number of species which are not derived from octadecanoic acid. A useful grade of stearic acid is the 95% (nominal) grade the CTFA specifications of which are 92.5% to 97.5% stearic acid and a maximum of 5% palmitic acid. A fatty acid comprised of 90% stearic acid and 10% palmitic acid should also be useful.

The pearlizing agent is most useful as a concentrate with other components, e.g. those other components as described in published Patent Cooperation Treaty Application WO 98/38973, published Sep. 11, 1998, the disclosure of which is incorporated herein by reference in its entirety.

A second component of the beauty and personal care product is a nonionic surfactant. This surfactant can function as an emulsifier and stabilizer in the formulation. The term "nonionic surfactant" as utilized herein encompasses mixtures of nonionic surfactants.

Examples of useful nonionic surfactants include condensates of ethylene oxide with a hydrophobic moiety which has an average hydrophilic lipophilic balance (HLB) between about 8 to about 16, and more preferably, between about 10 and about 12.5. These surfactants include the condensation products of primary or secondary aliphatic alcohols having from about 8 to about 24 carbon atoms, in either straight or branched chain configuration, with from about 2 to about 40, and preferably between about 2 and about 9 moles of ethylene oxide per mole of alcohol.

In a preferred embodiment the aliphatic alcohol comprises between about 9 and about 18 carbon atoms and is ethoxylated with between about 3 and about 12 moles of ethylene oxide per mole of aliphatic alcohol. Especially preferred are the about 12 to about 15 carbon primary alcohol ethoxylates containing about 5 to about 9 moles of ethylene oxide per mole of alcohol. One such material is commercially sold under the trade name NEODOL 25-9 by Shell Chemical Company. Other commercial nonionic surfactants include NEODOL 25-6.5 and NEODOL 25-7 sold by Shell Chemical Company.

Other suitable nonionic surfactants include the condensation products of about 6 to about 12 carbon atom alkyl phenols with about 3 to about 30, and preferably between about 5 and 14 moles of ethylene oxide. Examples of such surfactants are sold under the trade manes Igepal CO 530, Igepal CO 630, Igepal CO720 and Igepal CO 730 by Rhodia, Inc. Still other suitable nonionic surfactants are described in U.S. Pat. No. 3,976,586. To the extent necessary, this patent is expressly incorporated by reference. Most preferred for use are mixed linear alcohol ethoxylates such as Laureth-7 sold as Rhodasurf L-790 by Rhodia, Inc.

The nonionic surfactant is incorporated in the cold pearlizing concentrate in an amount of from about 3% to about 30%; preferably from about 8% to about 25% and most preferably from about 10% to 20%, based on the total weight of the concentrate.

An amphoteric surfactant comprises the third component of the present invention. The term "amphoteric surfactant" as utilized herein encompasses one or more amphoteric surfactants such as mixtures of amphoteric surfactants. Preferably, amphoteric surfactants known as the betaines, their derivatives, and mixtures thereof are incorporated to provide an enhanced pearlizing effect.

Examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates wherein alkyl represents an alkyl group having 6 to 20 carbon atoms. Other suitable amphoteric surfactants include alkyl iminopropionates, alkyl iminodipropionates and alkyl amphopropylsulfonates having between 12 and 18 carbon atoms; alkyl betaines and amidopropyl betaines and alkyl sultaines and alkylamidopropylhydroxy sultaines wherein alkyl represents an alkyl group having 6 to 20 carbon atoms.

Particularly useful amphoteric surfactants include both mono and dicarboxylates such as those of the formulae:

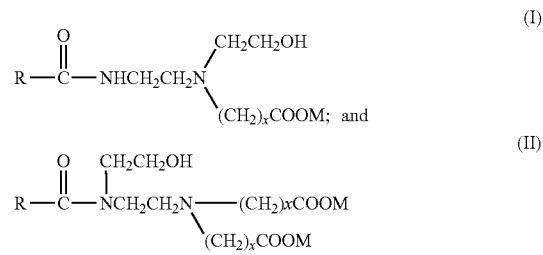

wherein R is an alkyl group of 6-20 carbon atoms, x is 1 or 2 and M is hydrogen or sodium. Mixtures of the above structures are particularly preferred.

Other formulae for the above amphoteric surfactants include the following:

Alkyl betaines

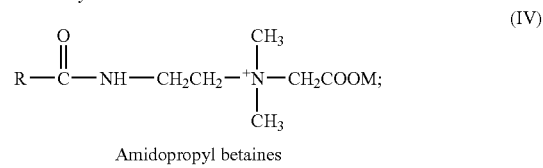

Amidopropyl betaines

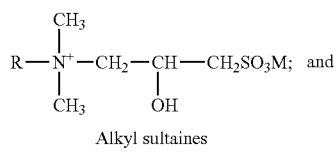

Alkyl sultaines

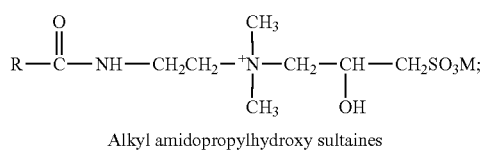

Alkyl amidopropylhydroxy sultaines where R is a alkyl group of 6-20 carbon atoms and M is potassium, sodium or a monovalent cation.

Of the above amphoteric surfactants, particularly preferred are the alkali salts of alkyl amphodipropionates, alkyl amphodiacetates, alkyl amphoglycinates, alkyl amphopropyl sulfonates and alkyl amphopropionates wherein alkyl represents an alkyl group having 6 to 20 carbon atoms. Even more preferred are compounds wherein the alkyl group is derived from coconut oil or is a lauryl group, for example cocoamphodipropionate. Such cocoamphodipropionate surfactants are commercially sold under the trademarks MIRANOL C2M-SF CONC. and MIRANOL FBS by Rhodia, Inc.

Other commercially useful amphoteric surfactants include:

cocoamphoacetate (sold under the trademarks MIRANOL ULTRA C-32 and MIRAPON FA), cocoamphopropionate (sold under the trademarks MIRANOL CMSF CONC. and MIRAPON FAS), cocoamphodiacetate (sold under the trademarks MIRANOL C2M CONC. and MIRAPON FB), lauroamphoacetate (sold under the trademarks MIRANOL HM CONC. and MIRAPON LA), lauroamphodiacetate (sold under the trademarks MIRANOL H2M CONC. and MIRAPON LB), a lauroamphodipropionate (sold under the trademarks MIRANOL H2M-SF CONC. AND MIRAPON LBS), lauroamphodiacetate obtained from a mixture of lauric and myristic acids (sold under the trademark MIRANOL BM CONC.). and cocoamphopropyl sulfonate (sold under the trademark MIRANOL CS CONC.)

caproamphodiacetate (sold under the trademark MIRANOL S2M CONC.), caproamphoacetate (sold under the trademark MIRANOL SM CONC.), caproamphodipropionate (sold under the trademark MIRANOL S2M-SF CONC.), and stearoamphoacetate (sold under the trademark MIRANOL DM).

The most preferred amphoteric surfactant for use is cocoamphoacetate. It can be present from 0% to 10% based on the total weight of the concentrate. Preferably, cocoamphoacetate will comprise from about 10 to about 7% and most preferably from about 2% to about 4% of the concentrate.

Also useful herein are the betaines and amidobetaines which are compounds of the general structure:

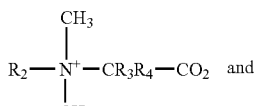

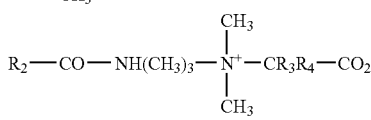

respectively wherein $R_2$ is $C_8$-$C_{22}$ alkyl or alkenyl; $R_3$ is H or $C_1$-$C_4$ alkyl; and $R_4$ is H or $C_1$-$C_4$ alkyl.

The betaines useful herein include the high alkyl betaines such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine. The sulfobetaines are also preferred and may be represented by cocodimethyl sulfopropyl betaine, stearyldimethyl sulfopropyl betaine, lauryl dimethyl sulfoethyl betaine, lauryl bis-(2-hydroxy-ethyl)sulfopropyl betaine and mixtures thereof. A particularly preferred composition utilizes cocoamidopropyl betaine.

Most preferably, the amphoteric surfactant can be cocoamphoacetate and cocoamidopropyl betaine acting as amphoteric co-emulsifiers.

The amphoteric surfactant can be present from about 2% to about 20% weight percent based on the total weight of the pearlizing concentrate. Preferably, the amphoteric will comprise from about 4% to about 16%, most preferably from about 6% to about 10%, of the pearlizing concentrate.

The fourth component consists of a glycol emulsifier. Propylene glycol (1,2, and 1,3) and other alcohols such as 1,3-butylene glycol, 2,3-butylene glycol, ethylene glycol and mixtures thereof are useful emulsifiers. The glycol emulsifier can be present from 0% to about 15%, preferably from about 1% to about 10% and most preferably from about 2% to about 5%.

For the fifth component, the remainder is water, preferably deionized. Generally, water is added in an amount of from about 20% to about 70%, preferably from about 30% to about 60%, and most preferably from about 40% to about 55% based on the total weight of the concentrate.

Non-essential optional components can be utilized in the concentrates of the present invention as a convenient means of incorporation into beauty and personal care products. Such conventional optional ingredients are well known to those skilled in the art, e.g., preservatives such as benzyl alcohol, methyl paraben, propyl paraben and imidazolidinyl urea; thickeners and viscosity modifiers such as block polymers of ethylene oxide and propylene oxide, e.g. ANTAROX F-88 (Rhodia, Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from 0% to about 2%, preferably from 0.01% to about 1.0% by weight of the concentrate.

The pH of the concentrate compositions is not critical and can be in the range of from about 2 to about 12, preferably from about 4 to about 10 and most preferably from about 6 to about 8. The pH can be adjusted using a buffer such as citric acid.

The order of addition to the mixing tank of the individual components of the concentrate is not critical nor is the reasonably elevated temperature; however, preferably the water and pearlizing agent are intimately blended at from about 50° to about 90° C., more preferably from about 70° to about 80° C. with high agitation until the pearlizing agent is emulsified. The nonionic and amphoteric surfactants are then blended into the mix until the mixture is clear. The mixture is then allowed to cool to room temperature. Generally, the concentrate can be stored at a temperature of from about 0° C. to about 45° C. preferably from about 15° C. to about 35° C. for at least one day and preferably two days in order to fully develop its pearlizing characteristics.

The personal care compositions may further comprise a silicone compound. As referred to herein, a silicone compound is a nonfunctionalized siloxane having a viscosity of from about 5 to about 600,000 cs (centistoke), and preferably from about 350 to about 10,000 cs, at 25° C. The so-called "rigid silicones", as described in U.S. Pat. No. 4,902,499, herein incorporated by reference, having a viscosity above 600,000 cs at 20° C., e.g., 700,000 cs plus, and a weight average molecular weight of at least about 500,000, also are useful. The silicone compound is typically a polydimethylsiloxane, typically a linear polydimethylsiloxane terminated at each end with a trimethylsilyl group. The silicone compound can be a dimethicone as specified by the CTFA, i.e. an alpha, omega-trimethylsilyl-polydimethylsiloxane having a viscosity at 25° C. of at least 25 centistokes and less than 60,000 centistokes. The silicone compound is typically used in the context of a shampoo and is added to the composition in an amount sufficient to impart improved combing and improved feel, such as softness, to the hair after shampooing.

The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

The silicone hair conditioning agent will be used in the shampoo compositions hereof at levels of from about 0.1% to about 10% by weight of the composition, preferably from about 0.5% to about 8%, more preferably from about 1% to about 5%.

Suitable insoluble, nonvolatile silicone fluids include polyalkyl siloxanes, polyaryl siloxanes, polyalkylaryl siloxanes, polyether siloxane copolymer and mixtures thereof. However, other insoluble, nonvolatile silicone fluids having hair conditioning properties may be used. The term "nonvolatile" as used herein shall mean that the silicone material exhibits very low or no significant vapor pressure at ambient conditions, as is well understood in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. The term "silicone", as used herein, shall be synonomous with the term "polysiloxane".

The nonvolatile polyalkylsiloxane fluids that may be used include, for example, polydimethyl siloxanes. These siloxanes are available, for example, from the General Electric Company as a VISCASIL series and from Dow Corning as the Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the structure shown in U.S. Pat. No. 5,573,709, the disclosure of which is incorporated herein by reference, herein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen: silicon atoms is at least about 1.2:1.0. Silanes used in the manufacture of silicone resins include monomethyl-, dimethyl-, monophenyl-, diphenyl-, methylphenyl-, monovinyl-, and methylvinyl-chlorosilanes, and tetra-chlorosilane, with the methyl-substituted silanes being most commonly utilized. Preferred resins are offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such unhardened form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204-308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:10 to about 1.5:1.0 and the average molecular weight of the resin is from about 1000 to about 10,000.

The weight ratio of the nonvolatile silicone fluid component to the silicone resin component is from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

The shampoo will contain a detersive surfactant. These include anionic, cationic, nonionic surfactants, amphoteric surfactants, zwitterionic surfactants. Examples of anionic surfactants are described in U.S. Pat. No. 5,573,709, the entire disclosure of which is incorporated by reference. However, the shampoo will typically be essentially free of anionic surfactants, e.g. contain less than 0.5% by weight of species that can properly be characterized as anionic surfactants. If the formulation does not include an anionic surfactant, cationic detersive surfactants can also be used.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

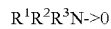

wherein R1 contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyl-decylamine oxide, dimethyl-tetradecylamine oxide, 3,6,9-trioxaheptadecyldiethylamine oxide, di(2hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

RR'R"P->O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9-trioxaoctadecyldimethylphosphine oxide, cetyldimethylphosphine oxide, 3-dodecoxy-2-hydroxypropyldi (2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is: found in U.S. Pat. No. 5,573,709, which is incorporated herein by reference, wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-5-hexadecylsulfonio]-3-hydroxypentane-1-sulfate;
3-[P,P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the 1 like; amidobetaines and amidosulfobetaines, wherein the RCONH ($CH_2$)$_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric detersive surfactants which can be used in the compositions of the present invention arc those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378. Another detersive surfactant optional for use in the compositions of the present invention is cocoamphocarboxy glycinate.

The most preferred shampoos of the present invention contain combinations of amphoteric surfactants, zwitterionic surfactants, and nonionic surfactants and are essentially free of anionic surfactants. The shampoos typically contain from about 0% to about 6% of amphoteric surfactants, about 0% to about 8% of zwitterionic surfactants, from 0% to about 14% of ethoxylated alkyl sulfates, and from about 0% to about 10% of an optional anionic surfactant surfactants, e.g. about 3% to about 7% alkyl sulfates, with a total surfactant level of from about 10% to about 25%.

The formulated shampoo and soap systems of the present invention can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as block polymers of ethylene oxide and propylene oxide, e.g. ANTAROX F-88 (Rhone-Poulenc Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from about 0.01% to about 10%, preferably from 0.5% to about 5.0% by weight of the composition.

Shampoos may also include antidandruff agents such as pyrithione salts, preferably zinc pyrithione, as disclosed by PCT application number PCT/US98/04139, filed Mar. 4, 1998 and published as WO 98/41505, incorporated herein by reference in its entirety.

Hair Removal Personal Care Products

The foam enhancer of the present invention may also be employed with foam foaming shaving gels and shaving creams. Typical foaming shaving gels are disclosed by U.S. Pat. Nos. 5,902,778 to Hartmann, et al; 5,858,343 to Szymczak; and 5,853,710 to Dehan, et al, all of which are incorporated herein by reference in their entirety. Typical foam shaving creams are disclosed by U.S. Pat. Nos. 5,686,024 to Dahanayake, et al; 5,415,860 to Beucherie, et al; 5,902,574 to Stoner, et al; and 5,104,643 to Grollier, et al, all of which are incorporated herein by reference in their entirety.

The foam enhancer is also useful in a dephilatory. An example of a dephilatory is disclosed in U.S. Pat. No. 4,734,099 to Cyprien.

Compositions and Methods of Use for Laundry Detergents

In addition to the block polymers of the present invention (used as soil release agents), laundry detergents of the present invention (whether used for washing by hand or in a washing machine) further include adjunct ingredients. A variety of such adjunct laundry detergent ingredients are disclosed by PCT International Publication No. WO 98/39401, incorporated herein by reference in its entirety.

In general, the laundry detergent compositions are solid granules, liquid or gel and comprise a major amount by weight of detergent and a minor amount of the soil release polymer of the present invention. Also, in general the method for washing fabric of the present invention comprises washing a fabric article in a washing medium comprised of a major amount by weight of water and a first minor amount by weight of detergent and a second minor amount by weight of the soil release polymer. Minor amounts of adjunct components may also be present.

I. Aminoalkyl/alkoxysilane-silicone Compounds

One of the adjunct components of the compositions and methods of this invention is an aminosilicone compound, typically an aminosilicone compound of the formula:

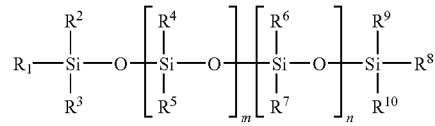

wherein:

$R^1$ and $R^8$ are independently selected from the group consisting of hydrogen, hydroxyl, alkyl (typically $C_1$-$C_4$) and alkoxy (typically $C_1$-$C_4$), $R^2$, $R^3$, $R^9$ and $R^{10}$ are independently selected from the group consisting of alkyl (typically $C_1$-$C_4$) and alkoxy (typically $C_1$-$C_4$), provided that one of $R^2$, $R^3$, $R^9$, and $R^{10}$ may be selected from the group consisting of a primary amino-substituted alkyl group, and a secondary amino-substituted alkyl group (typically an N-(amino-alkyl)-substituted aminoalkyl group such that the compound will have both primary and secondary amine functionality), $R^4$, $R^5$, and $R^6$ are independently selected from the group consisting of alkyl (typically $C_1$-$C_4$) and aryl (typically phenyl), $R^7$ is selected from the group consisting of a primary amino-substituted alkyl group, and a secondary amino-substituted alkyl group (typically an N-(aminoalkyl)-substituted aminoalkyl group such that the compound will have both primary and secondary amine functionality), m and n are numbers wherein m is greater than n (typically the ratio of m:n is from about 2:1 to about 500:1, more typically from about 40:1 to about 300:1 and most typically from about 85:1 to about 185:1) and the sum of n and m yield an aminosilicone compound with a viscosity of about 10 to about 100,000 cps at 25° (typically the sum of n and m is from about 5 to about 600, more typically from about 50 to about 400 and most typically from about 135 to about 275).

The preparation and properties of silicone compounds is discussed generally in *Silicones: Chemistry and Technology*, pp. 21-31 and 75-90 (CRC Press, Vulkan-Verlag, Essen, Germany, 1991) and in Harman et al. "Silicones". *Encyclopedia of Polymer Science and Engineering*, vol. 15, pp. (John Wiley & Sons, Inc. 1989), the disclosures of which are incorporated herein by reference. Preferred aminosilicone compounds are disclosed, for example in JP-047547 (J57161170) (Shinetsu Chem. Ind. KK). Particularly preferred aminosilicone compounds are the three of formula I wherein (1) $R^1$ and $R^8$ are methoxy, $R^2$, $R^3$, $R^4$, $R^5$, $R^6$, $R^9$, and $R^{10}$ are methyl, $R^7$ is N-aminoethyl-3-aminopropyl, m is about 135, and n is about 1.5, (2) $R^1$ and $R^8$ are methoxy, $R^2$, $R^3$, $R^4$, $R^5$, $R^6$, $R^9$, and $R^{10}$ are methyl, $R^7$ is N-aminoethyl-3-aminopropyl, m is about 270, and n is about 1.5, and (3) $R^1$ and $R^8$ are ethoxy, $R^2$, $R^3$, $R^4$, $R^5$, $R^6$, $R^9$, and $R^{10}$ are methyl, $R^7$ is 3-aminopropyl, m is about 135, and n is about 1.5. Other aminosilicone compounds include those wherein $R^1$, $R^2$, and $R^8$ are ethoxy, $R^3$ is 3-aminopropyl, $R^4$, $R^5$, $R^6$, $R^9$, and $R^{10}$ are methyl, m is about 8, and n is zero. Of course, for pure aminosilicone compounds, the numbers m and n will be integers, but for mixtures of compounds, m and n will be expressed as fractions or compound numbers which represent an average of the compounds present. Further, the formula above is not meant to imply a block copolymer structure, thus, the aminosilicone compound may have a random or block structure. Typically, at least about 50% by weight of the $R^4$, $R^5$, and $R^6$ groups will be methyl groups, more typically at least about 90% and even more typically about 100%.

The aminosilicone compound typically will be in the form of a liquid or viscous oil at room temperature.

The aminosilicones described below in the context of the soluble powder detergent compositions can be substituted for the aminosilicones described above.

II. Insoluble Carriers

While the aminosilicone can be used in certain compositions and methods of this invention alone or as an aqueous emulsion, the aminosilicone is preferably used in association with a water-insoluble solid carrier, for example, clays, natural or synthetic silicates, silica, resins, waxes, starches, ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. Useful inorganic agents comprise those of natural or synthetic mineral origin. Specific examples of carriers include diatomaceous earths, e.g. Celite® (Johns Manville Corp., Denver, Col.) and the smectite clays such as the saponites and the montmorillonite colloidal clays such as Veegum® and Van Gel® (Vanderbilt Minerals, Murray, Ky.), or Magnabrite® (American Colloid Co., Skokie, Ill.). Synthetic silicate carriers include the hydrous calcium silicate, Micro-Cel® and the hydrous magnesium silicate Celkate® (Seegot, Inc., Parsippany, N.J.). Inosilicates carriers such as the naturally-occurring calcium meta-silicates such as wollastonite, available as the NYAD® wollastonite series (Processed Minerals Inc., Willsboro, N.Y.) can also be mentioned. Synthetic sodium magnesium silicate clays, hectorite clays, and fumed silicas can also be mentioned as carriers. The carrier can be a very finely divided material of average particle diameter below 0.1 micron. Examples of such carriers are fumed silica and precipitated silica; these generally have a specific surface (BET) of above 40 $m^2/g$.

The clays that are particularly useful elements of the compositions and methods of this invention are those which cooperate with the silicone compounds to wash laundry better than would be expected from the actions of the individual components in detergent compositions. Such clays include the montmorillonite-containing clays which have swelling properties (in water) and which are of smectite structure. Typical of the smectite clays for use in the present invention is bentonite and typically the best of the bentonites are those which have a substantial swelling capability in water, such as the sodium bentonites, the potassium bentonites, or which are swellable in the presence of sodium or potassium ions, such as calcium bentonite. Such swelling bentonites are also known as western or Wyoming bentonites, which are essentially sodium bentonite. Other bentonites, such as calcium bentonite, are normally non-swelling. Among the preferred bentonites are those of sodium and potassium, which are normally swelling, and calcium and magnesium, which are normally non-swelling, but are swellable. Of these it is preferred to utilize calcium (with a source of sodium being present) and sodium bentonites. The bentonites employed are not limited to those produced in the United States of America, such as Wyoming bentonite, but also may be obtained from Europe, including Italy and Spain, as calcium bentonite, which may be converted to sodium bentonite by treatment with sodium carbonate, or may be employed as calcium bentonite. Typically, the clay will have a high montmorillonite content and a low content of cristobalite and/or quartz. Also, other montmorillonite-containing smectite clays of properties like those of the bentonites described may be substituted in whole or in part for the bentonites described herein, but typically the clay will be a sodium bentonite with high montmorillonite content and low cristobalite and quartz contents.

The swellable bentonites and similarly operative clays are of ultimate particle sizes in the micron range, e.g., 0.01 to 20 microns and of actual particle sizes less than 100 or 150 microns, such as 40 to 150 microns or 45 to 105 microns. Such size ranges also apply to the zeolite builders, which will be described later herein. The bentonite and other such suitable swellable clays may be agglomerated to larger particle sizes too, such as up to 2 or 3 mm. in diameter.

The ratio of aminosilicone compound to carrier will typically range from about 0.001 to about 2, more typically from about 0.02 to about 0.5, and most typically from about 0.1 to about 0.3.

III. Detergents

The Methods and Compositions of this Laundry Detergent Invention all Employ a Detergent and optionally, other functional ingredients. Examples of the detergents and other functional ingredients that can be used are disclosed in U.S. Ser. No. 08/726,437, filed Oct. 4, 1996, the disclosure of which is incorporated herein by reference. The detergent can be selected from a wide variety of surface active agents.

A. Nonionic Surfactants

Nonionic surfactants, including those having an HLB of from 5 to 17, are well known in the detergency art. Examples of such surfactants are listed in U.S. Pat. No. 3,717,630, Booth, issued Feb. 20, 1973, and U.S. Pat. No. 3,332,880, Kessler et al., issued Jul. 25, 1967, each of which is incorporated herein by reference. Nonlimiting examples of suitable nonionic surfactants which may be used in the present invention are as follows:

(1) The polyethylene oxide condensates of alkyl phenols. These compounds include the condensation products of alkyl phenols having an alkyl group containing from about 6 to 12 carbon atoms in either a straight chain or branched chain configuration with ethylene oxide, said ethylene oxide being present in an amount equal to 5 to 25 moles of ethylene oxide per mole of alkyl phenol. The alkyl substituent in such compounds can be derived, for example, from polymerized propylene, diisobutylene, and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by Rhone-Poulenc Inc. and Triton X-45, X-114, X-100, and X-102, all marketed by Union Carbide.

(2) The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol; and the condensation product of about 9 moles of ethylene oxide with coconut alcohol (a mixture of fatty alcohols with alkyl chains varying in length from 10 to 14 carbon atoms). Examples of commercially available nonionic surfactants in this type include Tergitol 15-S-9, marketed by Union Carbide Corporation, Neodol 45-9, Neodol 23-6.5, Neodol 45-7, and Neodol 45-4, marketed by Shell Chemical Company.

(3) The condensation products of ethylene oxide with a hydrophobic base formed by the condensation of propylene oxide with propylene glycol. The hydrophobic portion of these compounds typically has a molecular weight of from about 1500 to 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic surfactants, marketed by Wyandotte Chemical Corporation.

(4) The condensation products of ethylene oxide with the product resulting from the reaction of propylene oxide and ethylenediamine. The hydrophobic moiety of these products consists of the reaction product of ethylenediamine and excess propylene oxide, said moiety having a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

(5) Semi-polar nonionic detergent surfactants include water-soluble amine oxides containing one alkyl moiety of from about 10 to 18 carbon atoms and 2 moieties selected from the group consisting of alkyl groups and hydroxyalkyl groups containing from 1 to about 3 carbon atoms; water-soluble phosphine oxides containing one alkyl moiety of about 10 to 18 carbon atoms and 2 moieties selected from the group consisting of alkyl groups and hydroxyalkyl groups containing from about 1 to 3 carbons atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide detergent surfactants having the formula

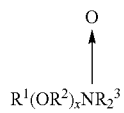

wherein $R^1$ is an alkyl, hydroxy alkyl, or alkyl phenyl group or mixtures thereof containing from about 8 to about 22 carbon atoms. $R^2$ is an alkylene or hydroxy alkylene group containing from 2 to 3 carbon atoms or mixtures thereof, x is from 0 to about 3 and each $R^2$ is an alkyl or hydroxy alkyl group containing from 1 to about 3 carbon atoms or a polyethylene oxide group containing from one to about 3 ethylene oxide groups and said $R^3$ groups can be attached to each other, e.g., through an oxygen or nitrogen atom to form a ring structure.

Preferred amine oxide detergent surfactants are $C_{10}$-$C_{18}$ alkyl dimethyl amine oxide, $C_8$-$C_{18}$ alkyl dihydroxy ethyl amine oxide, and $C_{8-12}$ alkoxy ethyl dihydroxy ethyl amine oxide.

Nonionic detergent surfactants (1)-(4) are conventional ethoxylated nonionic detergent surfactants and mixtures thereof can be used.

Preferred alcohol ethoxylate nonionic surfactants for use in the compositions of the liquid, powder, and gel applications are biodegradable and have the formula $$R(OC_2H_4)_nOH$$

wherein R is a primary or secondary alkyl chain of from about 8 to about 22, preferably from about 10 to about 20 carbon atoms and n is an average of from about 2 to about 12, particularly from about 2 to about 9. The nonionics have an HLB (hydrophilic-lipophilic balance) of from about 5 to about 17, preferably from about 6 to about 15. HLB is defined in detail in Nonionic Surfactants, by M. J. Schick, Marcel Dekker, Inc., 1966, pages 606-613, incorporated herein by reference. In preferred nonionic surfactants, n is from 3 to 7, Primary linear alcohol ethoxylates (e.g., alcohol ethoxylates produced from organic alcohols which contain about 20% 2-methyl branched isomers, commercially available from Shell Chemical Company under the trademark Neodol) are preferred from a performance standpoint.

Particularly preferred nonionic surfactants for use in liquid, powder, and gel applications include the condensation product of $C_{10}$ alcohol with 3 moles of ethylene oxide; the condensation product of tallow alcohol with 9 moles of ethylene oxide; the condensation product of coconut alcohol with 5 moles of ethylene oxide; the condensation product of coconut alcohol with 6 moles of ethylene oxide; the condensation product of $C_{12}$ alcohol with 5 moles of ethylene oxide; the condensation product of $C_{12-13}$ alcohol with 6.5 moles of ethylene oxide, and the same condensation product which is stripped so as to remove substantially all lower ethoxylate and nonethoxylated fractions; the condensation product of $C_{12-13}$ alcohol with 2.3 moles of ethylene oxide, and the same condensation product which is stripped so as to remove substantially all lower ethoxylated and nonethoxylated fractions; the condensation product of $C_{12-23}$ alcohol with 9 moles of ethylene oxide; the condensation product of $C_{14-15}$ alcohol with 2.25 moles of ethylene oxide; the condensation product of $C_{14-15}$ alcohol with 4 moles of ethylene oxide; the condensation product of $C_{14-15}$ alcohol with 7 moles of ethylene oxide; and the condensation product of $C_{14-15}$ alcohol with 9 moles of ethylene oxide. For bar soap applications, nonionic surfactants are preferably solids at room temperature with a melting point above about 25° C., preferably above about 30° C. Bar compositions of the present invention made with lower melting nonionic surfactants are generally too soft, not meeting the bar firmness requirements of the present invention.

Also, as the level of nonionic surfactant increases, i.e., above about 20% by weight of the surfactant, the bar can generally become oily.

Examples of nonionic surfactants usable herein, but not limited to bar applications, include fatty acid glycerine and polyglycerine esters, sorbitan sucrose fatty acid esters, polyoxyethylene alkyl and alkyl allyl ethers, polyoxyethylene lanolin alcohol, glycerine and polyoxyethylene glycerine fatty acid esters, polyoxyethylene propylene glycol and sorbitol fatty acid esters, polyoxyethylene lanolin, castor oil or hardened castor oil derivatives, polyoxyethylene fatty acid amides, polyoxyethylene alkyl amines, alkylpyrrolidone, glucamides, alkylpolyglucosides, and mono- and dialkanol amides.

Typical fatty acid glycerine and polyglycerine esters, as well as typical sorbitan sucrose fatty acid esters, fatty acid amides, and polyethylene oxide/polypropylene oxide block copolymers are disclosed by U.S. Pat. No. 5,510,042, Hartman et al, incorporated herein by reference.

The castor oil derivatives are typically ethoxylated castor oil. It is noted that other ethoxylated natural fats, oils or waxes are also suitable.

Polyoxyethylene fatty acid amides are made by ethoxylation of fatty acid amides with one or two moles of ethylene oxide or by condensing mono- or diethanol amines with fatty acid.

Polyoxyethylene alkyl amines include those of formula: RNH—(CH$_2$CH$_2$O)$_n$—H, wherein R is C$_6$ to C$_{22}$ alkyl and n is from 1 to about 100.

Monoalkanol amides include those of formula: RCONHR$^1$OH, wherein R is C$_6$-C$_{22}$ alkyl and R$^1$ is C$_1$ to C$_6$ alkylene. Dialkanol amides are typically mixtures of:

diethanolamide: RCON(CH$_2$CH$_2$OH)$_2$;
amide ester: RCON(CH$_2$CH$_2$OH)—CH$_2$CH$_2$OOCR;
amine ester: RCOOCH$_2$CH$_2$NHCH$_2$CH$_2$OH; and
amine soap: RCOOH$_2$N(CH$_2$CH$_2$OH)$_2$, wherein R in the above formulas is an alkyl of from 6 to 22 carbon atoms.

Examples of preferred but not limiting surfactants for detergent bar products are the following:

Straight-Chain Prima Alcohol Alkoxylates

The deca-, undeca-, dodeca-, tetradeca-, and pentadeca-ethoxylates of n-hexadecanol, and n-hexadecanol, and n-octadecanol having an HLB within the range recited herein are useful nonionics in the context of this invention. Exemplary ethoxylated primary alcohols useful herein as the conventional nonionic surfactants of the compositions are n-C$_{18}$EO(10); n-C$_{14}$EO(13); and n-C$_{10}$EO(11). The ethoxylates of mixed natural or synthetic alcohols in the "tallow" chain length range are also useful herein. Specific examples of such materials include tallow-alcohol-EO(11), tallow-alcohol-EO(18), and tallow-alcohol-EO(25).

Straight-Chain Secondary Alcohol Alkoxylates

The deca-, undeca-, dodeca-, tetradeca-, pentadeca-, octadeca-, and nonadeca-ethoxylates of 3-hexadecanol, 2-octadecanol, 4-eicosanol, and 5-eicosanol having an HLB within the range recited herein are useful conventional nonionics in the context of this invention. Exemplary ethoxylated secondary alcohols useful herein are 2-C$_{16}$EO(11); 2-C$_{20}$EO(11); and 2-C$_{16}$EO(14).

Alkyl Phenol Alkoxylates

As in the case of the alcohol alkoxylates, the hexa- through octadeca-ethoxylates of alkylated phenols, particularly monohydric alkylphenols, having an HLB within the range recited herein are useful as conventional nonionic surfactants in the instant compositions. The hexa-through octadeca-ethoxylates of p-tridecylphenol, m-pentadecylphenol, and the like, are useful herein. Exemplary ethoxylated alkylphenols useful in the mixtures herein are: p-tridecylphenol EO(11) and p-pentadecylphenol EO(18). Especially preferred is Nonyl Nonoxynol-49 known as Igepal DM-880 from Rhone-Poulenc Inc.

As used herein and as generally recognized in the art, a phenylene group in the nonionic formula is the equivalent of an alkylene group containing from 2 to 4 carbon atoms. For present purposes, nonionics containing a phenylene group are considered to contain an equivalent number of carbon atoms calculated, as the sum of the carbon atoms in the alkyl group plus about 3.3 carbon atoms for each phenylene group.

Olefinic Alkoxylates

The alkenyl alcohols, both primary and secondary, and alkenyl phenols corresponding to those disclosed immediately hereinabove can be ethoxylated to an HLB within the range recited herein and used as the conventional nonionic surfactants of the instant compositions.

Branched Chain Alkoxylates

Branched chain primary and secondary alcohols which are available can be ethoxylated and employed as conventional nonionic surfactants in compositions herein.

The above ethoxylated nonionic surfactants are useful in the present compositions alone or in combination, and the term "nonionic surfactant" encompasses mixed nonionic surface active agents.

Alkylpolysaccharides

Still further suitable nonionic surfactants of this invention include alkylpolysaccharides, preferably alkylpolyglycosides of the formula:

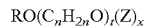

wherein
Z is derived from glycose;
R is a hydrophobic group selected from the group consisting of a C$_{10}$-C$_{18}$, preferably a C$_{12}$-C$_{14}$, alkyl group, alkyl phenyl group, hydroxyalkyl group, hydroxyalkylphenyl group, and mixtures thereof;
n is 2 or 3; preferably 2;
t is from 0 to 10; preferably 0; and
x is from 1.5 to 8; preferably 1.5 to 4; more preferably from 1.6 to 2.7.

These surfactants are disclosed in U.S. Pat. Nos. 4,565,647, Llenado, issued Jan. 21, 1986; 4,536,318, Cook et al., issued Aug. 20, 1985; 4,536,317, Llenado et al., issued Aug. 20, 1985; 4,599,188 Llenado, issued Jul. 8, 1986; and 4,536,319, Payne, issued Aug. 20, 1985; all of which are incorporated herein by reference.

The compositions of the present invention can also comprise mixtures of the above nonionic surfactants.

A thorough discussion of nonionic surfactants for detergent bar and liquid products is presented by U.S. Pat. Nos. 5,510,042, Hartman et al., and 4,483,779, Llenado, et al., incorporated herein by reference.

B. Anionic Surfactants

Anionic surfactants include any of the known hydrophobes attached to a carboxylate, sulfonate, sulfate or phosphate polar, solubilizing group including salts. Salts may be the sodium, potassium, ammonium and amine salts of such surfactants. Useful anionic surfactants can be organic sulfuric reaction products having in their molecular structure an alkyl group containing from about 8 to about 22 carbon atoms and a sulfonic acid or sulfuric acid ester group, or mixtures thereof (Included in the term "alkyl" is the alkyl portion of acyl groups.) Examples of this group of synthetic detersive surfactants which can be used in the present invention are the alkyl sulfates, especially those obtained by sulfating the higher alcohols (C$_8$-C$_{18}$ carbon atoms) produced from the glycerides of tallow or coconut oil; and alkyl benzene sulfonates.

Other useful anionic surfactants herein include the esters of alpha-sulfonated fatty acids preferably containing from about 6 to 20 carbon atoms in the ester group; 2-acyloxyalkane-1-sulfonic acids preferably containing from about 2 to 9 carbon atoms in the acyl group and from about 9 to about 23 carbon atoms in the alkane moiety; alkyl ether sulfates preferably containing from about 10 to 20 carbon atoms in the alkyl group and from about 1 to 30 moles of ethylene oxide; olefin sulfonates preferably containing from about 12 to 24 carbon atoms; and beta-alkyloxy alkane sulfonates preferably containing from about 1 to 3 carbon atoms in the alkyl group and from about 8 to 20 carbon atoms in the alkane moiety.

Anionic surfactants based on the higher fatty acids, i.e., "soaps" are useful anionic surfactants herein. Higher fatty acids containing from about 8 to about 24 carbon atoms and preferably from about 10 to about 20 carbon atoms and the coconut and tallow soaps can also be used herein as corrosion inhibitors.

Preferred water-soluble anionic organic surfactants herein include linear alkyl benzene sulfonates containing from about 10 to about 18 carbon atoms in the alkyl group; branched alkyl benzene sulfonates containing from about 10 to about 18 carbon atoms in the alkyl group; the tallow range alkyl sulfates; the coconut range alkyl glyceryl sulfonates; alkyl ether (ethoxylated) sulfates wherein the alkyl moiety contains from about 12 to 18 carbon atoms and wherein the average degree of ethoxylation varies between 1 and 12, especially 3 to 9; the sulfated condensation products of tallow alcohol with from about 3 to 12, especially 6 to 9, moles of ethylene oxide; and olefin sulfonates containing from about 14 to 16 carbon atoms.

Specific preferred anionics for use herein include: the linear $C_{10}$-$C_{14}$ alkyl benzene sulfonates (LAS); the branched $C_{10}$-$C_{14}$ alkyl benzene sulfonates (ABS); the tallow alkyl sulfates, the coconut alkyl glyceryl ether sulfonates; the sulfated condensation products of mixed $C_{10}$-$C_{18}$ tallow alcohols with from about 1 to about 14 moles of ethylene oxide; and the mixtures of higher fatty acids containing from 10 to 18 carbon atoms.

It is to be recognized that any of the foregoing anionic surfactants can be used separately herein or as mixtures. Moreover, commercial grades of the surfactants can contain non-interfering components which are processing by-products. For example, commercial alkaryl sulfonates, preferably $C_{10}$-$C_{14}$, can comprise alkyl benzene sulfonates, alkyl toluene sulfonates, alkyl naphthalene sulfonates and alkyl polybenzenoid sulfonates. Such materials and mixtures thereof are fully contemplated for use herein.

Other examples of the anionic surfactants used herein include fatty acid soaps, ether carboxylic acids and salts thereof alkane sulfonate salts, α-olefin sulfonate salts, sulfonate salts of higher fatty acid esters, higher alcohol sulfate ester or ether ester salts, alkyl, preferably higher alcohol phosphate ester and ether ester salts, and condensates of higher fatty acids and amino acids.

Fatty acid soaps include those having the formula: R—C(O)OM, wherein R is $C_6$ to $C_{22}$ alkyl and M is preferably sodium.

Salts of ether carboxylic acids and salts thereof include those having the formula: R—(OR$^1$)$_n$—OCH$_2$C(O)OM, wherein R is $C_6$ to $C_{22}$ alkyl, R$^1$ is $C_2$ to $C_{10}$, preferably $C_2$ alkyl, and M is preferably sodium.

Alkane sulfonate salts and α-olefin sulfonate salts have the formula: R—SO$_3$M, wherein R is $C_6$ to $C_{22}$ alkyl or α-olefin, respectively, and M is preferably sodium.

Sulfonate salts of higher fatty acid esters include those having the formula:

RC(O)O—R$^1$—SO$_3$M, wherein R is $C_{12}$ to $C_{22}$ alkyl, R$^1$ is $C_1$ to $C_{18}$ alkyl and M is preferably sodium.

Higher alcohol sulfate ester salts include those having the formula:

RC(O)O—R$^1$—OSO$_3$M, wherein R is $C_{12}$-$C_{22}$ alkyl, R$^1$ is $C_1$-$C_{18}$ hydroxyalkyl, M is preferably sodium.

Higher alcohol sulfate ether ester salts include those having the formula:

RC(O)(OCH$_2$CH$_2$)$_x$—R$^1$—OSO$_3$M, wherein R is $C_{12}$-$C_{22}$ alkyl, R$^1$ is $C_1$-$C_{18}$ hydroxyalkyl, M is preferably sodium and x is an integer from 5 to 25.

Higher alcohol phosphate ester and ether ester salts include compounds of the formulas:

R—(OR$^1$)$_n$—OPO(OH)(OM);

(R—(OR$^1$)$_n$—O)$_2$PO(OM); and (R—(OR$^1$)$_n$—O)$_3$—PO, wherein R is alkyl or hydroxyalkyl of 12 to 22 carbon atoms, R$^1$ is $C_2H_4$, n is an integer from 5 to 25, and M is preferably sodium.

Other anionic surfactants herein are sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

C. Cationic Surfactants

Preferred cationic surfactants of the present invention are the reaction products of higher fatty acids with a polyamine selected from the group consisting of hydroxyalkylalkylenediamines and dialkylenetriamines and mixtures thereof.

A preferred component is a nitrogenous compound selected from the group consisting of:
(i) the reaction product mixtures of higher fatty acids with hydroxyalkylalkylenediamines in a molecular ratio of about 2:1, said reaction product containing a composition having a compound of the formula:

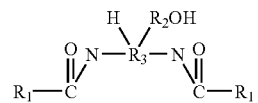

wherein R$_1$ is an acyclic aliphatic $C_{15}$-$C_{21}$ hydrocarbon group and R$_2$ and R$_3$ are divalent $C_1$-$C_3$ alkylene groups; commercially available as Mazamide 6 from PPG;
(ii) the reaction product of higher fatty acids with dialkylenetriamines in a molecular ratio of about 2:1; said reaction product containing a composition having a compound of the formula:

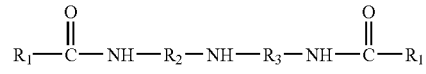

wherein R$_1$, R$_2$ and R$_3$ are as defined above; and mixtures thereof.

Another preferred component is a cationic nitrogenous salt containing one long chain acyclic aliphatic $C_{15}$-$C_{22}$ hydrocarbon group selected from the group consisting of:
(i) acyclic quaternary ammonium salts having the formula:

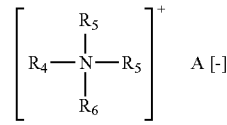

wherein $R_4$ is an acyclic aliphatic $C_{15}$-$C_{22}$ hydrocarbon group, $R_5$ and $R_6$ are $C_1$-$C_4$ saturated alkyl or hydroxyalkyl groups, and A [-] is an anion, especially as described in more detail hereinafter, examples of these surfactants are sold by Sherex Chemical Company tinder the Adgen trademarks;

(ii) substituted imidazolinium salts having the formula:

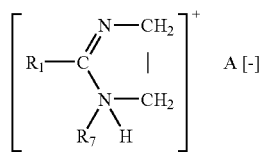

wherein $R_1$ is an acyclic aliphatic $C_{15}$-$C_{21}$ hydrocarbon group, $R_7$ is a hydrogen or a $C_1$-$C_4$ saturated alkyl or hydroxyalkyl group, and A [-] is an anion;

(iii) substituted imidazolinium salts having the formula:

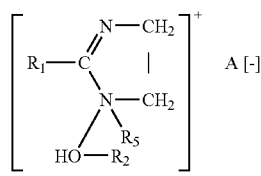

wherein $R_2$ is a divalent $C_1$-$C_3$ alkylene group and $R_1$, $R_5$ and A [-] are as defined above; an example of which is commercially available under the Monaquat ISIES trademark from Mona Industries, Inc.;

(iv) alkylpyridinium salts having the formula:

wherein $R_4$ is an acyclic aliphatic $C_{16}$-$C_{22}$ hydrocarbon group and A [-] is an anion; and (v) alkanamide alkylene pyridinium salts having the formula:

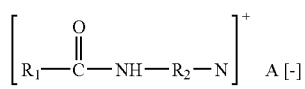

wherein $R_1$ is an acyclic aliphatic $C_{15}$-$C_{21}$ hydrocarbon group, $R_2$ is a divalent $C_1$-$C_3$ alkylene group, and A [-] is an ion group; and mixtures thereof.

Another class of preferred cationic nitrogenous salts having two or more long chain acyclic aliphatic $C_{15}$-$C_{22}$ hydrocarbon groups or one said group and an arylalkyl group are selected from the group consisting of:

(i) acyclic quaternary ammonium salts having the formula:

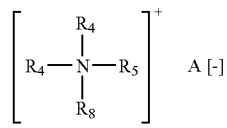

wherein each $R_4$ is an acyclic aliphatic $C_{15}$-$C_{22}$ hydrocarbon group, $R_5$ is a $C_1$-$C_4$ saturated alkyl or hydroxyalkyl group, $R_8$ is selected from the group consisting of $R_4$ and $R_5$, groups, and A [-] is an anion defined as above; examples of which are commercially available from Sherex Company under the Adgen trademarks;

(ii) diamido quaternary ammonium salts having the formula:

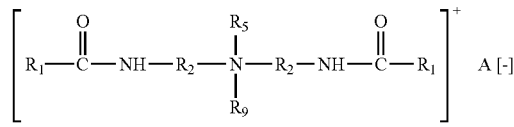

wherein each $R_1$ is an acyclic aliphatic $C_{15}$-$C_{21}$ hydrocarbon group, $R_2$ is a divalent alkylene group having 1 to 3 carbon atoms, $R_5$ and $R_9$, are $C_1$-$C_4$ saturated alkyl or hydroxyalkyl groups, and A [-] is an anion; examples of which are sold by Sherex Chemical Company under the Varisoft trademark;

(iii) diamino alkoxylated quaternary ammonium salts having the formula:

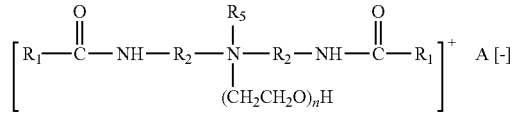

wherein n is equal to 1 to about 5, and $R_1$, $R_2$, $R_5$, and A [-] are as defined above;

(iv) quaternary ammonium compounds having the formula:

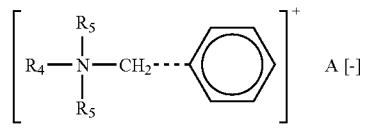

wherein each $R_4$ is an acyclic aliphatic $C_{15}$-$C_{22}$ hydrocarbon group, each $R_5$ is a $C_1$-$C_4$ saturated alkyl or hydroxyalkyl group, and A [-] is an anion; examples of such surfactants are available from Onyx Chemical Company under the Ammonyx® 490 trademark;

(v) substituted imidazolinium salts having the formula:

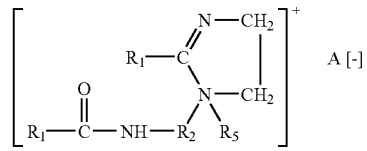

wherein each $R_1$ is an acyclic aliphatic $C_{15}$-$C_{21}$ hydrocarbon group, $R_2$ is a divalent alkylene group having 1 to 3 carbon atoms, and $R_5$ and A [-] are as defined above; examples are commercially available from Sherex Chemical Company under the Varisoft 475 and Varisoft 445 trademarks; and (vi) substituted imidazolinium salts having the formula:

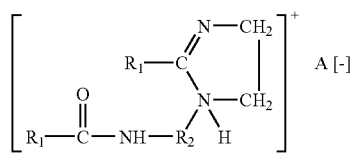

wherein $R_1$, $R_2$ and A—are as defined above; and mixtures thereof.

The more preferred cationic conventional surfactant is selected from the group consisting of an alkyltrimethylammonium salt, a dialkyldimethylammonium salt, an alkyldimethylbenzylammonium salt, an alkylpyridinium salt, an alkylisoquinolinium salt, benzethonium chloride, and an acylamino acid cationic surfactant.

Anion A

In the cationic nitrogenous salts herein, the anion A [-] provides electrical neutrality. Most often, the anion used to provide electrical neutrality in these salts is a halide, such as chloride, bromide, or iodide. However, other anions can be used, such as methylsulfate, ethylsulfate, acetate, formate, sulfate, carbonate, and the like. Chloride and methylsulfate are preferred herein as anion A.

Cationic surfactants are commonly employed as fabric softeners in compositions added during the rinse cycle of clothes washing. Many different types of fabric conditioning agents have been used in rinse cycle added fabric conditioning compositions as disclosed by U.S. Pat. No. 5,236,615, Trinh et al. and U.S. Pat. No. 5,405,542, Trinh et al., both patents herein incorporated by reference in their entirety. The most favored type of agent has been the quaternary ammonium compounds. Many such quaternary ammonium compounds are disclosed for example, by U.S. Pat. No. 5,510,042, Hartman et al. incorporated herein by reference in its entirety. These compounds may take the form of noncyclic quaternary ammonium salts having preferably two long chain alkyl groups attached to the nitrogen atoms. Additionally, imidazolinium salts have been used by themselves or in combination with other agents in the treatment of fabrics as disclosed by U.S. Pat. No. 4,127,489, Pracht, et al. incorporated herein by reference in its entirety. U.S. Pat. No. 2,874,074, Johnson discloses using imidazolinium salts to condition fabrics; and U.S. Pat. No. 3,681,241, Rudy, and U.S. Pat. No. 3,033,704, Sherrill et al. disclose fabric conditioning compositions containing mixtures of imidazolinium salts and other fabric conditioning agents. These patents are incorporated herein by reference in their entirety.

D. Amphoteric Surfactants

Amphoteric surfactants have a positive or negative charge or both on the hydrophilic part of the molecule in acidic or alkaline media.

Examples of the amphoteric surfactants which can be used herein include amino acid, betaine, sultaine, phosphobetaines, imidazolinium derivatives, soybean phospholipids, and yolk lecithin. Examples of suitable amphoteric surfactants include the alkali metal, alkaline earth metal, ammonium or substituted ammonium salts of alkyl amphocarboxy glycinates and alkyl iamphocarboxypropionates, alkyl amphodipropionates, alkyl amphodiacetates, alkyl amphoglycinates and alkyl amphopropionates wherein alkyl represents an alkyl group having 6 to 20 carbon atoms. Other suitable amphoteric surfactants include alkyliminopropionates, alkyl iminodipropionates and alkyl amphopropylsulfonates having between 12 and 18 carbon atoms, alkylbetaines and amidopropylbetaines and alkylsultainesi and alkylamidopropylhydroxy sultaines wherein alkyl represents an alkyl group having 6 to 20 carbon atoms are especially preferred.

Particularly useful amphoteric surfactants include both mono and dicarboxylates such as those of the formulae:

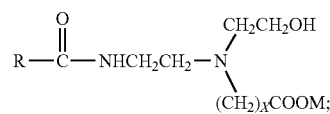
(A)

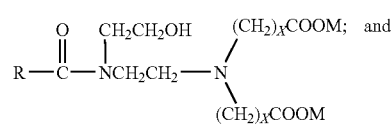
(B)

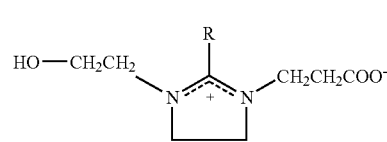
(C)

wherein R is an alkyl group of 6-20 carbon atoms, x is 1 or 2 and M is hydrogen or sodium. Mixtures of the above structures are particularly preferred.

Other formulae for the above amphoteric surfactants include the following:

Alkyl Betaines

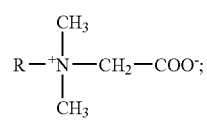
(D)

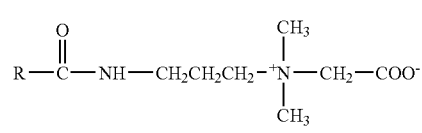
(E)

Amidopropyl betaines

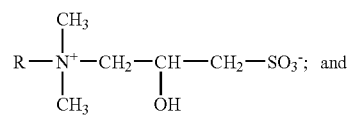
(F)

Alkyl sultaines

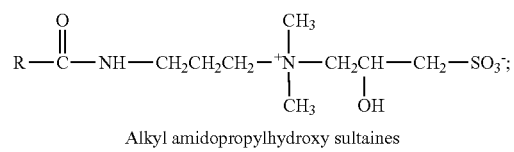
(G)

Alkyl amidopropylhydroxy sultaines where R is an alkyl group of 6-20 carbon atoms and M is hydrogen or sodium.

Of the above amphoteric surfactants, particularly preferred are the alkali salts of alkyl amphocarboxyglycinates and alkyl amphocarboxypropionates, alkyl amphodipropionates, alkyl amphodiacetates, alkyl amphoglycinates, alkyl amphopropyl sulfonates and alkyl amphopropionates wherein alkyl represents an alkyl group having 6 to 20 carbon atoms. Even more preferred are compounds wherein the alkyl group is derived from coconut oil or is a lauryl group, for example, cocoamphodipropionate. Such cocoamphodipropionate surfactants are commercially sold under the trademarks Miranol C2M-SF CONC. and Miranol FBS by Rhone-Poulenc Inc.

Other commercially useful amphoteric surfactants are available from Rhone-Poulenc Inc. and include:

--- cocoamphoacetate (sold under the trademarks MIRANOL CM CONC. and MIRAPON FA),
cocoamphopropionate (sold under the trademarks MIRANOL CM-SF CONC. and MIRAPON FAS),
cocoamphodiacetate (sold under the trademarks MIRANOL C2M CONC. and MIRAPON FB),
lauroamphoacetate (sold under the trademarks MIRANOL HM CONC. and MIRAPON LA),
lauroamphodiacetate (sold under the trademarks MIRANOL H2M CONC. and MIRAPON LB),
lauroamphodipropionate (sold under the trademarks MIRANOL H2M SF CONC. AND MIRAPON LBS),
lauroamphodiacetate obtained from a mixture of lauric and myristic acids (sold under the trademark MIRANOL BM CONC.), and
cocoamphopropyl sulfonate (sold under the trademark MIRANOL CS CONC.)

---

Somewhat less preferred are:

--- caproamphodiacetate (sold under the trademark MIRANOL S2M CONC.),
caproamphoacetate (sold under the trademark MIRANOL SM CONC.),
caproamphodipropionate (sold under the trademark MIRANOL S2M-SF CONC.), and
stearoamphoacetate (sold under the trademark MIRANOL DM).

---

E. Gemini Surfactants

Gemini surfactants form a special class of surfactant. These surfactants have the general formula:

A-G-A$^1$ and get their name because they comprise two surfactant moieties (A,A$^1$) joined by a spacer (G), wherein each surfactant moiety (A,A,$^1$) has a hydrophilic group and a hydrophobic group. Generally, the two surfactant moieties (A,A$^1$) are twins, but they can be different.

The gemini surfactants are advantageous because they have low critical micelle concentrations (cmc) and, thus, lower the cmc of solutions containing both a gemini surfactant and a conventional surfactant. Lower cmc causes better solubilization and increased detergency at lower surfactant use levels and unexpectedly enhances the deposition of the soil release polymers as claimed by this invention with demonstrated results to follow herein. Soil removal agents adhere to the fabric being laundered, much better than when mixed with only non-gemini, conventional surfactants.

Also, the gemini surfactants result in a low $pC_{20}$ value and low Krafft points. The $pC_{20}$ value is a measure of the surfactant concentration in the solution phase that will reduce the surface tension of the solvent by 20 dynes/cm. It is a measure of the tendency of the surfactant to adsorb at the surface of the solution. The Krafft point is the temperature at which the surfactant's solubility equals the cmc. Low Krafft points imply better solubility in water, and lead to greater latitude in making formulations.

A number of the gemini surfactants are reported in the literature, see for example, Okahara et al., J. Japan Oil Chem. Soc. 746 (Yukagaku) (1989); Zhu et al., 67 JAOCS 7,459 (July 1990); Zhu et al., 68 JAOCS 7,539 (1991); Menger et al., J. Am. Chemical Soc. 113, 1451 (1991); Masuyama et al., 41 J. Japan Chem. Soc. 4,301 (1992); Zhu et al., 69 JAOCS 1,30 (January 1992); Zhu et al., 69 JAOCS 7,626 July 1992); Menger et al., 115 J. Am. Chem. Soc. 2, 10083 (1993); Rosen, Chemtech 30 (March 1993); and Gao et al., 71 JAOCS 7,771 (July 1994), all of this literature incorporated herein by reference.

Also, gemini surfactants are disclosed by U.S. Pat. Nos. 2,374,354, Kaplan; 2,524,218, Bersworth; 2,530,147 Bersworth (two hydrophobic tails and three hydrophilic heads); 3,244,724, Guttmann; 5,160,450, Okahara, et al., all of which are incorporated herein by reference.

The gemini surfactants may be anionic, nonionic, cationic or amphoteric. The hydrophilic and hydrophobic groups of each surfactant moiety (A,A$^1$) may be any of those known to be used in conventional surfactants having one hydrophilic group and one hydrophobic group.

For example, a typical nonionic gemini surfactant, e.g., a bis-polyoxyethylene alkyl ether, would contain two polyoxyethylene alkyl ether moieties.

Each moiety would contain a hydrophilic group, e.g., polyethylene oxide, and a hydrophobic group, e.g., an alkyl chain.

Gemini surfactants specifically useful in the present invention include gemini anionic or nonionic surfactants of the formulae:

II.

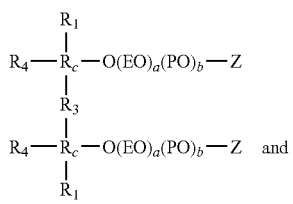

and

III.

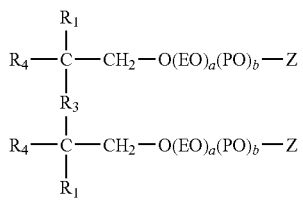

wherein $R_1$ represents aryl, preferably phenyl.

$R_1$, $R_3$, $R_4$, Y, Z, a and b are as defined above.

More specifically, these compounds comprise:

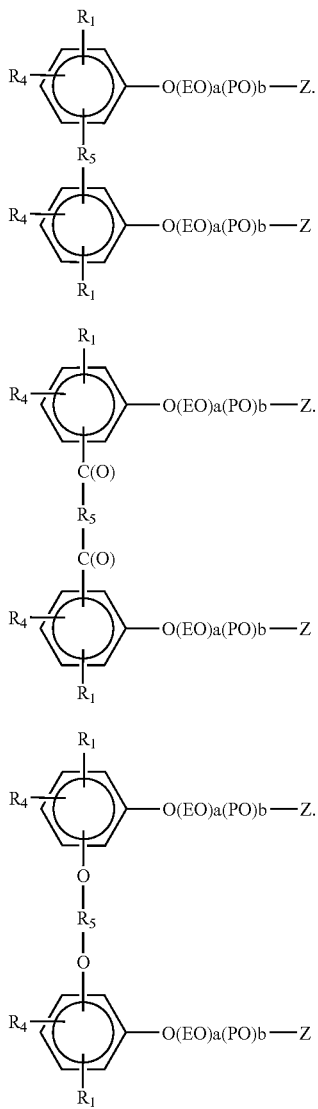
IV

V

VI wherein $R_1$, $R_4$, $R_5$, Z, a, and b are as defined hereinbefore.

The primary hydroxyl group of these surfactants can be readily phosphated, sulfated or carboxylated by standard techniques.

The compounds included in Formula II can be prepared by a variety of synthetic routes. For instance, the compounds of Formula IV can be prepared by condensing a monoalkyl phenol with paraformaldehyde in the presence of an acid catalyst such as acetic acid. The compounds of Formula V can be synthesized by a Lewis acid catalyzed reaction of an alkylphenol with a dicarboxylic acid, e.g., terephthalic acid.

The compounds of Formula II are more fully described in copending application U.S. Ser. No. 60/009,075 filed Dec. 21, 1995, the entire disclosure of which is incorporated herein by reference.

A class of gemini surfactants that can be used in providing the improved emulsions which are operable at lower concentrations as disclosed in the present invention include a group of amphoteric, and cationic quaternary surfactants comprising compounds of the formula:

VII.
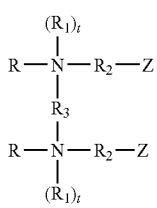

wherein R, t, and Z are as defined hereinbefore. $R_1$ is as defined before and includes the $[-(EO)_a(PO)_b O—]H$ moiety. $R_2$ is as defined before, however, D includes the following moieties: $—N(R_6)—C(O)—R_5—CH_2O—$ and $—N(R_6)—C(O)—R_5—N(R_6)—R_4—$. When t is zero, the compounds are amphoteric and when t is 1, the compounds are cationic quaternary compounds. $R_3$ is selected from the group consisting of a bond, $C_1$-$C_{10}$ alkyl, and $—R_8$-$D_1$-$R_8$— wherein $D_1$, $R_5$, $R_6$, a, b, and $R_8$, are as defined above (except $R_8$ is not $—OR_5O—$).

Preferably, the compounds of Formula VII comprise:

VIII.
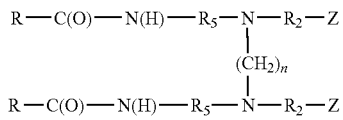

wherein R, $R_2$, $R_5$ and Z are as defined above and n equals a number from about 2 to about 10. More particularly, the compounds of Formula VII comprise:

IX.
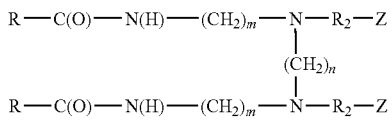

wherein R, $R_2$, $R_5$, Z, and n are as defined hereinbefore; and m independently equals a number between about 2 and about 10.

Representative compounds of Formula VII include:

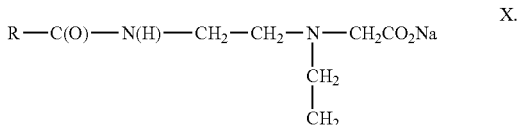 X.

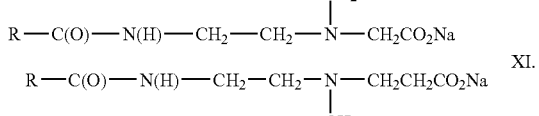 XI.

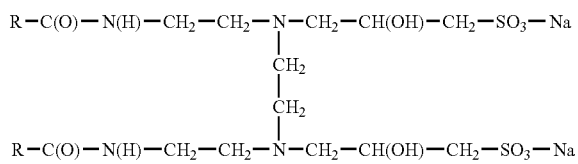

XII

While the compounds of Formulae VII-XII can be prepared by a variety of synthetic routes, it has been found that they can be produced particularly effectively by a process which utilizes a polyamine reactant having at least four amino groups of which two are terminal primary amines such as triethylene tetramine. These processes are more fully set forth in copending application "Amphoteric Surfactants Having Multiple Hydrophobic and Hydrophilic Groups", U.S. Ser. No. 08/292,993 filed Aug. 19, 1994, the entire disclosure of which is incorporated herein by reference.

Another group of gemini surfactants which have been found to provide the low concentration emulsions of this invention are the cyclic cationic quaternary surfactants of the formula:

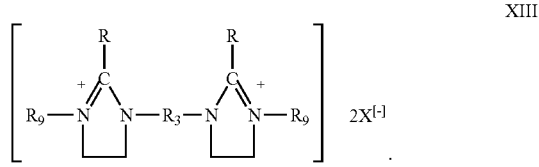

XIII wherein R and $R_3$ are as identified hereinbefore in formula VII; $R_9$ is independently a $C_1$-$C_{10}$ alkyl or alkylaryl; and X represents a counterion such as an anion illustrated by halogen (Cl, Br, and I), alkylsulfate such as methyl or ethylsulfate, alkylphosphate such as methylphosphate, and the like.

Preferably, the compounds used in the present invention comprise those of Formula XIII in which $R_3$ is a $C_2$-$C_4$ alkyl, most preferably ethyl, $R_9$ is a lower alkyl of from 1 to about 4 carbon atoms, most preferably methyl; and X is halogen or methylsulfate.

The compounds of Formula XIII can be prepared by a variety of synthetic routes though it has been found that they can be produced particularly effectively by quaternizing a bisimidazoline prepared by a process disclosed and claimed in copending application "Amphoteric Surfactants having Multiple Hydrophobic and Hydrophilic Groups", U.S. Ser. No. 08/292,993 filed Aug. 19, 1994 wherein a polyamine reactant having at least four amino groups, of which two are terminal primary amine groups, is reacted with an acylating agent such as a carboxylic acid, ester, and the naturally occurring triglyceride esters thereof or acid chlorides thereof in an amount sufficient to provide at least about 1.8 fatty acid groups [$R_1C(O)$—] per polyamine to provide the bisimidazoline.

Also included in the gemini surfactants useful in this invention are those of the formula:

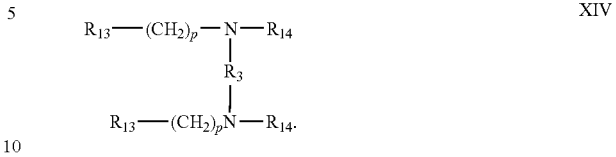

XIV wherein $R_{13}$ is a sugar moiety, e.g., a monosaccharide, desaccharide, or polysaccharide such as glucose; or a polyhydroxy compound such as glycerol; p is independently 0 to 4; $R_3$ is as defined above in formula VII; and $R_{14}$ is a $C_1$-$C_{22}$ alkyl or —$C(O)R_4$ wherein $R_4$ is as described above.

Some of the compounds such as those described above are set forth more fully in U.S. Pat. No. 5,534,197 which description is incorporated herein by reference.

In the compounds used in the invention, many of the moieties can be derived from natural sources which will generally contain mixtures of different saturated and unsaturated carbon chain lengths. The natural sources can be illustrated by coconut oil or similar natural oil sources such as palm kernel oil, palm oil, osya oil, rapeseed oil, castor oil or animal fat sources such as herring oil and beef tallow. Generally, the fatty acids from natural sources in the form of the fatty acid or the triglyceride oil can be a mixture of alkyl radicals containing from about 5 to about 22 carbon atoms. Illustrative of the natural fatty acids are caprylic ($C_8$), capric ($C_{10}$), lauric ($C_{12}$), myristic ($C_{14}$), palmitic ($C_{16}$), stearic ($C_{18}$), oleic ($C_{18}$, monounsaturated), linoleic ($C_{18}$, diunsaturated), linolenic ($C_{18}$, triunsaturated), ricinoleic ($C_{18}$, monounsaturated) arachidic ($C_{20}$), gadolic ($C_{20}$, monounsaturated), behenic ($C_{22}$) and erucic ($C_{22}$). These fatty acids can be used per se, as concentrated cuts or as fractionations of natural source acids. The fatty acids with even numbered carbon chain lengths are given as illustrative though the odd numbered fatty acids can also be used. In addition, single carboxylic acids, e.g., lauric acid, or other cuts, as suited for the particular application, may be used.

Where desired, the surfactants used in the present invention can be oxyalkylated by reacting the product with an alkylene oxide according to known methods, preferably in the presence of an alkaline catalyst. The free hydroxyl groups of the alkoxylated derivative can then be sulfated, phosphated or acylated using normal methods such as sulfation with sulfamic acid or sulfur trioxide-pyridine complex, or acylation with an acylating agent such as a carboxylic acid, ester, and the naturally occurring triglyceride esters thereof.

For alkylation conditions and commonly used alkylating agents, see Amphoteric Surfactants Vol. 12, Ed. B. R. Bluestein and C. L. Hilton, *Surfactant Science Series* 1982, pg. 17 and references cited therein, the disclosures of which are incorporated herein by reference.

For sulfation and phosphation, see Surfactant Science Series, Vol. 7, Part I, S. Shore & D. Berger, page 135, the disclosure of which is incorporated herein by reference. For phosphating review, see Surfactant Science Series, Vol. 7, Part II, E. Jungermann & H. Silbertman, page 495, the disclosure of which is incorporated herein by reference.

The surfactant compositions of the invention are extremely effective in aqueous solution at low concentrations as defined herein. The surfactants of the invention can be used in any amount needed for a particular application which can be easily determined by a skilled artisan without undue experimentation.

IV. Auxiliary Detergent Ingredients

A. Detergency Builders

Compositions of the present invention may include detergency builders selected from any of the conventional inorganic and organic water-soluble builder salts, including neutral or alkaline salts, as well as various water-insoluble and so-called "seeded" builders.

Builders are preferably selected from the various water-soluble, alkali metal, ammonium or substituted ammonium phosphates, polyphosphates, phosphonates, polyphosphonates, carbonates, silicates, borates, polyhydroxysulfonates, polyacetates, carboxylates, and polycarboxylates. Most preferred are the alkali metal, especially sodium, salts of the above.

Specific examples of inorganic phosphate builders are sodium and potassium tripolyphosphate, pyrophosphate, polymeric metaphate having a degree of polymerization of from about 6 to 21, and orthophosphate. Examples of polyphosphonate builders are the sodium and potassium salts of ethylene-1,1-diphosphonic acid, the sodium and potassium salts of ethane 1-hydroxy-1,1-diphosphonic acid and the sodium and potassium salts of ethane, 1,1,2-triphosphonic acid.

Examples of nonphosphorus, inorganic builders are sodium and potassium carbonate, bicarbonate, sesquicarbonate, tetraborate decahydrate, and silicate having a molar ratio of $SiO_2$ to alkali metal oxide of from about 0.5 to about 4.0, preferably from about 1.0 to about 2.4.

Water-soluble, nonphosphorus organic builders useful herein include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, benzene polycarboxylic acids, and citric acid.

Highly preferred polycarboxylate builders herein are set forth in U.S. Pat. No. 3,308,067, Diehl, issued Mar. 7, 1967 incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates of U.S. Pat. No. 3,723,322, Diehl incorporated herein by reference.

Other useful builders herein are sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000 for example), and the copolymers of maleic anhydride with vinyl methyl ether or ethylene.

Other suitable polycarboxylates for use herein are the polyacetal carboxylates described in U.S. Pat. No. 4,144,226, issued Mar. 13, 1979 to Crutchfield et al.; and U.S. Pat. No. 4,246,495, issued Mar. 27, 1979 to Crutchfield et al., both incorporated herein by reference.

"Insoluble" builders include both seeded builders such as 3:1 weight mixtures of sodium carbonate and calcium carbonate; and 2.7:1 weight mixtures of sodium sesquicarbonate and calcium carbonate. Amphorus and crystalline alumino silicates such as hydrated sodium Zeolite A are commonly used in laundry detergent applications. They have a particle size diameter of 0.1 micron to about 10 microns depending on water content of these molecules. These are referred to as ion exchange materials. Crystalline alumino silicates are characterized by their calcium ion exchange capacity. Amphorus alumino silicates are usually characterized by their magnesium exchange capacity. They can be naturally occurring or synthetically derived.

A detailed listing of suitable detergency builders can be found in U.S. Pat. No. 3,936,537, supra, incorporated herein by reference.

B. Miscellaneous Detergent Ingredients

Detergent composition components may also include hydrotropes, enzymes (e.g., proteases, amylases and cellulases), enzyme stabilizing agents, pH adjusting agents (monoethanolamine, sodium carbonate, etc.) halogen bleaches (e.g., sodium and potassium dichloroisocyanurates), peroxyacid bleaches (e.g., diperoxydodecane-1,12-dioic acid), inorganic percompound bleaches (e.g., sodium perborate), antioxidants as optional stabilizers, reductive agents, activators for percompound bleaches (e.g., tetraacetylethylenediamine and sodium nonanoyloxybenzene sulfonate), soil suspending agents (e.g., sodium carboxymethyl cellulose), soil anti-redisposition agents, corrosion inhibitors, perfumes and dyes, buffers, whitening agents, solvents (e.g., glycols and aliphatic alcohols) and optical brighteners. Any of other commonly used auxiliary additives such as inorganic salts and common salt, humectants, solubilizing agents, UV absorbers, softeners, chelating agents, static control agents and viscosity modifiers may be added to the detergent compositions of the invention.

For bar compositions, processing aids are optionally used such as salts and/or low molecular weight alcohols such as monodihydric, dihydric (glycol, etc.), trihydric (glycerol, etc.), and polyhydric (polyols) alcohols. Bar compositions may also include insoluble particulate material components, referred to as "fillers" such as calcium carbonate, silica and the like.

V. Composition Concentrations

The amount of the aminosilicone compound used in the laundry detergent compositions and methods of this invention will typically be sufficient to yield a concentration of aminosilicone compound in the washing medium of 0 to about 0.2 grams of aminosilicone compound per liter of washing medium, more typically from about 0.005 to about 0.1 g/L, and even more typically from about 0.01 to about 0.04 g/L.

In the compositions of the invention, the aminosilicone compound will typically be present in an amount of from about 0.005 to about 30% by weight, more typically from about 1 to about 10% by weight.

The compositions can be in any form that is convenient for use as a detergent e.g. bars, powders, flakes, pastes, or liquids which may be aqueous or non-aqueous and structured or unstructured. The detergent compositions can be prepared in any manner which is convenient and appropriate to the desired physical form so as co-agglomeration, spray drying, or dispersing in a liquid.

The total weight percentages of the conventional surfactants of the present invention, all weight percentages being based on the total active weight of the compositions of this invention consisting of aminosilicone compound, optional carrier, conventional surfactant(s), gemini surfactant(s), soil release agent(s), and (optionally) detergency builder(s) are about 10 to about 99.9 weight percent, typically about 15-75 weight percent.

The gemini surfactants are typically present, if employed, at a level of about 0.005 to about 50, typically from about 0.02-15.0, active weight percent of the composition.

The polymeric soil release agents, are typically present, if employed, at a level of from about 0.05 to about 40, typically from about 0.2-15 active weight percent.

The optional detergency builders are suitably present at a level of from about 0 to about 70 weight percent, typically from about 5 to about 50 weight percent.

VI. Industrial Applicability

The compositions and methods of this invention can be used to clean various fabrics, e.g. wool, cotton, silk, polyesters, nylon, other synthetics, blends of multiple synthetics and or synthetic/natural fiber blends. The compositions and method are particularly useful with colored fabrics, i.e. those that have a visually perceptible hue. The compositions and methods are also particularly useful in connection with washing media that also contain a fragrance. The fragrance need not be pre-mixed or pre-reacted with the aminosilicone oil in any way nor must the fragrance as an active principle a hydroxy functional compound.

The fragrance substances that may be used in the context of the invention include natural and synthetic fragrances, perfumes, scents, and essences and any other substances and mixtures of liquids and/or powdery compositions which emit a fragrance. As the natural fragrances, there are those of animal origin, such as musk, civet, castreum, ambergris, or the like, and those of vegetable origin, such as lemon oil, rose oil, citronella oil, sandalwood oil, peppermint oil, cinnamon oil, or the like. As synthetic fragrances, there are mixed fragrances of alpha-pinene, limonene, geraniol, linalool, lavandulol, nerolidol, or the like.

VII. Soluble Powder Detergent Compositions Without Inorganic Phosphates

For a good implementation of the invention, said compositions comprise:

from 5 to 60%, preferably from 8 to 40%, of their weight of at least one surface-active agent (S)

from 5 to 80%, preferably from 8 to 40%, of their weight of at least one soluble inorganic or organic builder (B)

from 0.01 to 8%, preferably from 0.1 to 5%, very particularly from 0.3 to 3%, of their weight of at least one aminosilicone (AS).

Mention may be made, among surface-active agents, of the anionic or non-ionic surface-active agents commonly used in the field of detergents for washing laundry.

Anionic Surface-Active Agents

Typical anionic surface-active agents include the following:

alkyl ester sulphonates of formula R—CH($SO_3$M)-COOR', where R represents a $C_{8-20}$, preferably $C_{10}$-$C_{16}$, alkyl radical, R' a $C_1$-$C_6$, preferably $C_1$-$C_3$, alkyl radical and M an alkali metal (sodium, potassium or lithium) cation, a substituted or unsubstituted ammonium (methyl-, dimethyl-, trimethyl- or tetramethylammonium, dimethylpiperidinium, and the like) cation or a cation derived from an alkanolamine (monoethanolamine, diethanolamine, triethanolamine, and the like);

alkyl sulphates of formula ROS$O_3$M, where R represents a $C_5$-$C_{24}$, preferably $C_{10}$-$C_{18}$, alkyl or hydroxyalkyl radical, M representing a hydrogen atom or a cation with the same definition as above, and their ethoxylated (EO) and/or propoxylated (PO) derivatives exhibiting an average of 0.5 to 30, preferably of 0.5 to 10, EO and/or PO units;

alkylamide sulphates of formula RCONHR'OS$O_3$M, where R represents a $C_2$-$C_{22}$, preferably $C_6$-$C_{20}$, alkyl radical, R' a $C_2$-$C_3$ alkyl radical, M representing a hydrogen atom or a cation with the same definition as above, and their ethoxylated (EO) and/or propoxylated (PO) derivatives exhibiting an average of 0.5 to 60 EO and/or PO units;

salts of $C_8$-$C_{24}$, preferably $C_{14}$-$C_{20}$, saturated or unsaturated fatty acids, $C_9$-$C_{20}$ alkylbenzenesulphonates, primary or secondary $C_8$-$C_2$ alkylsulphonates, alkylglycerol sulphonates, the sulphonated polycarboxylic acids described in GB-A-1,082,179, paraffin sulphonates, N-acyl-N-alkyltaurates, alkyl phosphates, isethionates, alkylsuccinamates, alkylsulphosuccinates, the monoesters or diesters of sulphosuccinates, N-acylsarcosinates, alkylglycoside sulphates or polyethoxycarboxylates the cation being an alkali metal (sodium, potassium or lithium), a substituted or unsubstituted ammonium residue (methyl-, dimethyl-, trimethyl- or tetramethylammonium, dimethylpiperidinium, and the like), or a residue derived from an alkanolamine (monoethanolamine, diethanolamine, triethanolamine, and the like);

sophorolipids, such as those in acid or lactone form, derivatives of 17-hydroxyoctadecenic acid; and the like.

Non-Ionic Surface Active Agents

Typical non-ionic surface-active agents include the following:

polyoxyalkylenated (polyoxyethylenated, polyoxypropylenated or polyoxybutylenated) alkylphenols, the alkyl substituent of which is $C_6$-$C_{12}$, containing from 5 to 25 oxyalkylene units; mention may be made, by way of example, of Triton X-45, X-114, X-100 or X-102, sold by Rohm & Haas Co., or Igepal NP2 to NP17 from Rhône-Poulenc;

polyoxyalkylenated $C_8$-$C_{22}$ aliphatic alcohols containing from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Co., Kyro EOB, sold by The Procter & Gamble Co., Synperonic A3 to A9 from ICI, or Rhodasurf IT, DB and B from Rhône-Poulenc;

the products resulting from the condensation of ethylene oxide or of propylene oxide with propylene glycol or ethylene glycol, with a weight-average molecular mass of the order of 2000 to 10,000, such as the Pluronics sold by BASF;

the products resulting from the condensation of ethylene oxide or of propylene oxide with ethylenediamine, such as the Tetronics sold by BASF;

ethoxylated and/or propoxylated $C_8$-$C_{18}$ fatty acids containing from 5 to 25 oxyethylene and/or oxypropylene units;

$C_8$-$C_{20}$ fatty acid amides containing from 5 to 30 oxyethylene units;

ethoxylated amines containing from 5 to 30 oxyethylene units;

alkoxylated amidoamines containing from 1 to 50, preferably from 1 to 25, very particularly from 2 to 20, oxyalkylene units (preferably oxyethylene units);

amine oxides, such as ($C_{10}$-$C_{18}$ alkyl)dimethylamine oxides or ($C_8$-$C_{22}$ alkoxy)ethyldihydroxyethylamine oxides;

alkoxylated terpene hydrocarbons, such as ethoxylated and/or propoxylated a- or b-pinenes, containing from 1 to 30 oxyethylene and/or oxypropylene units;

the alkylpolyglycosides which can be obtained by condensation (for example by acid catalysis) of glucose with primary fatty alcohols (U.S. Pat. No. 3,598,865, U.S.

Pat. No. 4,565,647, EP-A-132,043, EP-A-132,046, and the like) exhibiting a $C_4$-$C_{20}$, preferably $C_8$-$C_{18}$, alkyl group and a mean number of glucose units of the order of 0.5 to 3, preferably of the order of 1.1 to 1.8, per mole of alkylpolyglycoside (APG); mention may in particular be made of those exhibiting:

a $C_8$-$C_{14}$ alkyl group and, on average, 1.4 glucose units per mole a $C_{12}$-$C_{14}$ alkyl group and, on average, 1.4 glucose units per mole a $C_8$-$C_{14}$ alkyl group and, on average, 1.5 glucose units per mole $C_8$-$C_{10}$ alkyl group and, on average, 1.6 glucose units per mole sold respectively under the names Glucopon 600 EC®, Glucopon 600 CSUP®, Glucopon 650 EC® and Glucopon 225 CSUP® by Henkel.

Mention may particularly be made, among soluble inorganic builders (13), of:

amorphous or crystalline alkali metal silicates of formula $xSiO_2 \cdot M_2O \cdot yH_2O$, with $1 \leq x \leq 3.5$ and $0 \leq y/(x+1+y) \leq 0.5$, where M is an alkali metal and very particularly sodium, including lamellar alkali metal silicates, such as those described in U.S. Pat. No. 4,664,839;

alkaline carbonates (bicarbonates, sesquicarbonates);

cogranules of hydrated alkali metal silicates and of alkali metal carbonates (sodium or potassium) which are rich in silicon atoms in the Q2 or Q3 form, described in EP-A488,868; and tetraborates or borate precursors.

Mention may particularly be made, among soluble organic builders (B), of water-soluble polyphosphonates (ethane-1-hydroxy-1,1-diphosphonates, salts of methylenediphosphonates, and the like);

water-soluble salts of carboxyl polymers or copolymers, such as the water-soluble salts of polycarboxylic acids with a molecular mass of the order of 2000 to 100,000 obtained by polymerization or copolymerization of ethylenically unsaturated carboxylic acids, such as acrylic acid, maleic acid or anhydride, fumaric acid, itaconic acid, mesaconic acid, citraconic acid or methylenemalonic acid, and very particularly polyacrylates with a molecular mass of the order of 2000 to 10,000 (U.S. Pat. No. 3,308,067) or copolymers of acrylic acid and of maleic anhydride with a molecular mass of the order of 5000 to 75,000 (EP-A-066,915);

polycarboxylate ethers (oxydisuccinic acid and its salts, tartrate monosuccinic acid and its salts, tartrate disuccinic acid and its salts);

hydroxypolycarboxylate ethers;

citric acid and its salts, mellitic acid, succinic acid and their salts;

salts of polyacetic acids (ethylenediaminetetraacetates, nitrilotriacetates, N-(2-hydroxyethyl)nitrilodiacetates);

($C_5$-$C_{20}$ alkyl)succinic acids and their salts (2-dodecenylsuccinates, laurylsuccinates, and the like);

polyacetal carboxylic esters;

polyaspartic acid, polyglutamic acid and their salts;

polyimides derived from the polycondensation of aspartic acid and/or of glutamic acid;

polycarboxymethylated derivatives of glutamic acid (such as N,N-bis(carboxymethyl)glutamic acid and its salts, in particular the sodium salt) or of other amino acids; and aminophosphonates, such as nitrilotris(methylenephosphonate)s.

For a good implementation of the invention, the said aminosilicone (AS) can be chosen from the aminopolyorganosiloxanes (APS) comprising siloxane units of general formulae:

  (I), where a+b=3, with a 0, 1, 2 or 3 and b=0, 1, 2 or 3

  (II), where c+d=2, with c=0 or 1 and d=1 or 2

  (III) and optionally

  (IV), where e+f=0 or 1, with e=0 or 1 and f=0 or 1 in which formulae, the $R^1$ symbols, which are identical or different, represent a saturated or unsaturated, linear or branched, aliphatic radical containing from 1 to 10 carbon atoms or a phenyl radical, optionally substituted by fluoro or cyano groups;

the A symbols, which are identical or different, represent a primary, secondary, tertiary or quaternized amino group bonded to the silicon via an SiC bond;

the B symbols, which are identical or different, represent an OH functional group;

an OR functional group, where R represents an alkyl group containing from 1 to 12 carbon atoms, preferably from 3 to 6 carbon atoms, very particularly 4 carbon atoms;

an OCOR' functional group, where $R^1$ represents an alkyl group containing from 1 to 12 carbon atoms, preferably 1 carbon atom; or the A symbol.

The aminopolyorganosiloxanes (APS) preferably comprise units of formula (I), (II), (III) and optionally (IV), where in the units of formula (I), a=1, 2 or 3 and b=0 or 1 and in the units of formula (II), c=1 and d=1.

The A symbol is preferably an amino group of formula

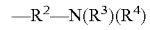

where the $R^2$ symbol represents an alkylene group containing from 2 to 6 carbon atoms, which group is optionally substituted or interrupted by one or more nitrogen or oxygen atoms, the $R^3$ and $R^4$ symbols, which are identical or different, represent

H, an alkyl or hydroxyalkyl group containing from 1 to 12 carbon atoms, preferably from 1 to 6 carbon atoms, an aminoalkyl group, preferably a primary aminoalkyl group, the alkyl group of which contains from 1 to 12 carbon atoms, preferably from 1 to 6 carbon atoms, which group is optionally substituted and/or interrupted by at least one nitrogen and/or oxygen atom, the said amino group optionally being quaternized, for example by a hydrohalic acid or an alkyl or aryl halide.

Mention may particularly be made, as example of A symbol, of those of formulae:

| | |
|---|---|
|  | 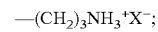 |
| 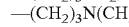 |  |
|  | 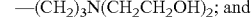 |
|  |  |

Among these, the preferred formulae are:

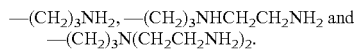

—(CH$_2$)$_3$N(CH$_2$CH$_2$NH$_2$)$_2$.

The R$^1$ symbol preferably represent methyl, ethyl, vinyl, phenyl, trifluoropropyl or cyanopropyl groups. It very particularly represents the methyl group (at least predominantly).

The B symbol preferably represents an OR group where R contains from 1 to 6 carbon atoms, very particularly 4 carbon atoms, or the A symbol. The B symbol is very preferably a methyl or butoxy group.

The aminosilicone is preferably at least substantially linear. It is very preferably linear, that is to say does not contain units of formula (IV). It can exhibit a number-average molecular mass of the order of 2000 to 50,000, preferably of the order of 3000 to 30,000.

For a good implementation of the invention, the aminosilicones (AS) or the aminopolyorganosiloxanes (APS) can exhibit in their chain, per total of 100 silicon atoms, from 0.1 to 50, preferably from 0.3 to 10, very particularly from 0.5 to 5, aminofunctionalized silicon atoms.

Insoluble inorganic builders can additionally be present but in a limited amount in order not to exceed the level of less than 20% of insoluble inorganic material defined above.

Mention may be made, among these adjuvants, of crystalline or amorphous aluminosilicates of alkali metals (sodium or potassium) or of ammonium, such as zeolites A, P, X, and the like.

The detergent compositions can additionally comprise standard additives for powder detergent compositions. Typical such additional ingredients are as follows.

Additional Soil Release Agents

Additional soil release agents may be provided in amounts of the order of 0.01-10%, preferably of the order of 0.1 to 5% and very particularly of the order of 0.2-3% by weight. Typical such agents include any of the following:

cellulose derivatives, such as cellulose hydroxyethers, methylcellulose, ethylcellulose, hydroxypropyl methylcellulose or hydroxybutyl methylcellulose;

poly(vinyl ester)s grafted onto polyalkylene stems, such as poly(vinyl acetate)s grafted onto polyoxyethylene stems (EP-A-219,048);

poly(vinyl alcohol)s;

polyester copolymers based on ethylene terephthalate and/or propylene terephthalate and polyoxyethylene terephthalate units, with an ethylene terephthalate and/or propylene terephthalate (number of units)/polyoxyethylene terephthalate (number of units) molar ratio of the order of 1/10 to 10/1, preferably of the order of 1/1 to 9/1, the polyoxyethylene terepthalates exhibiting polyoxyethylene units having a molecular weight of the order of 300 to 5000, preferably of the order of 600 to 5000 (U.S. Pat. No. 3,959,230, U.S. Pat. No. 3,893,929, U.S. Pat. No. 4,116,896, U.S. Pat. No. 4,702,857 and U.S. Pat. No. 4,770,666);

sulphonated polyester oligomers, obtained by sulphonation of an oligomer derived from ethoxylated allyl alcohol, from dimethyl terephthalate and from 1,2-propanediol, exhibiting from 1 to 4 sulphonate groups (U.S. Pat. No. 4,968,451);

polyester copolymers based on propylene terephthalate and polyoxyethylene terephthalate units which are optionally sulphonated or carboxylated and terminated by ethyl or methyl units (U.S. Pat. No. 4,711,730) or optionally sulphonated polyester oligomers terminated by alkylpolyethoxy groups (U.S. Pat. No. 4,702,857) or anionic sulphopolyethoxy (U.S. Pat. No. 4,721,580) or sulphoaroyl (U.S. Pat. No. 4,877,896) groups;

sulphonated polyesters with a molecular mass of less than 20,000, obtained from a diester of terephthalic acid, isophthalic acid, a diester of sulphoisophthalic acid and a diol, in particular ethylene glycol (WO 95/32997);

polyesterpolyurethanes obtained by reaction of a polyester with a number-average molecular mass of 300 to 4000, obtained from adipic acid and/or terephthalic acid and/or sulphoisophthalic acid and a diol, with a prepolymer containing end isocyanate groups obtained from a poly(ethylene glycol) with a molecular mass of 600-4000 and a diisocyanate (FR-A-2,334,698);

Anti-Redeposition Agents

Anti-redeposition agents may be provided in amounts of approximately 0.01-10% by weight for a powder detergent composition and of approximately 0.01-5% by weight for a liquid detergent composition. Typical such agents include any of the following:

ethoxylated monoamines or polyamines or ethoxylated amine polymers (U.S. Pat. No. 4,597,898, EP-A-011,984);

carboxymethylcellulose;

sulphonated polyester oligomers obtained by condensation of isophthalic acid, dimethyl sulphosuccinate and diethylene glycol (FR-A-2,236,926); and polyvinylpyrrolidones.

Bleaching Agents

Bleaching agents may be provided in an amount of approximately 0.1-20%, preferably 1-10%, of the weight of the said powder detergent composition. Typical such agents include any of the following:

perborates, such as sodium perborate monohydrate or tetrahydrate;

peroxygenated compounds, such as sodium carbonate peroxohydrate, pyrophosphate peroxohydrate, urea hydrogen peroxide, sodium peroxide or sodium persulphate;

percarboxylic acids and their salts (known as "percarbonates"), such as magnesium monoperoxyphthalate hexahydrate, magnesium meta-chloroperbenzoate, 4-nonylamino-4-oxoperoxybutyric acid, 6-nonylamino-6-oxoperoxycaproic acid, diperoxydodecanedioic acid, peroxysuccinic acid nonylamide or decyldiperoxysuccinic acid, preferably in combination with a bleaching activator generating, in situ in the washing liquor, a peroxycarboxylic acid; mention may be made, among these activators, of tetraacetylethylenediamine, tetraacetylmethylenediamine, tetraacetylglycoluril, sodium p-acetoxybenzenesulphonate, pentacetylglucose, octaacetyllactose, and the like.

Fluorescence Agents

Fluorescence agents may be provided in an amount of approximately 0.05-1.2% by weight. Typical such agents include any derivatives of stilbene, pyrazoline, coumarin, fumaric acid, cinnamic acid, azoles, methinecyanines, thiophenes, and the like;

Foam-Suppressant Agents

Foam-suppressant agents may be provided in amounts which can range up to 5% by weight. Typical such agents include any of the following:

C$_{10}$-C$_{24}$ fatty monocarboxylic acids or their alkali metal, ammonium or alkanolamine salts or fatty acid triglycerides;

saturated or unsaturated, aliphatic, alicyclic, aromatic or heterocyclic hydrocarbons, such as paraffins or waxes;

N-alkylaminotriazines;
monostearyl phosphates or monostearyl alcohol phosphates; and
polyorganosiloxane oils or resins, optionally combined with silica particles;

Softeners

Softeners may be provided in amounts of approximately 0.5-10% by weight. Typical such agents are clays (smectites, such as montmorillonite, hectorite or saponite);

Enzymes

Enzymes may be provided in an amount which can range up to 5 mg by weight, preferably of the order of 0.05-3 mg, of active enzyme/g of detergent composition. Typical enzymes are proteases, amylases, lipases, cellulases or peroxydases (U.S. Pat. No. 3,553,139, U.S. Pat. No. 4,101,457, U.S. Pat. No. 4,507,219 and U.S. Pat. No. 4,261,868).

Other Additives

Typical other additives may be any of the following:
alcohols (methanol, ethanol, propanol, isopropanol, propanediol, ethylene glycol or glycerol);
buffer agents or fillers, such as sodium sulphate or alkaline earth metal carbonates or bicarbonates; and
pigments,
the amounts of optional insoluble inorganic additives having to be sufficiently limited in order not to exceed the level of less than 20% of insoluble inorganic materials defined above.

Agrochemical Foams

The foam enhancers of the present invention may also be employed in foams for delivering agrochemicals, for example, herbicides, pesticides, fungicides, or detoxifying agents. Examples of foams for agrochemicals are disclosed by U.S. Pat. Nos. 3,960,763 to Lambon, et al; 5,346,699 to Tiernan, et al; 5,549,869 to Iwakawa; 5,686,024 to Dahanayake et al; and 5,735,955 to Monaghan et al, all of which are incorporated herein by reference in their entirety.

Oil Field Foams

The foam enhancers of the present invention may be employed in foams for use in subterranean formation, such as oil wells. For example, foams are employed in drilling fluids, as well as in enhanced oil recovery with steam or carbon dioxide. Examples of foams for use in oil wells are disclosed by U.S. Pat. Nos. 5,821,203 to Williamson; 5,706,895 to Sydansk; 5,714,001 to Savoly, et al; 5,042,583 to D'Souza, et al; 5,614,473 to Dino, et al; and 5,027,898 to Naae, all of which are incorporated herein by reference in their entirety.

Fire-Fighting Foams

The foam enhancer of the present invention may be employed in foams for use in fire-fighting. Typical fire-fighting foams are disclosed in U.S. Pat. Nos. 5,882,541 to Achtmann; 5,658,961 to Cox, Sr.; and 5,496,475 to Jho, et al; 5,218,021 to Clark et al; and 4,713,182 to Hiltz, et al, all of which are incorporated herein by reference in their entirety.

Coagulants for Treating Paper Making Water

The foam enhancers of the present invention also have another use unrelated to foaming. They are retention aids for retention of titanium dioxide ($TiO_2$) used for whitening paper during paper making. These retention aids act as coagulants to cause particles of titanium dioxide to coagulate. The coagulated particles deposit on the paper. As a result, water will drain faster from paper upon which coagulated titanium dioxide is deposited. The use of titanium dioxide for whitening paper is disclosed by U.S. Pat. Nos. 5,665,466 to Guez et al; and 5,705,033 to Gerard, et al, both of which are incorporated herein by reference in their entirety.

Hard Surface Cleaners

The foam enhancer of the present invention may be employed with foam hard surface cleaners typically employed with bathroom surfaces. Examples of such foam cleaners are disclosed by U.S. Pat. Nos. 5,612,308 to Woo, et al and 5,232,632 to Woo, et al, incorporated herein by reference.

Shower Rinse

The polymers of the present invention are also useful in shower reinses to make them better maintain a clean shower and prevent buildup of undesired deposits. Typical shower rinses are disclosed by U.S. Pat. Nos. 5,536,452 to Black and 5,587,022 to Black, incorporated herein by reference in their entirety.

High Purity Compositions

A particular process may be advantageous to make copolymers from at least one tertiary amino-containing monomer, e.g., dimethylaminoethyl(meth)acrylate, and at least one vinyl-containing monomer, when the at least one vinyl-functional monomer is not substituted by an alkyl group on the 2-position of the vinyl moiety (for example, not methacrylic acid, hydroxyethylmethacrylate or hydroxypropylmethacrylate). This is advantageous to make such copolymers free of or having minimal Michael addition adducts of the ingredients. Also, Michael addition adducts form but revert back to monomers if the hydrogen atom is substituted by an alkyl group on the 2-position of the vinyl moiety.

In the process, at least one tertiary amino-containing monomer, at least one vinyl-containing monomer not substituted by an alkyl group on the 2-position of the vinyl moiety, an acid, and a polymerization initiator are mixed in a polymerization reactor to form a polymerization mixture in the reactor. The at least one tertiary amino-containing monomer and the at least one vinyl-containing monomer are copolymerized in the polymerization mixture, to form a copolymer, and optionally a Michael addition adduct of the at least one tertiary amino-containing monomer and the at least one vinyl-containing monomer. However, Michael adduct formation is prevented/minimized by performing at least one of the following steps in a process for making copolymers from tertiary amino monomers and vinyl-functional monomers.

1. Avoid formation of adduct by separating the tertiary amino monomer (e.g. dimethylaminoethyl(meth)acrylate) from the vinyl-functional monomer prior to polymerization.

2. Avoid formation of adduct by maintaining the at least one tertiary amino-containing monomer and the at least one vinyl-functional monomer water-free prior to the copolymerizing.

3. Conduct polymerization at a high temperature (typically about 70 to about 90° C., preferably about 80 to about 90° C.) and at a suitable pH (typically about 3 to about 10, preferably about 4 to about 8, most preferably about 4 to about 6) to cause the adduct formed to be unstable and revert to monomers. Thus, monomers bound by the adduct will be liberated to copolymerize.

Typically, the at least one vinyl-functional monomer has is selected from at least one member of the group consisting of a monomer of Formula A:

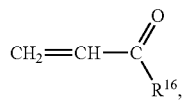

wherein $R^{16}$ is a group which permits the vinyl-functional monomer to undergo Michael addition.

Preferably, the acid reactants, e.g., mineral acid (for example sulfuric acid) or citric acid, is fed to the reactor before the monomers. Typically these processes are performed as semi-batch processes. However, batch or continuous processes are not precluded.

In a particular embodiment, a tertiary amino-containing monomer, water, and an acid may be mixed in a reactor to form a neutralized tertiary amino-containing monomer mixture having a pH of about 3 to about 10. The neutralized tertiary amino-containing monomer mixture, a vinyl-functional monomer, water, and an initiator are fed to the reactor. The initiator may be a single ingredient (typically sodium persulfate) or a redox system combining an oxidizing component (typically sodium persulfate) and a reducing component (typically sodium metabisulfite). Water is typically fed directly to the reactor with the vinyl-functional monomer and neutralized tertiary amino-containing monomer, and/or with other ingredients.

Generally, the neutralized tertiary amino-containing monomer mixture, a vinyl-functional monomer/water mixture, and initiator are separately fed to the reactor. Preferably, the neutralized tertiary amino-containing monomer mixture, the vinyl-functional monomer/water mixture, at least a portion of the initiator are separately, yet simultaneously, fed to the reactor to form the polymerization mixture. The initiator can be a single organic or inorganic compound or a redox (reduction/oxidation) system of two or more compounds. For example, U.S. Pat. No. 5,863,526, incorporated herein by reference in its entirety, discloses typical initiator systems. The polymerization mixture is maintained in the reactor at polymerization conditions including a pH of about 3 to about 10, preferably about 4 to about 8, most preferably about 4 to about 6, and a temperature of about 70 to about 90° C., preferably about 80 to about 90° C., for a time of about 1 to about 3 hours, to form a copolymer and the copolymer product is recovered.

In a second embodiment, water and acid are fed first to the reactor. Then, water-free tertiary amino-containing monomer, water-free vinyl-functional monomer and initiator are separately fed to the reactor to admix with the acid and water in the reactor. In the reactor, the monomers polymerize in the presence of the initiator described above.

Generally, the water is provided with acid and initiator. The polymerization mixture is maintained at the above-described polymerization conditions to form the copolymer product. Then the copolymer product is recovered. If desired, the tertiary amino-containing monomer, the vinyl-functional monomer, and the initiator are separately, yet simultaneously fed to the reactor.

In a third embodiment the process may be the same as the second embodiment except that the water-free monomers are mixed to form a water-free mixture prior to being fed to the reactor.

The present invention is further illustrated by the following examples of block polymeric enhancing agents, provided that no observations or other statements made therein should be construed to limit the invention, unless otherwise expressly indicated in the claims appended hereto. All amounts, parts, percentages, and ratios expressed in this specification, including the claims are by weight unless otherwise apparent in context.

SYNTHESIS EXAMPLES

Example 1

Process for Making Poly(DMAM-b-HEA)—Lithium diisopropylamide (5.6 mL, 11.12 mmol, 2.0 M), lithium chloride (2.35 g, 55.58 mmol) and THF (500 mL) are cooled to −78° C. 2-(Dimethylamino)ethyl methacrylate (25.16 g, 0.16 mol) is added to the solution and allowed to polymerize for 2 h. At this time, 2-hydroxyethyl methacrylate (62.47 g, 0.48 mol) is added to the reaction mixture. The reaction is stirred for an additional 2 h. The polymerization is quenched with methanol. Poly(DMAM-b-HEA) is isolated by removing the solvent by rotary evaporation.

Example 2

Process for Making Poly(DMAM-b-HEA)—The procedure of Example 1 is repeated with the substitution of (diphenylmethyl)lithium for lithium diisopropylamide.

Example 3

Process for Making Poly(DMAM-b-HEA-b-AA)-2-Hydroxyethylacrylate (125.00 g, 1.08 mol) is placed in a flask along to make a solution with anisole (250 mL). CuBr (41.6 mg, 29.0 mmol) complexed by 2,2'-bipyridyl (45.3 mg, 29.0 mmol) (catalyst) and methyl 2-bromopropionate (48.4 mg, 29.0 mmol) (initiator) are placed in the flask. The mixture is heated to 90° C. for 18 h. The product mixture is dissolved in THF and precipitated with methanol. The product is collected and added to a reactor to make a 50% solution with 1,2-dichlorobenzene. 2-(Dimethylamino)ethyl methacrylate (39.31 g, 0.25 mol) is added to the solution. CuCl (0.58 g, 58.0 mmol) complexed by hexamethyltriethylenetetramine (1.34 g, 58.0 mmol) is added to the reactor. The mixture is heated to 90° C. for 18 h. A polymer is isolated by dissolving the reaction mixture in THF and then precipitated with hexanes. The product is collected and added to a reactor to make a 50% solution with 1,2-dichlorobenzene. Acrylic acid (5.93 g, 82.3 mmol) is added to the solution. CuCl (0.58 g, 58.0 mmol) complexed by hexamethyltriethylenetetramine (1.34 g, 58.0 mmol) is added to the reactor. The mixture is heated to 90° C. for 18 h. The product polymer is isolated by dissolving the reaction mixture in THF and then precipitated with hexanes. The product is collected and dried.

Example 4

Process for Making Poly(DMAM-b-HEA-b-Sty)—The procedure of Example 3 is repeated with the substitution of styrene for acrylic acid.

Example 5

Process for Making Poly(DMAM-b-HEA-b-Sty-b-AA)-2-Hydroxyethylacrylate (125.00 g, 1.08 mol) is placed in a flask along to make a solution with anisole (250 mL). CuBr (41.6 mg, 29.0 mmol) complexed by 2,2'-bipyridyl (45.3 mg, 29.0 mmol) (catalyst) and methyl 2-bromopropionate (48.4 mg, 29.0 mmol) (initiator) are placed in the flask. The mixture is heated to 90° C. for 18 h. The product mixture is dissolved in THF and precipitated with methanol. The product is collected and added to a reactor to make a 50% solution with 1,2-dichlorobenzene. 2-(Dimethylamino)ethyl methacrylate (39.31 g, 0.25 mol) is added to the solution. CuCl (0.58 g, 58.0 mmol) complexed by hexamethyltriethylenetetramine (1.34 g, 58.0 mmol) is added to the reactor. The mixture is heated to 90° C. for 18 h. A polymer is isolated by dissolving the reaction mixture in THF and then precipitated with hexanes. The product is collected and added to a reactor to make a 50% solution with 1,2-dichlorobenzene. Styrene (4.28 g, 41.1 mmol) is added to the solution. CuCl (0.58 g, 58.0 mmol) complexed by hexamethyltriethylenetetramine (1.34 g, 58.0 mmol) is added to the reactor. The mixture is heated to 90° C. for 18 h. A polymer is isolated by dissolving the reaction mixture in THF and then precipitated with hexanes. The product is collected and added to a reactor to make a 50% solution with 1,2-dichlorobenzene. Acrylic acid (2.96 g, 41.1 mmol) is added to the solution. CuCl (0.58 g, 58.0 mmol) complexed by hexamethyltriethylene-tetramine (1.34 g, 58.0 mmol) is added to the reactor. The mixture is heated to 90° C. for 18 h. The product polymer is isolated by dissolving the reaction mixture in THF and then precipitated with hexanes. The product is collected and dried.

Example 6

Process for Making Poly(DMAM-b-MA)—Lithium diisopropylamide (5.6 mL, 11.12 mmol, 2.0 M), lithium chloride (2.35 g, 55.58 mmol) and THF (500 mL) are cooled to −78° C. 2-(Dimethylamino)ethyl methacrylate (75.47 g, 0.48 mol) is added to the solution and allowed to polymerize for 2 h. At this time, methyl acrylate (13.77 g, 0.16 mol) is added to the reaction mixture. The reaction is stirred for an additional 2 h. The polymerization is quenched with methanol. Poly(DMAM-b-MA) is isolated by removing the solvent by rotary evaporation.

The following are non-limiting examples of liquid detergent compositions comprising the block polymeric suds extenders according to the present invention.

TABLE I

| Ingredients | weight % | | |
|---|---|---|---|
| | 7 | 8 | 9 |
| $C_{12}$-$C_{15}$ Alkyl sulphate | — | 28.0 | 25.0 |
| $C_{12}$-$C_{13}$ Alkyl ($E_{0.6-3}$) sulfate | 30 | — | — |
| $C_{12}$ Amine oxide | 5.0 | 3.0 | 7.0 |
| $C_{12}$-$C_{14}$ Betaine | 3.0 | — | 1.0 |
| $C_{12}$-$C_{14}$ Polyhydroxy fatty acid amide | — | 1.5 | — |
| $C_{10}$ Alcohol Ethoxylate $E_9$ [1] | 2.0 | — | 4.0 |
| Diamine [2] | 1.0 | — | 7.0 |
| $Mg^{2+}$ (as $MgCl_2$) | 0.25 | — | — |
| Citrate (cit2K3) | 0.25 | — | — |
| Block polymeric suds booster [3] | 1.25 | 2.6 | 0.9 |
| Minors and water [4] | balance | balance | balance |
| pH of a 10% aqueous solution | 9 | 10 | 10 |

[1] $E_9$ Ethoxylated Alcohols as sold by the Shell Oil Co.
[2] 1,3-diaminopentane sold as Dytek EP.
[3] Suds Booster according to the present invention, preferably a suds booster in accordance with Examples 1-6, more preferably poly(DMAM-b-HEA) (1:3) block polymer of Example 1.
[4] Includes perfumes, dyes, ethanol, etc.

TABLE II

| Ingredients | weight % | | |
|---|---|---|---|
| | 10 | 11 | 12 |
| $C_{12}$-$C_{13}$ Alkyl ($E_{0.6-3}$) sulfate | — | 15.0 | 10.0 |
| Paraffin sulfonate | 20.0 | — | — |
| Na $C_{12}$-$C_{13}$ linear alkylbenzene sulfonate | 5.0 | 15.0 | 12.0 |
| $C_{12}$-$C_{14}$ Betaine | 3.0 | 1.0 | — |
| $C_{12}$-$C_{14}$ Polyhydroxy fatty acid amide | 3.0 | — | 1.0 |
| $C_{10}$ Alcohol Ethoxylate $E_9$ [1] | — | — | 20.0 |
| Diamine [2] | 1.0 | — | 7.0 |
| DTPA [3] | — | 0.2 | — |
| $Mg^{2+}$ (as $MgCl_2$) | 1.0 | — | — |
| $Ca^{2+}$ (as $Ca(citrate)_2$) | — | 0.5 | — |
| Protease [4] | 0.01 | — | 0.001 |
| Amylase [5] | — | 0.001 | 0.001 |
| Hydrotrope [6] | 2.0 | 1.5 | 3.0 |
| Block polymeric suds booster [7] | 0.5 | 3.0 | 0.5 |
| Minors and water [8] | balance | balance | balance |
| pH of a 10% aqueous solution | 9.3 | 8.5 | 11 |

[1] $E_9$ Ethoxylated Alcohols as sold by the Shell Oil Co.
[2] 1,3-bis(methylamino)cyclohexane.
[3] Diethylenetriaminepentaacetate.
[4] Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[5] Suitable amylase enzymes include Termamyl ®, Fungamyl ®; Duramyl ®; BAN ® and the amylases as described in WO95/26397 and in co-pending application by Novo Nordisk PCT/DK/96/00056.
[6] Suitable hydrotropes include sodium, potassium, ammonium or water-soluble substituted ammonium salts of toluene sulfonic acid, naphthalene sulfonic acid, cumene sulfonic acid, xylene sulfonic acid.
[7] Suds Booster according to the present invention, preferably a suds booster in accordance with Examples 1-6, more preferably poly(DMAM-b-HEA) (1:3) block polymer of Example 2.
[8] Includes perfumes, dyes, ethanol, etc.

TABLE III

| Ingredients | weight % | | | |
|---|---|---|---|---|
| | 13 | 14 | 15 | 16 |
| $C_{12}$-$C_{15}$ Alkyl ($E_1$) sulfate | — | 30.0 | — | — |
| $C_{12}$-$C_{15}$ Alkyl ($E_{1.4}$) sulfate | 30.0 | — | 27.0 | — |
| $C_{12}$-$C_{15}$ Alkyl ($E_{2.2}$) sulfate | — | — | — | 15 |
| $C_{12}$ Amine oxide | 5.0 | 5.0 | 5.0 | 3.0 |
| $C_{12}$-$C_{14}$ Betaine | 3.0 | 3.0 | — | — |
| $C_{10}$ Alcohol Ethoxylate $E_9$ [1] | 2.0 | 2.0 | 2.0 | 2.0 |
| Diamine [2] | 1.0 | 2.0 | 4.0 | 2.0 |
| $Mg^{2+}$ (as $MgCl_2$) | 0.25 | 0.25 | — | — |
| $Ca^{2+}$ (as $Ca(citrate)_2$) | — | 0.4 | — | — |
| Block polymeric suds booster [3] | 0.5 | 1.0 | 0.75 | 5.0 |
| Minors and water [4] | balance | balance | balance | balance |
| pH of a 10% aqueous solution | 7.4 | 7.6 | 7.4 | 7.8 |

[1] $E_9$ Ethoxylated Alcohols as sold by the Shell Oil Co.
[2] 1,3-diaminopentane sold as Dytek EP.
[3] Suds Booster according to the present invention, preferably a suds booster in accordance with Examples 1-6, more preferably poly(DMAM-b-HEA-b-AA)(1:3:0.33) block polymer of Example 3.
[4] Includes perfumes, dyes, ethanol, etc.

TABLE IV

| Ingredients | weight % | | |
|---|---|---|---|
| | 17 | 18 | 19 |
| $C_{12}$-$C_{13}$ Alkyl ($E_{0.6-3}$) sulfate | — | 15.0 | 10.0 |
| Paraffin sulfonate | 20.0 | — | — |
| Na $C_{12}$-$C_{13}$ linear alkylbenzene sulfonate | 5.0 | 15.0 | 12.0 |
| $C_{12}$-$C_{14}$ Betaine | 3.0 | 1.0 | — |
| $C_{12}$-$C_{14}$ Polyhydroxy fatty acid amide | 3.0 | — | 1.0 |
| $C_{10}$ Alcohol Ethoxylate $E_9$ [1] | — | — | 20.0 |
| Diamine [2] | 1.0 | — | 7.0 |
| $Mg^{2+}$ (as $MgCl_2$) | 1.0 | — | — |
| $Ca^{2+}$ (as $Ca(citrate)_2$) | — | 0.5 | — |
| Protease [3] | 0.1 | — | — |
| Amylase [4] | — | 0.02 | — |

TABLE IV-continued

| Ingredients | weight % | | |
|---|---|---|---|
| | 17 | 18 | 19 |
| Lipase [5] | — | — | 0.025 |
| DTPA [6] | — | 0.3 | — |
| Citrate (cit2K3) | 0.65 | — | — |
| Block polymeric suds booster [7] | 1.5 | 2.2 | 3.0 |
| Minors and water [8] | balance | balance | balance |
| pH of a 10% aqueous solution | 9.3 | 8.5 | 11 |

[1] $E_9$ Ethoxylated Alcohols as sold by the Shell Oil Co.
[2] 1,3-bis(methylamino)cyclohexane.
[3] Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[4] Suitable amylase enzymes include Termamyl ®, Fungamyl ®; Duramyl ®; BAN ®' and the amylases as described in WO95/26397 and in co-pending application by Novo Nordisk PCT/DK/96/00056.
[5] Suitable lipase enzymes include Amano-P; M1 Lipase ®; Lipomax ®; Lipolase ®' D96L - lipolytic enzyme variant of the native lipase derived from Humicola lanuginosa as described in U.S. patent application Ser. No. 08/341,826; and the Humicola lanuginosa strain DSM 4106
[6] Diethylenetriaminepentaacetate.
[7] Suds Booster according to the present invention, preferably a suds booster in accordance with Examples 1-6, more preferably poly(DMAM-b-HEA-b-Styrene)(1:3:0.33) of Example 4.
[8] Includes perfumes, dyes, ethanol, etc.

TABLE V

| Ingredients | weight % | | |
|---|---|---|---|
| | 20 | 21 | 22 |
| $C_{12}$-$C_{13}$ Alkyl ($E_{0.6-3}$) sulfate | — | 27.0 | — |
| $C_{12}$-$C_{14}$ Betaine | 2.0 | 2.0 | — |
| $C_{14}$ Amine oxide | 2.0 | 5.0 | 7.0 |
| $C_{12}$-$C_{14}$ Polyhydroxy fatty acid amide | 2.0 | — | — |
| $C_{10}$ Alcohol Ethoxylate $E_9$ [1] | 1.0 | — | 2.0 |
| Hydrotrope | — | — | 5.0 |
| Diamine [2] | 4.0 | 2.0 | 5.0 |
| $Ca^{2+}$ (as Ca(citrate)$_2$) | — | 0.1 | 0.1 |
| Protease [3] | — | 0.06 | 0.1 |
| Amylase [4] | 0.005 | — | 0.001 |
| Lipase [5] | — | 0.001 | — |
| DTPA [6] | — | 0.1 | 0.1 |
| Citrate (cit2K3) | 0.3 | — | — |
| Block polymeric suds booster [7] | 0.5 | 0.8 | 2.5 |
| Minors and water [8] | balance | balance | balance |
| pH of a 10% aqueous solution | 10 | 9 | 9.2 |

[1] $E_9$ Ethoxylated Alcohols as sold by the Shell Oil Co.
[2] 1,3-diaminopentane sold as Dytek EP.
[3] Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[4] Suitable amylase enzymes include Termamyl ®, Fungamyl ®; Duramyl ®; BAN ®' and the amylases as described in WO95/26397 and in co-pending application by Novo Nordisk PCT/DK/96/00056.
[5] Suitable lipase enzymes include Amano-P; M1 Lipase ®; Lipomax ®; Lipolase ®' D96L - lipolytic enzyme variant of the native lipase derived from Humicola lanuginosa as described in U.S. patent application Ser. No. 08/341,826; and the Humicola lanuginosa strain DSM 4106
[6] Diethylenetriaminepentaacetate.
[7] Suds Booster according to the present invention, preferably a suds booster in accordance with Examples 1-6, more preferably poly(DMAM-b-HEA-b-Styrene-bAA)(1:3:0.165:0.165) block polymer of Example 5.
[8] Includes perfumes, dyes, ethanol, etc.

TABLE VI

| Ingredients | weight % | | |
|---|---|---|---|
| | 23 | 24 | 25 |
| $C_{12}$-$C_{13}$ Alkyl ($E_{1.4}$) sulfate | 33.29 | 24.0 | — |
| $C_{12}$-$C_{13}$ Alkyl ($E_{0.6}$) sulfate | — | — | 26.26 |
| $C_{12}$-$C_{14}$ Polyhydroxy fatty acid amide | 4.2 | 3.0 | 1.37 |
| $C_{14}$ Amine oxide | 4.8 | 2.0 | 1.73 |
| $C_{11}$ Alcohol Ethoxylate $E_9$ [1] | 1.0 | 4.0 | 4.56 |
| $C_{12}$-$C_{14}$ Betaine | — | 2.0 | 1.73 |
| $MgCl_2$ | 0.72 | 0.47 | 0.46 |
| Calcium citrate | 0.35 | — | — |

TABLE VI-continued

| Ingredients | weight % | | |
|---|---|---|---|
| | 23 | 24 | 25 |
| Block polymeric suds booster [2] | 0.5 | 1.0 | 2.0 |
| Minors and water [3] | balance | balance | balance |
| pH of a 10% aqueous solution | 7.4 | 7.8 | 7.8 |

[1] $E_9$ Ethoxylated Alcohols as sold by the Shell Oil Co.
[2] Suds Booster according to the present invention, preferably a suds booster in accordance with Examples 1-6, more preferably poly(DMAM-b-MA)(3:1) block polymer of Example 6.
[3] Includes perfumes, dyes, ethanol, etc.

TABLE VII

| | 26 | 27 | 28 | 29 | 30 |
|---|---|---|---|---|---|
| AE0.6S [1] | 28.80 | 28.80 | 26.09 | 26.09 | 26.09 |
| Amine oxide [2] | 7.20 | 7.20 | 6.50 | 6.50 | 6.50 |
| Citric acid | 3.00 | — | — | — | — |
| Maleic acid | — | 2.50 | — | — | — |
| Block polymeric suds booster [3] | 0.22 | 0.22 | 0.20 | 0.20 | 0.20 |
| Sodium Cumene Sulfonate | 3.30 | 3.30 | 3.50 | 3.50 | 3.50 |
| Ethanol 40B | 6.50 | 6.50 | 6.50 | 6.50 | 6.50 |
| C10E8 | — | — | 3.00 | 3.00 | 3.00 |
| C11E9 [4] | 3.33 | 3.33 | — | — | — |
| Diamine [5] | 0.55 | 0.55 | 0.50 | 0.50 | 0.50 |
| Perfume | 0.31 | 0.31 | — | — | — |
| Water | BAL. | BAL. | BAL. | BAL. | BAL. |
| Viscosity (cps @ 70 F.) | 330 | 330 | 150 | 330 | 650 |
| pH @ 10% | 9.0 | 9.0 | 8.3 | 9.0 | 9.0 |

[1] C12-13 alkyl ethoxy sulfonate containing an average of 0.6 ethoxy groups.
[2] $C_{12}$-$C_{14}$ Amine oxide.
[3] Suds Booster according to the present invention, preferably a suds booster in accordance with Examples 1-6, more preferably poly(DMAM-b-HEA) (1:3) block polymer of Example 1.
[4] C11 Alkyl ethoxylated surfactant containing 9 ethoxy groups.
[5] 1,3 bis(methylamine)-cyclohexane.
[6] C10 Alkyl ethoxylated surfactant containing 8 ethoxy groups.
[7] 1,3 pentane diamine.

TABLE VIII

| | 31 | 32 | 33 | 34 | 35 |
|---|---|---|---|---|---|
| AE0.6S [1] | 26 | 26 | 26 | 26 | 26 |
| Amine oxide [2] | 6.5 | 6.5 | 7.5 | 7.5 | 7.5 |
| Citric acid | 3.0 | — | 2.5 | — | 3.0 |
| Maleic acid | — | 2.5 | — | 3.0 | — |
| C10E8 [6] | 3 | 3 | 4.5 | 4.5 | 4.5 |
| Diamine [5] | 0.5 | 0.5 | 1.25 | 0 | 1.25 |
| Diamine [7] | 0 | 0 | 0 | 1 | 0 |
| Block polymeric suds booster [3] | 0 | 0.2 | 0.5 | 0.5 | 0.5 |
| Sodium cumene sulphonate | 3.5 | 3.5 | 2 | 2 | 2 |
| Ethanol | 8 | 8 | 8 | 8 | 8 |
| pH | 9 | 9 | 9 | 8 | 10 |

[1] C12-13 alkyl ethoxy sulfonate containing an average of 0.6 ethoxy groups.
[2] $C_{12}$-$C_{14}$ Amine oxide.
[3] Suds Booster according to the present invention, preferably a suds booster in accordance with Examples 1-6, more preferably poly(DMAM-b-HEA) (1:3) block polymer of Example 1.
[4] C11 Alkyl ethoxylated surfactant containing 9 ethoxy groups.
[5] 1,3 bis(methylamine)-cyclohexane.
[6] C10 Alkyl ethoxylated surfactant containing 8 ethoxy groups.
[7] 1,3 pentane diamine.

What is claimed is:

1. A method of cleaning hard bathroom surfaces comprising applying to said surfaces a foam cleaner comprising a foaming agent and a block polymer;

wherein the block polymer comprises:
  i) one or more cationic group-containing units; and
  ii) optionally one or more additional building block units; provided that the block polymer has an average cationic charge density of about 15 or less at a pH of from about 4 to about 12;
wherein said block polymer further comprises:
  iii) one or more units having one or more hydroxyl groups, provided that said polymer has a Hydroxyl Group Density of about 0.5 or less.

2. The method according to claim 1 wherein said block polymer further comprises:
  iv) one or more units having one or more hydrophobe groups selected from the group consisting of non-hydroxyl groups, non-cationic groups, non-anionic groups, non-carbonyl groups, and/or non-H-bonding groups.

3. The method according to claim 1, wherein said block polymer has a Hydroxyl Group Density of from about 0.0001 to about 0.4.

4. The method according to claim 1, wherein said polymer further comprises a member of the group consisting of:
  v) units capable of having an anionic charge at a pH of from about 4 to about 12;
  vi) units capable of having an anionic charge and a cationic charge at a pH of from about 4 to about 12;
  vii) units having no charge at a pH of from about 4 to about 12; and
  viii) mixtures of units (v), (vi), (vii), and (viii).

5. The method according to claim 4, wherein said average cationic charge density ranges from about 0.05 to about 5 units per 100 daltons molecular weight at a pH of about 4 to about 12.

6. The method according to claim 1, wherein said block polymer comprises a cationic unit of the formula:

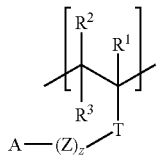

[I]

wherein each of $R^1$, $R^2$ and $R^3$ are independently selected from the group consisting of hydrogen, $C_1$ to $C_6$ alkyl, and mixtures thereof; T is selected from the group consisting of substituted or unsubstituted, saturated or unsaturated, linear or branched radicals selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, and carboalkoxy radicals and mixtures thereof; Z is selected from the group consisting of: —($CH_2$)—, ($CH_2$—CH=CH)—, —($CH_2$—CHOH)—, ($CH_2$—CHN$R^4$)—, —($CH_2$—CHR$^5$—O)— and mixtures thereof; $R^4$ and $R^5$ are selected from the group consisting of hydrogen, $C_1$ to $C_6$ alkyl and mixtures thereof; z is an integer selected from about 0 to about 12; A is NR$^6$R$^7$ or NR$^6$R$^7$R$^8$ wherein each of R$^6$, R$^7$ and R$^8$, when present, are independently selected from the group consisting of H, $C_1$-$C_8$ linear or branched alkyl, alkyleneoxy having the formula:

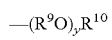

wherein $R^9$ is $C_2$-$C_4$ linear or branched alkylene, and mixtures thereof; $R^{10}$ is hydrogen, $C_1$-$C_4$ alkyl, and mixtures thereof; and y is from 1 to about 10.

7. The method according to claim 1, wherein said block polymer comprises a cationic unit of the formula selected from the group consisting of:

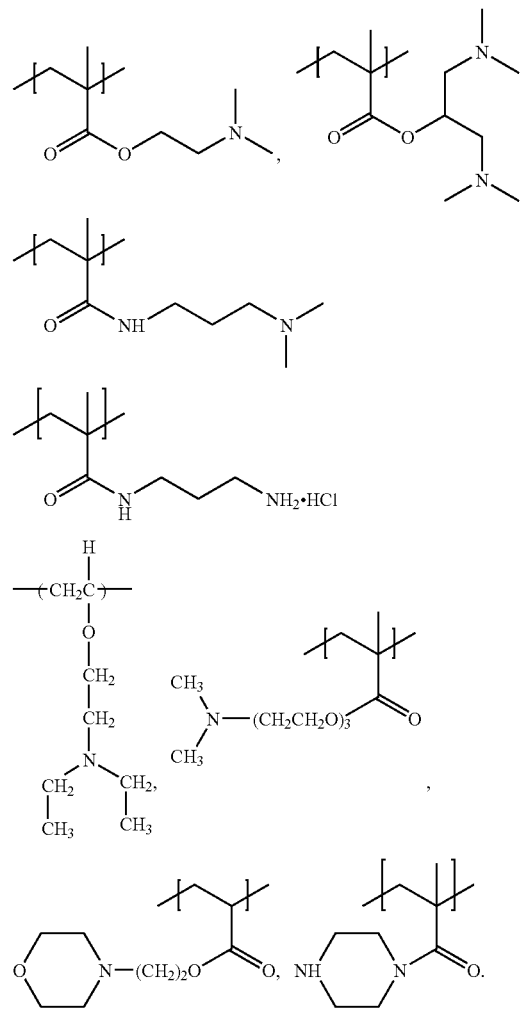

8. The method according to claim 1 wherein the block polymer comprises a member selected from the group consisting of:

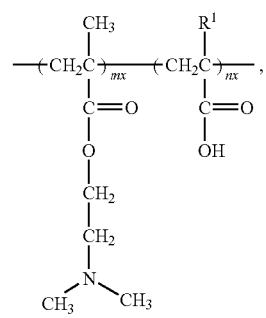

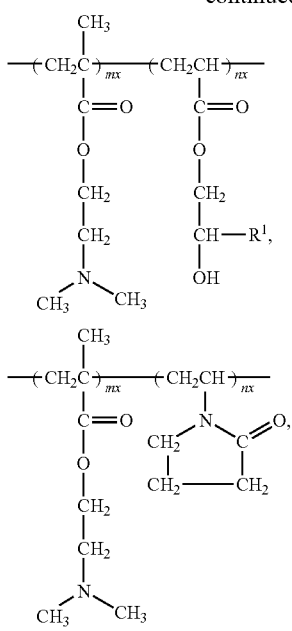

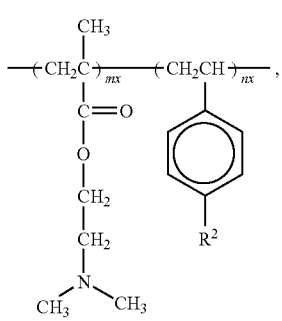

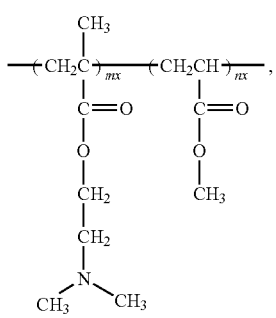

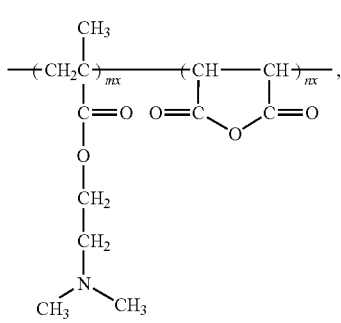

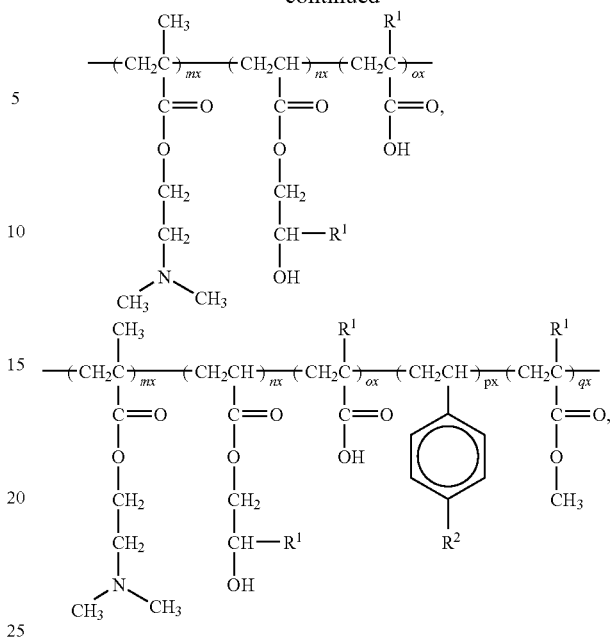

wherein $R^1$ is selected from H and $CH_3$; $R^2$ is selected from H and $SO_3H$; x represents the total number of monomer units within the block polymer; m, n, o, p, q when present, represent the mole ratio of their respective monomeric units in a given block polymer where at least two different monomeric units are present in the block polymer.

9. The method of claim 1, wherein the block polymer comprises said one or more cationic group-containing units and said one or more additional building block units,
wherein said one or more cationic group-containing units comprise at least a first homopolymeric unit comprising a series of first cationic monomeric units and
wherein said one or more additional building block units comprise at least a second hompolymeric unit comprising a series of second polymeric units,
at least said first monomeric units capable of having a cationic charge at a pH of from about 4 to about 12;
provided that said block polymer has an average cationic charge density from about 0.05 to about 5 units per 100 daltons molecular weight at a pH of from about 4 to about 12.

10. A method of cleaning hard bathroom surfaces comprising applying to said surfaces a foam cleaner comprising a foaming agent and a block polymer;
wherein the block polymer comprises at least one homopolymeric block of monomeric units A and at least one member of the group consisting of a homopolymeric block of monomeric units B and a homopolymeric block of monomeric units C:
A. said block of cationic monomeric units A having a Formula I:

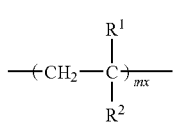

I wherein $R^1$ is H or an alkyl having 1 to 10 carbon atoms,
$R^2$ is a moiety selected from the group consisting of

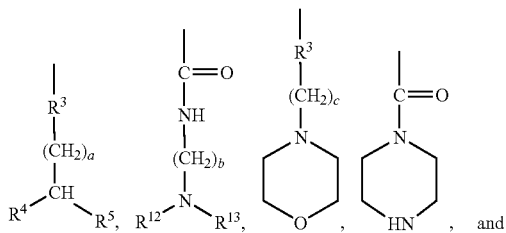
and

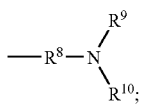

wherein $R^3$ is selected from the group consisting of

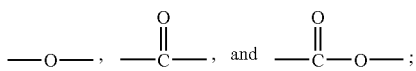

a is an integer from 0 to 16; b is an integer from 2 to 10; c is an integer from 2 to 10; d is an integer from 1 to 100;

$R^4$ and $R^5$ are independently selected from the group consisting of -H, and

—$R^8$—N$\begin{smallmatrix}R^9\\R^{10}\end{smallmatrix}$;

$R^8$ is independently selected from the group consisting of a bond and an alkylene having 1 to 18 carbon atoms;
$R^9$ and $R^{10}$ are independently selected from the group consisting of —H, alkyl having 1 to 10 carbon atoms;
$R^{12}$ and $R^{13}$ are independently selected from the group consisting of H and alkyl having from 1 to 10 carbon atoms;

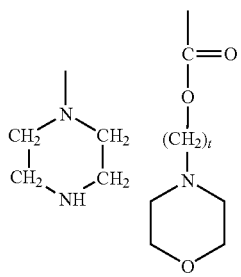

wherein t is an integer from 2 to 10;

B. said monomeric unit B is selected from the group consisting of:
a monomeric unit of Formula IV

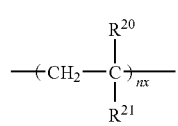

IV wherein $R^{20}$ is selected from the group consisting of H and $CH_3$;
$R^{21}$ is selected from the group consisting of:

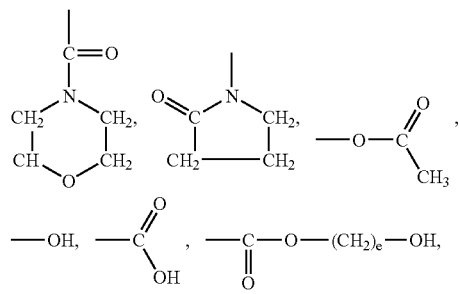

wherein e is an integer from 3 to 25;

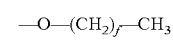

—O—$(CH_2)_f$—$CH_3$ wherein f is an integer from 0 to 25;

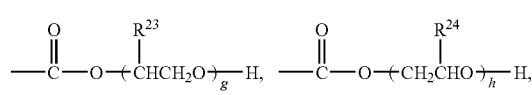

wherein g is an integer from 1 to 100,
h is an integer from 1 to 100,
$R^{23}$ is —H, —$C_{13}$ or —$C_2H_5$,
$R^{24}$ is —$CH_3$ or —$C_2H_5$;

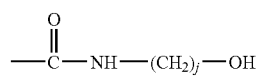

wherein j is an integer from 1 to 25;

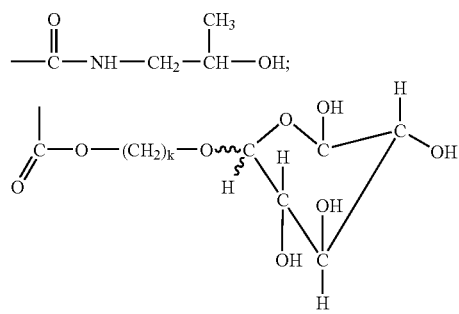

wherein k is an integer from 1 to 25;

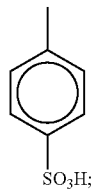

—NH—(CH$_2$)$_r$—NH$_2$.HCl, wherein r is an integer from 1 to 25; and a polyhydroxy monomeric unit of Formula VI.

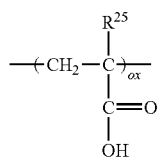   VI wherein w is an integer from 1 to 50; and

C. monomeric unit C is selected from the group consisting of:

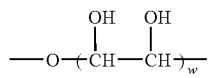

wherein R$^{25}$ is —H or —CH$_3$,

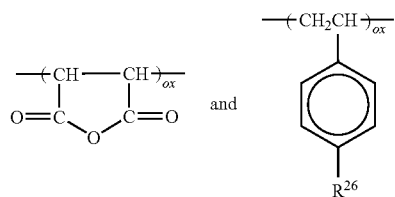   and wherein R$^{26}$ is —H or CH$_3$, and x represents the total number of monomeric units within the block polymer; m, n, o, when present, represent the mole ratio of their respective monomeric units in a given block polymer, wherein at least two different monomeric units are present in the block polymer.

11. The method of claim 10, wherein x represents the total number of monomeric units within the block polymer; m, n, o, when present, represent the mole ratio of their respective monomeric units in a given block polymer, wherein monomeric units A, B and C are present in the block polymer.

12. The method of claim 10, wherein said at least one monomeric unit A is selected from the group consisting of:

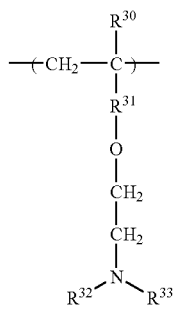

wherein R$^{30}$ is H or —CH$_3$, wherein R$^{31}$ is a bond or

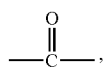

and

R$^{32}$ and R$^{33}$ are —CH$_3$ or —C$_2$H$_5$.

13. The method of claim 12, wherein said block polymer comprises at least one said monomeric unit A, at least one said monomeric unit B and at least one said monomeric unit C.

14. The method of claim 12, wherein said polymer is a terpolymer, said at least one monomeric unit B is selected from the group consisting of:

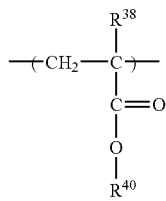

wherein R$^{38}$ is selected from the group consisting of H and CH$_3$ and

R$^{40}$ is selected from the group consisting of —CH$_2$CH$_2$—OH and

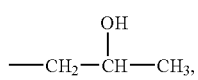

and isomers thereof, said terpolymer comprising said at least one monomeric unit C, wherein the molar ratio of said monomeric unit A : monomeric unit B : monomeric unit C is 1 to 9 : 1 to 9 : 1 to 6 respectively.

15. The method of claim 10, wherein the at least one monomeric unit B has the formula:

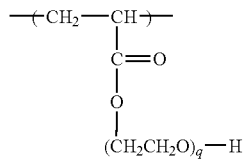

wherein q ranges from 1 to 12.

16. The method of claim 15, wherein the block polymer is a terpolymer, said at least one monomeric unit A is selected from the group consisting of:

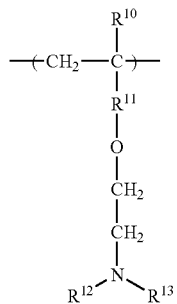

wherein $R^{10}$ is H or $CH_3$, $R^{11}$ is a bond or

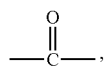

and $R^{12}$ and $R^{13}$ are $—CH_3$ or $—C_2H_5$, and said terpolymer comprises said at least one monomeric unit C.

17. The method of claim 16, wherein the molar ratio of monomeric unit A: monomeric unit B: monomeric unit C ranges from 1 to 9:1 to 9:1 to 3 respectively.

18. The method of claim 10, wherein said at least one monomeric unit A has a formula selected from the group consisting of:

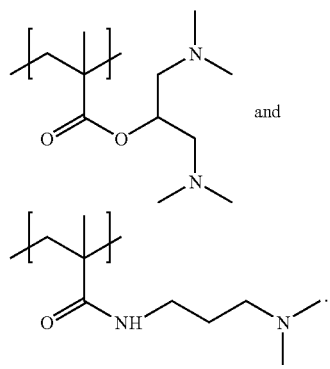

19. The method of claim 10, wherein said at least one monomeric unit B has a formula selected from the group consisting of:

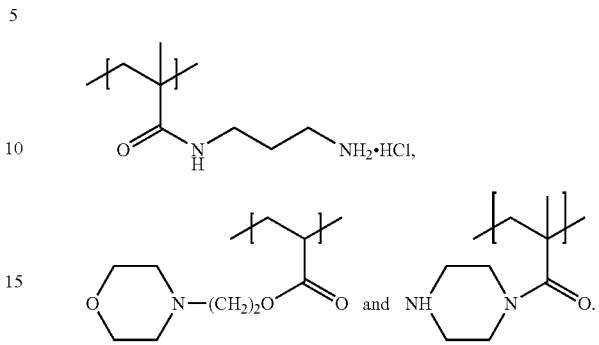

20. The method of claim 10, wherein said at least one monomeric unit B is selected from the group consisting of:

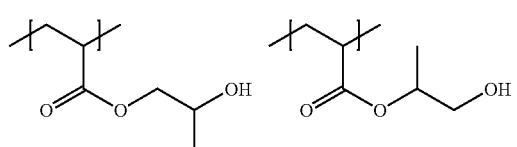

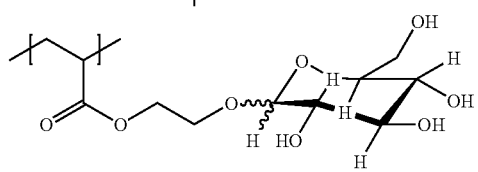

wherein n is an integer from 1 to 50,

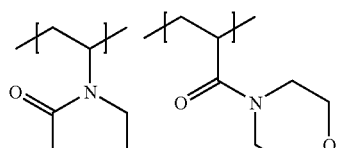

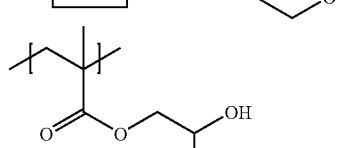

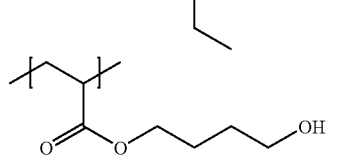

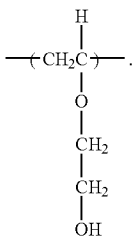

21. The method of claim 10, wherein the block polymer is selected from the group consisting of:
poly(HEA-co-DMAM-co-AA) terpolymer,
poly(HPA-co-DMAM-co-AA) terpolymer, and
poly(PEG-acrylate-co-DMAM-co-AA) terpolymer.

22. The method of claim 10, wherein the block polymer is selected from the group consisting of:
poly(HEA-co-DMAM) copolymer, poly(DMAM-co-butylvinylether) copolymer and poly(2-diethylaminoethylvinyl ether-co-ethyleneglycol monovinyl ether).

* * * * *